US007666828B2

(12) United States Patent
Bernhardt et al.

(10) Patent No.: US 7,666,828 B2
(45) Date of Patent: Feb. 23, 2010

(54) SULFONATED ESTOLIDES AND OTHER DERIVATIVES OF FATTY ACIDS, METHODS OF MAKING THEM, AND COMPOSITIONS AND PROCESSES EMPLOYING THEM

(75) Inventors: Randal J. Bernhardt, Antioch, IL (US); Gregory P. Dado, Chicago, IL (US); Dennis S. Murphy, Libertyville, IL (US); Lourdes R. Alonso, Deerfield, IL (US); Christopher A. Gariepy, Northbrook, IL (US); Eddie I. Filipovic, Evanston, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 12/353,751

(22) Filed: Jan. 14, 2009

(65) Prior Publication Data
US 2009/0188055 A1 Jul. 30, 2009

Related U.S. Application Data

(60) Provisional application No. 61/022,662, filed on Jan. 22, 2008.

(51) Int. Cl.
*C11D 1/28* (2006.01)
(52) U.S. Cl. .......................................... 510/495; 554/96
(58) Field of Classification Search .................. 510/495; 554/96
See application file for complete search history.

(56) References Cited

U.S. PATENT DOCUMENTS

| | | | |
|---|---|---|---|
| 2,581,375 A | 1/1952 | De Groote et al. | |
| 2,743,288 A | 4/1956 | Rueggeberg et al. | |
| 2,995,524 A | 8/1961 | Wylie et al. | |
| 3,377,290 A | 4/1968 | Werner et al. | |
| 3,668,153 A | 6/1972 | Crotty | |
| 3,898,187 A | 8/1975 | Miller | |
| 4,438,025 A * | 3/1984 | Satsuki et al. | 510/219 |
| 4,816,188 A | 3/1989 | Kitano et al. | |
| 4,936,551 A | 6/1990 | Behler et al. | |
| 5,002,683 A | 3/1991 | Behler et al. | |
| 5,294,726 A | 3/1994 | Behler et al. | |
| 5,329,030 A | 7/1994 | Schenker et al. | |
| 5,429,684 A | 7/1995 | Osberghaus et al. | |
| 5,441,156 A | 8/1995 | Fabry et al. | |
| 5,929,022 A | 7/1999 | Velazquez | |
| 6,242,406 B1 | 6/2001 | Katsuda et al. | |
| 6,294,513 B1 | 9/2001 | Jensen et al. | |
| 6,797,011 B2 | 9/2004 | Blangiforti | |
| 2002/0039979 A1 | 4/2002 | Aszman et al. | |
| 2004/0071653 A1 | 4/2004 | Bratescu et al. | |
| 2004/0242920 A1 | 12/2004 | Dado et al. | |
| 2005/0215456 A1* | 9/2005 | Goo et al. | 510/424 |

FOREIGN PATENT DOCUMENTS

DE 3926345 A1 2/1991

| | | | |
|---|---|---|---|
| EP | 0485500 A1 | 5/1992 | |
| EP | 0 511 091 A1 | 10/1992 | |
| GB | 1 047 772 A | 11/1966 | |
| GB | 1278421 A | 6/1972 | |
| GB | 1 380 390 A | 1/1975 | |
| WO | WO 90/02116 A1 | 3/1990 | |
| WO | WO 91/02045 A1 | 2/1991 | |
| WO | WO 91/13961 A1 | 9/1991 | |
| WO | WO 92/15660 A1 | 9/1992 | |
| WO | 00/18363 A1 | 4/2000 | |
| WO | 00/58430 A1 | 10/2000 | |
| WO | 01/53247 A1 | 7/2001 | |
| WO | 2005/113735 A1 | 12/2005 | |
| WO | WO 2006/062665 | * | 6/2006 |
| WO | WO 2009/094336 A3 | * | 7/2009 |

OTHER PUBLICATIONS

A.J. Stirton, et al.: "Surface-active properties of salts of alpha-sulphonated acids and esters" Journal Of The American Oil Chemists' Society, vol. 13, No. 1, Jan. 1954, pp. 13-16, XP002537683 Springer, Berlin, DE ISSN: 0003-021X DOI: 10.1007/BF02544763 The Whole Document.

PCT International Search Report and Written Opinion from International Application No. PCT/US2009/031455 mailed on Aug. 17, 2009.

PCT International Search Report and Written Opinion from International Application No. PCT/US2009/031608 mailed on Oct. 29, 2009.

PCT International Search Report and Written Opinion from International Application No. PCT/US2009/051299 mailed on Oct. 20, 2009.

(Continued)

*Primary Examiner*—John R Hardee
(74) *Attorney, Agent, or Firm*—McAndrews, Held & Malloy, Ltd.

(57) ABSTRACT

Sulfo-estolides and methods of making them are described. Useful methods include acid side bleaching, partial hydrogenation of the fatty acid, pretreatment of the fatty acid to provide color inhibition, acid side hydrolysis of the sulfo-estolides, or conversion of SHP to an essentially fully hydrolyzed product (HSHP) or a partially hydrolyzed product (PHSHP). Detergent formulations, such as laundry detergents, softeners, and other materials, containing any of these materials are disclosed. Laundry methods employing these formulations are also disclosed. These formulations are useful as laundry detergents and can be biodegradable, heavy duty liquids, 2× or 3× and up to 6× concentrates, low foaming, and/or effective in a high efficiency washing machine. Methods for laundering fabrics with the compositions are also disclosed.

76 Claims, No Drawings

OTHER PUBLICATIONS

PCT International Search Report and Written Opinion from International Application No. PCT/US2009/051318 mailed on Oct. 22, 2009.

PCT International Search Report and Written Opinion from International Application No. PCT/US2009/051319 mailed on Oct. 20, 2009.

PCT International Search Report and Written Opinion from International Application No. PCT/US2009/051464 mailed on Oct. 22, 2009.

* cited by examiner

SULFONATED ESTOLIDES AND OTHER DERIVATIVES OF FATTY ACIDS, METHODS OF MAKING THEM, AND COMPOSITIONS AND PROCESSES EMPLOYING THEM

RELATED APPLICATIONS

This application claims priority to U.S. Provisional Application Ser. No. 61/022,662 entitled, "Sulfonated Estolides and Other Derivatives of Fatty Acids, Methods of Making Them, and Compositions and Processes Employing Them" filed on Jan. 22, 2008, the complete subject matter of which is incorporated herein by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present technology, in general, relates to sulfo-estolides. More particularly, the present technology relates to sulfo-estolides derivatives and salts of sulfo-estolides, their methods of manufacture and the various applications and/or processes of utilizing them.

BRIEF SUMMARY OF THE INVENTION

In at least one aspect, the present technology provides a composition comprising one or more compounds having the following Formula 1:

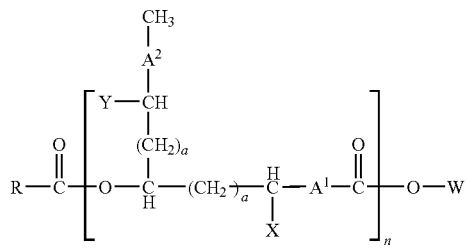

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or un-substituted hydrocarbon wherein the total number of carbon atoms is from about 1 to about 24; W is a monovalent or divalent metal cation, ammonium cation, substituted ammonium cation, H, or an alkyl or substituted alkyl group; and Z is H, or a monovalent or divalent metal cation, ammonium or substituted ammonium cation.

In another aspect, the present technology provides a method of laundering fabrics using one or more compositions of the presently described technology herein comprising the steps of placing one or more fabric articles to be laundered in a high efficiency or regular washing machine; placing a sufficient amount of one or more compositions of the present technology in the high efficiency or regular washing machine to provide a concentration of the composition in water of from about 0.001% by weight to about 5% by weight when the high efficiency washing machine is operated in a wash cycle; and actuating the wash cycle of the high efficiency or regular washing machine to launder the one or more fabric articles.

In a still further aspect, the present technology provides a method for hand laundering fabrics using one or more compositions of the presently described technology herein comprising the steps of placing one or more fabric articles to be hand laundered into a receptacle containing water; placing a sufficient amount of one or more compositions of the present technology into the receptacle to provide a concentration of the composition in water of from about 0.001% by weight to about 5% by weight; and hand washing the fabric article in the receptacle to launder the fabric article.

In at least one other aspect, the present technology provides a method for laundering one or more fabric articles using at least one composition of the presently described technology herein, comprising the steps of placing one or more fabric articles to be laundered in a high efficiency or regular washing machine that uses a washing medium to launder clothes; providing the composition comprising from about 1% to about 99% by weight of a sulfo-estolide; placing in the high efficiency or regular loading washing machine a sufficient amount of the at least one compositions of the present technology to provide a concentration of the composition in the washing medium of from about 0.001% by weight to about 5% by weight when the machine is operated in a wash cycle; and actuating the wash cycle of the high efficiency or regular washing machine to launder the one or more fabric articles.

In at least one additional aspect, the present technology provides a method of reducing the viscosity of at least one composition comprising at least one surfactant in water, the method comprising the step of including in the at least one composition a sufficient amount of one or more compounds of the present technology described herein, or mixtures thereof, effective to reduce the viscosity of the composition.

Further, at least one aspect of the present technology provides at least one surfactant composition comprising at least one surfactant, water, and an amount of one or more compositions of the present technology described herein, or mixtures thereof, effective to reduce the viscosity of the surfactant composition.

In addition, another aspect of the present technology provides a method of reducing the foam production of at least one composition comprising at least one surfactant in water, the method comprising the step of including in the composition an amount of one or more compositions of the presently described technology effective to reduce the foam production of the composition.

Furthermore, in another aspect, the present technology provides at least one surfactant composition comprising one or more surfactants, water, and a sufficient amount of one or more compositions of the presently described technology herein, effective to reduce the foam production of the surfactant composition.

Interestingly, the present technology also provides in a still further aspect, a method of cleaning at least one substrate, comprising the steps of providing at least one composition comprising a first surfactant comprising one or more compounds of the presently described technology, and a second surfactant comprising at least one anionic, cationic, nonionic, ampholytic, zwitterionic surfactant or combinations thereof;

contacting a soiled substrate with the composition; and removing the composition and soil from the substrate.

Additionally, the present technology also provides in another aspect at least one liquid laundry detergent composition, comprising from about 1% to about 99% by weight of at least one compound having the following Formula 1:

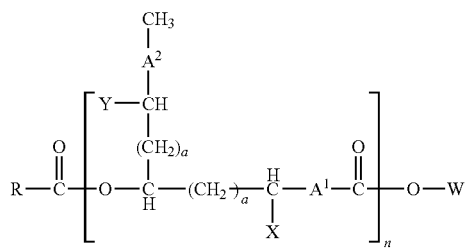

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or un-substituted, wherein the total number of carbon atoms is from about 1 to about 24; W is a monovalent or divalent metal cation, ammonium cation or substituted ammonium cation, H, or an alkyl or substituted alkyl group; Z is H, or a monovalent or divalent metal cation, ammonium or substituted ammonium cation; from 0% to about 40% by weight of at least one additional surfactant; and from about 1% to about 99% by weight of water.

In an additional aspect, the present technology provides a process of making a sulfo-estolide mixture comprising the steps of providing at least one unsaturated fatty carboxylic acid having from about 8 to about 24 carbon atoms; providing at least one chain termination agent having from about 4 to about 24 carbon atoms; sulfonating the unsaturated fatty carboxylic acid to form a sulfonated intermediate; and reacting the chain termination agent with the sulfonated intermediate to form a sulfo-estolide mixture.

Still further, in another aspect, the present technology provides a laundry concentrate composition, comprising from about 1% to about 99% by weight of at least one compound having the following Formula 1:

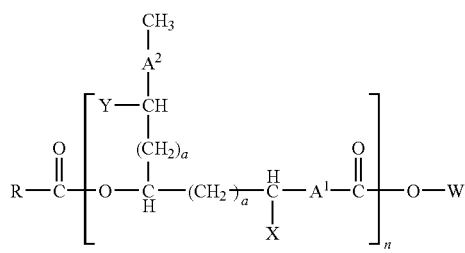

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or un-substituted hydrocarbon wherein the total number of carbon atoms is from about 1 to about 24; W is a monovalent or divalent metal cation, ammonium cation, substituted ammonium cation, H, or an alkyl or substituted alkyl group; Z is H, or a monovalent or divalent metal cation, ammonium or substituted ammonium cation; and from 0% to about 40% by weight of at least one additional surfactant; from about 1% to about 99% by weight of water; and from 0% to about 40% by weight of at least one additive.

Alternatively, in another aspect of the present technology there is provided a process of making a sulfo-estolide mixture comprising the steps of providing at least one unsaturated fatty acyl containing triglyceride having from about 27 to about 75 carbon atoms; providing at least one chain termination agent having from about 4 to about 24 carbon atoms; sulfonating the unsaturated fatty acyl to form a sulfonated intermediate; and reacting the chain termination agent with the sulfonated intermediate to form at least one sulfo-estolide mixture.

In another aspect, the present technology provides a laundry detergent composition, comprising from about 5% to about 90% by weight of at least one compound having the following Formula 1:

Formula 1

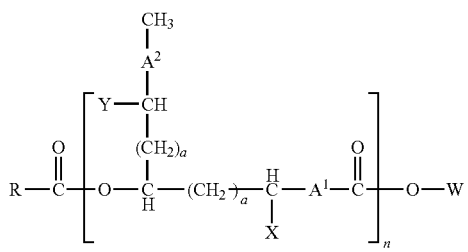

wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or un-substituted hydrocarbon wherein the total number of carbon atoms is from 1 to about 24; W is a monovalent or divalent metal cation, ammonium cation, substituted ammonium cation, H, or an alkyl or substituted alkyl group; Z is H, or a monovalent or divalent metal cation, ammonium or substituted ammonium cation; and from 0% to about 50% by weight of at least one nonionic surfactant; from 0% to about 25% by weight of at least one alcohol ether sulfate; a sufficient amount of at least three enzymes selected from the group consisting of cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, beta-glucanases, and arabinosidases, and wherein the composition has a pH value in the range of about 7 to about 10.

In a further aspect, the presently described technology provides a laundry detergent composition, comprising from about 5% to about 90% by weight of at least one compound having the following Formula 1:

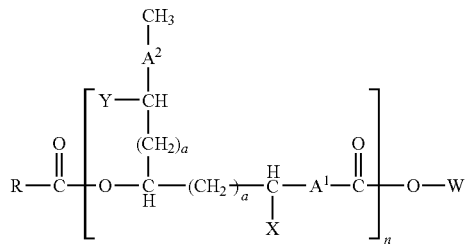

Formula 1 wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or un-substituted hydrocarbon wherein the total number of carbon atoms is from about 1 to about 24; W is a monovalent or divalent metal cation, ammonium cation, substituted ammonium cation, H, or an alkyl or substituted alkyl group; Z is H, or a monovalent or divalent metal cation, ammonium or substituted ammonium cation; and from 0% to about 50% by weight of at least one nonionic surfactant; from 0% to about 25% by weight of at least one alcohol ether sulfate; a sufficient amount of one or two enzymes selected from the group consisting of cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, beta-glucanases, and arabinosidases, and wherein the composition has a pH value in the range of about 7 to about 10.

As a further aspect, the present technology provides a laundry detergent composition, comprising from about 5% to about 90% by weight of at least one compound having the following Formula 1:

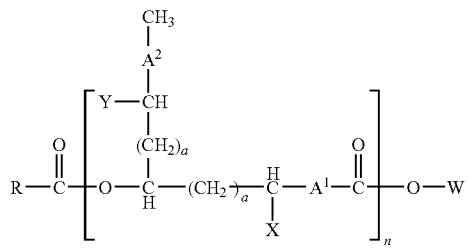

Formula 1 wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or un-substituted hydrocarbon wherein the total number of carbon atoms is from about 1 to about 24; W is a monovalent or divalent metal cation, ammonium cation, substituted ammonium cation, H, or an alkyl or substituted allyl group; Z is H, or a monovalent or divalent metal cation, ammonium or substituted ammonium cation; and from 0% to about 50% by weight of at least one nonionic surfactant; from 0% to about 25% by weight of at least one alcohol ether sulfate, and wherein the composition has a pH value in the range of about 7 to about 10 and is substantially free of enzymes.

As a still further aspect, the present technology provides a laundry detergent composition, comprising from about 5% to about 90% by weight of at least one compound having the following Formula 1:

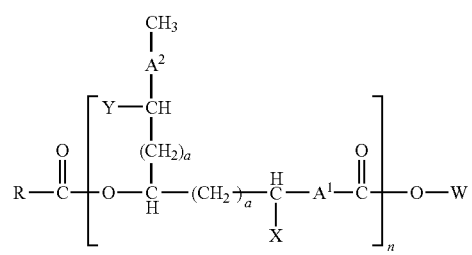

Formula 1 wherein n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or un-substituted hydrocarbon wherein the total number of carbon atoms is from 1 to about 24; W is a monovalent or divalent metal cation, ammonium cation, substituted ammonium cation, H, or an alkyl or substituted alkyl group; Z is H, or a monovalent or divalent metal cation, ammonium or substituted ammonium cation; and from 4% to about 50% by weight of at least one C16 alpha methyl ester sulfonate; from 0% to about 25% by weight of Cocamide diethanolamine, and wherein the composition has a pH value in the range of about 7 to about 10.

In an additional aspect, the present technology provides a laundry detergent composition, comprising from about 5% to about 90% by weight of at least one compound having the following Formula 1:

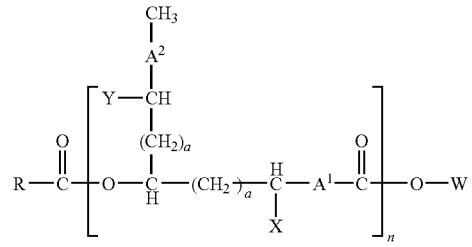

Formula 1 wherein n is an integer from 1-30; one of X and Y is SO$_3$—, the other of X and Y is H, and X and Y are independently assigned in each repeating unit; A$^1$ and A$^2$ are linear or branched, saturated or unsaturated, substituted or un-substituted, alkyl diradicals wherein the total number of carbons for each repeating unit is independent and in the range of C$_8$ to C$_{22}$; a is 0, 1, or 2, and is independently assigned in each repeating unit; R is linear or branched, saturated or unsaturated, substituted or un-substituted hydrocarbon wherein the total number of carbon atoms is from 1 to about 24; W is a monovalent or divalent metal cation, ammonium cation, substituted ammonium cation, H, or an alkyl or substituted alkyl group; Z is H, or a monovalent or divalent metal cation, ammonium or substituted ammonium cation; and from 0% to about 50% by weight of at least one nonionic surfactant; from 0% to about 25% by weight of at least one alcohol ether sulfate; from about 0.1% to about 5% by weight of metasilicate, and wherein the composition has a pH value greater than about 10.

Furthermore, in another aspect the present technology provides a laundry detergent composition, comprising from about 5% to about 90% by weight of at least one compound having the following Formula 1:

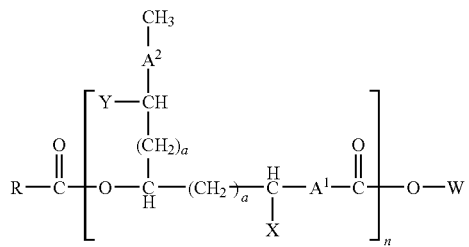

Formula 1 wherein n is an integer from 1-30; one of X and Y is SO$_3$—Z, the other of X and Y is H, and X and Y are independently assigned in each repeating unit; A$^1$ and A$^2$ are linear or branched, saturated or unsaturated, substituted or un-substituted, alkyl diradicals wherein the total number of carbons for each repeating unit is independent and in the range of C$_8$ to C$_{22}$; a is 0, 1, or 2, and is independently assigned in each repeating unit; R is linear or branched, saturated or unsaturated, substituted or un-substituted hydrocarbon wherein the total number of carbon atoms is from about 1 to about 24; W is a monovalent or divalent metal cation, ammonium cation, substituted ammonium cation, H, or an alkyl or substituted alkyl group; Z is H, or a monovalent or divalent metal cation, ammonium or substituted ammonium cation; and from 0% to about 50% by weight of at least one nonionic surfactant; from 0% to about 25% by weight of at least one alcohol ether sulfate; from 0% to about 20% by weight of sodium carbonate, and wherein the composition has a pH value greater than 10.

Additionally, another aspect of the present technology provides a laundry detergent composition, comprising from about 2% to about 90% by weight of one or more compounds having the following Formula 1:

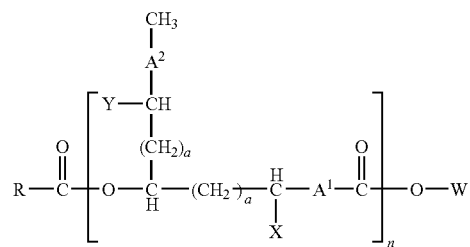

Formula 1 wherein n is an integer from 1-30; one of X and Y is SO$_3$—Z, the other of X and Y is H, and X and Y are independently assigned in each repeating unit; A$^1$ and A$^2$ are linear or branched, saturated or unsaturated, substituted or unsubstituted alkyl diradicals wherein the total number of carbons for each repeating unit is independent and in the range of C$_8$ to C$_{22}$; a is 0, 1, or 2, and is independently assigned in each repeating unit; R is a linear or branched, saturated or unsaturated, substituted or unsubstituted alkyl radical with from 1 to 24 carbon atoms; W is a monovalent or divalent metal cation, ammonium or substituted ammonium cation, H, or an alkyl or substituted alkyl group; Z is H, or a monovalent or divalent metal cation, ammonium or substituted ammonium cation; and from 2% to 40% by weight of at least one nonionic surfactant; from 0% to 32% by weight of at least one alcohol ether sulfate; from 0% to 25% by weight of at least one C16 alpha methyl ester sulfonate; from 0% to 6% by weight of lauryl dimethlyamine oxide; from 0% to 6% by weight of C$_{12}$EO$_3$; from 0% to 10% by weight of coconut fatty acid; from 0% to 3% by weight of borax pentahydrate; from 0% to 6% by weight of propylene glycol; from 0% to 10% by weight of sodium citrate; from 0% to 6% by weight of triethanolamine; from 0% to 6% by weight of monoethanolamine; from 0% to 1% by weight of at least one fluorescent whitening agent; from 0% to 1.5% by weight of at least one anti-redeposition agent; from 0% to 2% by weight of at least one thickener; from 0% to 2% by weight of at least one thinner; from 0% to 2% by weight of at least one protease; from 0% to 2% by weight of at least one amylase; and from 0% to 2% by weight of at least one cellulase.

Moreover, another aspect of the present technology provides a laundry detergent composition, comprising from about 2% to about 90% by weight of one or more compounds having the following Formula 1:

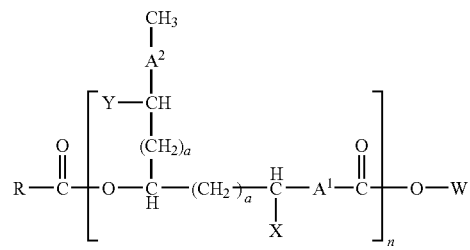

Formula 1 wherein, n is an integer from 1-30; one of X and Y is SO$_3$—Z, the other of X and Y is H, and X and Y are independently assigned in each repeating unit; A$^1$ and A$^2$ are linear or branched, saturated or unsaturated, substituted or unsubstituted alkyl diradicals wherein the total number of carbons for each repeating unit is independent and in the range of $C_8$ to $C_{22}$; a is 0, 1, or 2, and is independently assigned in each repeating unit; R is a linear or branched, saturated or unsaturated, substituted or unsubstituted alkyl radical with from 1 to 24 carbon atoms; W is a monovalent or divalent metal cation, ammonium or substituted ammonium cation, H, or an alkyl or substituted alkyl group; Z is H, or a monovalent or divalent metal cation, ammonium or substituted ammonium cation; from about 2% to about 40% by weight of at least one nonionic surfactant; from 0% to about 32% by weight of at least one or more alcohol ether sulfate; from 0% to about 6% by weight of lauryl dimethylamine oxide; from 0% to about 6% by weight of $C_{12}EO_3$; from 0% to 10% by weight of coconut fatty acid; from 0% to about 10% by weight of sodium metasilicate; from 0% to about 10% by weight of sodium carbonate; from 0% to about 1% by weight of at least one fluorescent whitening agent; from 0% to about 1.5% by weight of at least one anti-redeposition agent; from 0% to about 2% by weight of at least one thickener; and from 0% to about 2% by weight of at least one thinner.

Another aspect of the present technology provides a green laundry detergent composition, comprising from about 2% to about 90% by weight of one or more compounds having the following Formula 1:

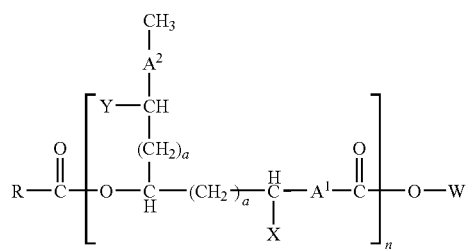

Formula 1 wherein, n is an integer from 1-30; one of X and Y is $SO_3$—Z, the other of X and Y is H, and X and Y are independently assigned in each repeating unit; $A^1$ and $A^2$ are linear or branched, saturated or unsaturated, substituted or unsubstituted allyl diradicals wherein the total number of carbons for each repeating unit is independent and in the range of $C_8$ to $C_{22}$; a is 0, 1, or 2, and is independently assigned in each repeating unit; R is a linear or branched, saturated or unsaturated, substituted or unsubstituted alkyl radical with from 1 to 24 carbon atoms; W is a monovalent or divalent metal cation, ammonium or substituted ammonium cation, H, or an alkyl or substituted alkyl group; Z is H, or a monovalent or divalent metal cation, ammonium or substituted ammonium cation; and from 0% to about 30% by weight of at least one C16 methyl ester sulfonate; from 0% to about 30% by weight of at least one C12 methyl ester sulfonate; from 0% to about 30% by weight of sodium lauryl sulfate; from 0% to about 30% by weight of Sodium stearoyl lactylate; from 0% to about 30% by weight of sodium lauroyl lactate; from 0% to about 60% by weight of alkyl polyglucoside; from 0% to about 60% by weight of polyglycerol monoalkylate; from 0% to about 30% by weight of lauryl lactyl lactate; from 0% to about 30% by weight of saponin; from 0% to about 30% by weight of rhamnolipid; from 0% to about 30% by weight of sphingolipid; from 0% to about 30% by weight of glycolipid; from 0% to about 30% by weight of at least one abietic acid derivative; and from 0% to about 30% by weight of at least one polypeptide.

DETAILED DESCRIPTION OF THE INVENTION

The present technology, in general, relates to sulfo-estolides. More particularly, the present technology relates to sulfo-estolides derivatives and salts of sulfo-estolides, their methods of manufacture and the various applications and/or processes of utilizing them. The compositions described here include, but are not limited to, sulfo-estolides having the structure of Formula 1:

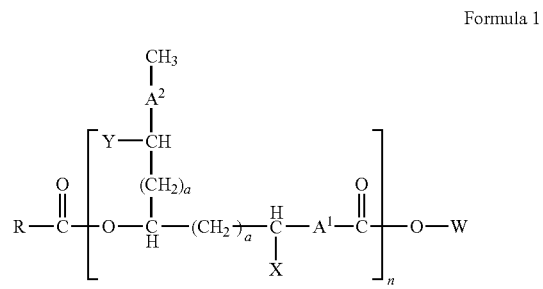

Formula 1

In Formula 1:

n is an integer from about 1 to about 30, alternatively about 1 to about 10, alternatively 1 to 4, alternatively 1, 2, or 3, alternatively 1 or 2, alternatively 1;

One of X and Y is $SO_3$—Z, the other of X and Y is H, and X and Y are independently assigned in each repeating unit;

$A^1$ and $A^2$ are independently selected linear or branched, saturated or unsaturated, substituted or unsubstituted alkyl diradicals, where the total number of carbons for each repeating unit is independent and in the range of $C_8$ to $C_{22}$. As defined here, the term "alkyl diradical" is meant to refer to a linking hydrocarbon or alkylene segment, for example but by no means limited to —$(CH_2)_3$—, —$(CH_2)_4$—, —$(CH_2)_5$—, and so forth;

a is 0, 1, or 2, and is independently assigned in each repeating unit. When a=0, 1, or 2, the functional group corresponds to an alpha-sulfo-estolide, beta-sulfo-estolide, or gamma-sulfo-estolide, respectively;

R can be linear or branched, saturated or unsaturated, substituted or un-substituted hydrocarbon, wherein the total number of carbon atoms can be from about 1 to about 24. In at least one embodiment, R has from about 7 to about 21 carbon atoms, alternatively from about 8 to about 16 carbon atoms, and can be a saturated or unsaturated linear or branched hydrocarbon, a linear or branched hydroxyalkane sulfonate, or a linear or branched alkene sulfonate. For example, in one embodiment, $A^1$ and $A^2$ are linear alkyl diradicals and R is saturated or unsaturated linear hydrocarbon, linear hydroxyalkane sulfonate, or linear alkene sulfonate having from about 7 to about 21, alternatively from about 8 to about 16 carbons;

W is a monovalent or divalent metal; ammonium; substituted ammonium; H; or a linear or branched, substituted or unsubstituted alkyl having from about 1 to about 22 carbon atoms. For example, W can be an alkali or alkaline earth metal cation. Alternatively, W can be a glycerine joined by an ester linkage, e.g., a substituted C3 alkyl such that the structure of Formula 1 is incorporated one or more times as an ester in a monoglyceride, a diglyceride, or a triglyceride.

Z is H or a monovalent or divalent metal cation, ammonium or substituted ammonium cation, preferably an alkali or alkaline earth metal cation, for example potassium, sodium, calcium, or magnesium, with potassium being preferred in certain embodiments. For example, it has been shown that at least in some embodiments, a heavy duty liquid laundry concentrate containing a potassium salt is significantly lower in viscosity than a comparable composition that contains the same amount of a sodium salt.

The above structure is illustrative of the sulfo-estolide products that may be derived from, for example, linear unsaturated fatty acid feedstocks. It is understood that sultone hydrolyzed products and structures of a comparable nature may be derived from branched and/or substituted unsaturated fatty acids or mixtures of linear and branched and/or substituted unsaturated fatty acids.

Additional sulfo-estolide compositions may be produced from fatty acid feedstocks comprising polyunsaturated fatty acids, where $A^1$ and $A^2$ may be independently selected from the set of alkyl diradicals that are: a) saturated; b) unsaturated, c) unsaturated and substituted with a sulfonate group, d) substituted with a hydroxyl group and a sulfonate group; d) substituted with a ester group and a sulfonate group (i.e., a sulfo-estolide).

In another embodiment of the present technology, the sulfo-estolide compositions are comprised of carboxylic esters, or are reported in an ester analysis as carboxylic esters. Although it is contemplated that at least some of these carboxylic esters are sulfo-estolides, the presently described technology is not limited by the accuracy of this belief, for example the compositions may contain carboxylic esters wherein X and Y within one or more repeating units, in Formula 1, are both H.

In another embodiment of the present technology, the sulfo-estolide compositions are comprised of sulfo-estolide of Formula 1 and a non-sulfonated estolide which comprises two or more fatty acid chains that does not contain a sulfonate group.

DEFINITIONS

The term "sulfo-estolide" ("SE") is used here to describe Formula 1. The term "partially hydrolyzed sulfo-estolide" ("PHSE") describes compositions of formula 1 wherein the esters have been partially hydrolyzed between (1% to 95%). The term "hydrolyzed sulfo-estolide" ("HSE") describes compositions of Formula 1 wherein the esters have been fully hydrolyzed (>95%).

The term "sultone hydrolyzed product" ("SHP") is used here to describe salts of sulfo-estolides that are produced from feedstock comprising unsaturated fatty acids by a process comprising the steps of sulfonation with $SO_3$, neutralization, and hydrolysis of sultones. The neutralization and hydrolysis are conducted at a level of caustic addition that maintains the pH in the range from about 4 to about 10

The resulting product contains carboxylic acid esters at a level that corresponds to about 5 to about 95 mol %, alternatively about 20 to about 60 mol %, alternatively about 20 to about 45 mol %, alternatively about 30 to about 45 mol % of the total carboxylic functionality in the composition. It is contemplated that none or few of the esters (whether they are sulfo-estolides or not) are hydrolyzed in process of making SHP. By processing at a low temperature and neutralizing the acid as it leaves the sulfonator as quickly as possible, it is contemplated that lower ester levels will be obtained. Through optimization of process conditions for production of esters, it is contemplated that products that have higher ester content will be obtained. For example, it is contemplated that the ester content may be obtained at lower and/or higher levels through the selection of the molar ratio of $SO_3$ to alkene functionality used in the sulfonation step, or alternatively or in addition, through the selection of the amount of monounsaturated and/or polyunsaturated fatty acids comprising the unsaturated fatty acid feedstock.

The term "ester hydrolyzed product" ("EHP") is used here to describe a sulfonate composition that is produced from unsaturated fatty acids by sulfonation with $SO_3$ to produce sulfo-estolide and subsequent hydrolysis of greater than about 95% of the carboxylic esters. For example the resulting product may have a carboxylic ester content that corresponds to less than about 5 mol %, alternatively less than about 2 mol %, alternatively less than about 1 mol % of the total carboxylic functionality in the composition.

The term "partially ester hydrolyzed products" ("PEHP") is used here to describe salts of sulfo-estolides that are produced from unsaturated fatty acids by sulfonation with $SO_3$ and hydrolysis of a portion of the carboxylic esters. The molar percentage of hydrolysis of carboxylic esters that is realized is from about 1% to about 95%, alternatively from about 5% to about 90%, alternatively from about 10% to about 90%, alternatively from about 20% to about 90%.

As defined here, the term "free alkalinity" is meant to refer to the total amount of carboxylate anion and hydroxide present in a composition, as may be measured by, for example, potentiometric titration of an aqueous solution with aqueous strong acid, for example HCl, to an endpoint of about pH 3 to about pH 4.5, or alternatively to bromophenol blue endpoint.

As defined here, the term "free caustic" is meant to refer to the total amount of excess strong alkalinity present in a composition, as may be measured by, for example potentiometric titration of an aqueous solution with aqueous strong acid, for example HCl, to an endpoint of about pH 9 to about pH 11.

A "repeating unit" means one instance of the subject matter enclosed by brackets in a formula. For example, if n=15 for a given molecule according to Formula 1, the molecule has 15 instances of the bracketed structure. Each instance of the bracketed structure can be identical to or different from other instances of the bracketed structure. For example, the Y moiety in Formula 1 can be H in one repeating unit and —$SO_3^-$Z in another repeating unit of the same molecule.

Making SE or Other Carboxylic Esters

A suitable starting material for the present process is a fatty acid (fatty carboxylic acid). Fatty acids that may be suitable for use in the present technology include but are not limited to linear unsaturated fatty acids of about 8 to about 24 carbons, branched unsaturated fatty acids of about 8 to about 24 carbons, or mixtures thereof. Unsaturated fatty acids provided from commercial sources containing both saturated and unsaturated fatty acids are suitable for use in the present technology. Mixtures of saturated fatty acids and unsaturated fatty acids are also contemplated. In a non-limiting example, fatty acid mixtures that are rich in oleic acid (cis-9-octadecenoic acid) are suitable feedstocks. Other unsaturated fatty acids, for example but not limited to, trans-octadecenoic acids or palmitoleic acid may also be employed in the presently described technology.

Suitable feedstocks may be derived from vegetable and/or animal sources, including but not limited to fatty acids and fatty acid mixtures derived from canola oil, corn oil, cottonseed oil, linseed oil, olive oil, palm oil, peanut oil, rapeseed oil, safflower oil, sesame oil, soybean oil, sunflower oil, tall oil, tung oil, lard, poultry fat, BFT (bleachable fancy tallow), edible tallow, coconut oil, cuphea oil, yellow grease and combinations of these. Also contemplated are genetically modified or engineered oils that include but are not limited to high oleic sunflower or soybean oil. In some embodiments, the preferred unsaturated fatty acid feedstocks may contain reduced levels of polyunsaturated fatty acids, for example, less than 15%, alternatively less than 10%, alternatively less than 5% on a total weight basis. In some additional embodiments, the fatty acid feedstocks may be obtained by the partial hydrogenation of unsaturated triglycerides, for example soybean oil, followed by hydrolysis of the oil to afford fatty acids that are enriched in monounsaturated fatty acids and depleted in polyunsaturated fatty acids. The above-noted triglycerides optionally hydrogenated, can also be used as feedstocks, alone or in combination with fatty acids. Still further, in some embodiments of the presently described technology, suitable feedstocks may include those that contain appreciable amounts of saturated fatty acids, for example up to about 80%, alternatively about 50%, alternatively about 30%, alternatively about 20% saturated fatty acid by weight. Alternatively, the feedstocks may be enriched in mono unsaturated fatty acids, for example, via distillation; however, undistilled feedstocks are preferred due to lower cost.

In certain embodiments, a chain termination agent can be included in the reaction to reduce or prevent the formulation of products of Formula 1 in which n is greater than one. The chain termination agent can be, for example, a saturated or unsaturated, substituted or unsubstituted, aliphatic or aromatic carboxylic acid having from 7 to 22 carbon atoms, or a combination of any two or more of these. The contemplated characteristic of a chain termination agent preferred for the present purpose is that it can form an ester. One class of preferred chain termination agents is a saturated fatty acid having from 8 to 22 carbon atoms, optionally from 8 to 14 carbon atoms, optionally 8, 10, or 12 carbon atoms or mixtures of these fatty acid species.

The compounds of Formula 1 and related compounds (for example, where n=0) can be made, for example, by: a) $SO_3$ sulfonation of a fatty acid, for example oleic acid; b) neutralization with aqueous caustic to afford a sulfonate salt solution with a pH in the range of about 4 to about 10; and c) hydrolysis of the resulting sultones, maintaining the reaction mixture at a pH of about 4 to about 10. Sulfonation can be carried out, for example, using a falling film $SO_3$ process.

Alternatively, the compounds of Formula 1 and related compounds (for example, where Z=H and W=H) can be made, for example, by falling film $SO_3$ sulfonation of a fatty acid, for example oleic acid, where the process temperature of the sulfonation is sufficient, for example greater than about 20° C., to result in the formation of carboxylic esters.

Continuous $SO_3$ sulfonation processes, including those that utilizing falling film reactors such as those described in Kirk-Othmer Encyclopedia of Chemical Technology, 5th ed., Vol. 23, Wiley-Interscience, Hoboken, N.J.: 2007, entry entitled "Sulfonation and Sulfation", pp. 513-562, which is hereby incorporated by reference, are suitable for conducting the sulfonation of feedstocks comprising unsaturated fatty acids in accordance with the presently described technology. For example, a monotube concentric reactor, annular film reactor, or multitube film reactor can be used to contact an unsaturated fatty acid feedstock, for example oleic acid, with a gaseous stream of $SO_3$ that is diluted with dry air. The molar ratio of $SO_3$ to alkene functionality in the fatty acid feedstock may be from about 0.3 to about 1.3, alternatively from about 0.5 to about 1.2, alternatively from about 0.8 to about 1.1, alternatively from about 0.9 to about 1.0.

In some embodiments, a preferred ratio, for example, is less than about 0.8 so as to minimize color formation. The fatty acid feedstock is provided to the reactor at a temperature above the melting point of the feedstock, i.e. the feedstock is provided as a liquid. The sulfonation is conducted such that the reaction mass is maintained as a mobile liquid throughout the course of reaction. Preferably, a means of cooling the reaction mixture during the course of contact between the feedstock stream and the gaseous $SO_3$ stream is provided so that the sulfonic acid product is produced from the reactor at a temperature of from about 10° C. to about 80° C., alternatively from about 20° C. to about 60° C., alternatively from about 30° C. to about 60° C.

Sulfonated unsaturated fatty acid salt and sulfonated hydroxy fatty acid salt products include, for example, those sold in Europe as Polystep® OPA by Stepan Co., and as Lankropol OPA and Lankropol OPA-V by Akzo Nobel, and in the United States as Calsoft® OS-45S by Pilot Chemical.

SE is produced from the sulfonation step and comprises carboxylic esters, provided that the reaction conditions are sufficient, for example a high enough temperature of the acid stream, to promote carboxylic ester formation. While not limiting the scope of the presently described technology, the temperature at which carboxylic ester formation may occur is greater than 10° C., alternatively greater than 20° C., alternatively greater than 30° C. The sulfonic acid products may further comprise sulfonic acid esters, including but not limited to cyclic esters, i.e., sultones.

In accordance with at least one embodiment, the presently described technology provides a process of making a sulfo-estolide mixture comprising the steps of:
  providing at least one unsaturated fatty carboxylic acid having from 8 to 24 carbon atoms;
  providing at least one chain termination agent having from 4 to 24 carbon atoms;
  sulfonating the unsaturated fatty carboxylic acid to form a sulfonated intermediate; and
  reacting the chain termination agent with the sulfonated intermediate to form a sulfo-estolide mixture.

In accordance with one embodiment, the process further comprises treating the sulfo-estolide mixture under conditions effective to at least reduce the concentrations of sultone moieties, in which the degree of esterification of the carboxylic acid moieties is at least about 5% after the treating step.

In accordance with at least one other embodiment, the presently described technology provides a process of making a sulfo-estolide mixture comprising the steps of:
  providing at least one unsaturated fatty acyl containing triglyceride having from 27 to 75 carbon atoms;
  providing at least one chain termination agent having from 4 to 24 carbon atoms;
  sulfonating the triglyceride to form a sulfonated intermediate; and
  reacting the chain termination agent with the sulfonated intermediate to form a sulfo-estolide mixture.

The SE produced from sulfonation can be immediately transferred to a vessel or reactor, for example a continuous neutralizer ("CN"), for the purpose of neutralizing sulfonic acids and at least a portion of the carboxylic acids that are present. Alternatively, aging of the SE sulfonic acid may be provided for the purpose of modifying the composition of the acid, particularly with regard to an increase in the amount of esters wherein X and Y within one or more repeating units, in Formula 1, are both H. Neutralization of the acids is accomplished by reaction with aqueous base, for example but not limited to aqueous NaOH, KOH, ammonium hydroxide, and metal carbonates. Combinations of two or more salts, such as mixed sodium and potassium salts in any proportions, are contemplated. In some embodiments, the amount of alkali that may be used in the neutralization is an amount that provides a neutralized product with a pH of about 4 to about 10. In these embodiments, the neutralized reaction mass may be produced in a way that minimizes the hydrolysis of carboxylic esters. In at least some of these embodiments, the amount of carboxylic ester hydrolysis that may occur may approach zero. When utilized, the CN may be operated with a mass fraction of acid of from about 0.1 to about 0.8, optionally about 0.5. The process can be carried out at a temperature of about 20 to about 100° C., alternatively about 55 to about 75° C., optionally about 65° C. The free alkalinity level, as measured by titration with aqueous HCl to a bromophenol blue endpoint, optionally using potash (potassium hydroxide) as the caustic, can be from 0 to about 3.5 wt. %, optionally about 2.5 wt. %. Note that all percentages are by weight in this specification, unless otherwise indicated. In a non-limiting example, the final average additions to the CN can be approximately 50% SE sulfonic acid, 35% water, and 15% caustic (50% concentration).

In another aspect of the presently described technology, neutralization of the SE sulfonic acid may be conducted using an amount of aqueous base that is sufficient to neutralize all free acid functionality in the SE product, including carboxylic acids, and is sufficient to provide an excess of free caustic that is available to further react for the purposes of sultone hydrolysis, sulfonic acid anhydride hydrolysis, sulfonic carboxylic acid ester hydrolysis, and a desired amount of carboxylic ester hydrolysis, provided that adequate time and temperature for ester hydrolysis is subsequently provided. In one embodiment of this aspect, the amount of base is sufficient to enable from about 1% to about 95% hydrolysis of carboxylic esters. In another embodiment of this aspect, the amount of alkali is sufficient to enable hydrolysis of greater than about 95% of carboxylic esters, alternatively practically all carboxylic esters present in the sulfonic acid intermediate. In this embodiment, the resulting product that can be obtained by subsequently providing adequate time and temperature for ester hydrolysis to occur has a carboxylic ester content that may correspond to, for example, less than about 5%, alternatively less than about 2%, alternatively less than about 1% of the total carboxylic functionality in the composition. In these ways, EHP and PEHP can be produced.

Hydrolysis of Sultones

In one aspect of the presently described technology where a neutralized SE is produced with a pH of from about 4 to about 10, the neutralized product can be subjected to a hydrolysis step for the purpose of hydrolyzing sultones, sulfonic acid esters, and acid anhydrides. This sultone hydrolysis step may be conducted under conditions that prevent significant sultone hydrolysis of carboxylic esters in the product. The temperature of the sultone hydrolysis reaction mixture may be from about 20° C. to about 140° C., alternatively from about 50° C. to about 90° C. In some embodiments, the pH of the reaction mixture may be maintained in the range of about 4 to about 10 throughout the course of reaction without the need to add additional caustic. In some additional embodiments, additional caustic may be added to ensure that the pH is maintained in the range of about 4 to about 10. The sultone hydrolysis may be conducted in a continuous or batch process method and may be conducted for an amount of time necessary to result in a stabilized level of free alkalinity, as may be judged, for example, by titration to bromophenol blue endpoint with aqueous HCl.

It is contemplated that hydrolysis of sultones may be conducted at a pH above about 10 without substantial carboxylic ester hydrolysis provided that the reaction temperature and free caustic are maintained sufficiently low.

Hydrolysis of Carboxylic Esters

In one aspect of the presently described technology, carboxylic esters present in SE and optionally SHP may optionally be subjected to an alkaline hydrolysis step for the purpose of converting carboxylic esters into carboxylates to afford EHP and/or PEHP. This ester hydrolysis step may be conducted concurrently with a step to hydrolyze sultones or in a subsequent separate step. The ester hydrolysis step may be conducted in a batch, semi-batch, or continuous reaction mode. For example, the ester hydrolysis may be conducted in a stirred tank reactor, a loop reactor, a plug flow reactor, a single or multi-stage continuous stirred tank reactor, or any other reactor that can provide adequate temperature and time to afford an ester hydrolyzed product. Alkaline hydrolysis of the carboxylic esters may be conducted at a temperature of about 20° C. to about 150° C., alternatively about 50° C. to about 150° C., alternatively about 70° C. to about 150° C. In one non-limiting example, the ester hydrolysis is conducted at about 85° C. for about 4 hours.

The pH of the reaction mixture during the ester hydrolysis reaction, as measured on diluted samples, for example about 1 wt % of sample diluted in water, is greater than about 9.5, optionally greater than about 10. Since free caustic is consumed by the ester hydrolysis reaction, sufficient caustic is preferably provided to maintain the pH of reaction mixture above about 9.5. The amount of caustic that may be used in the ester hydrolysis step is preferably greater than the amount of caustic required to neutralize any free acid that may be present in the reaction mass, including carboxylic acids, and to hydrolyze sultones, sulfonic acid esters and anhydrides that may be present. In a given reaction mass, the amount of free caustic that may be available to hydrolyze carboxylic esters may be measured, for example, by potentiometric titration of an aliquot of reaction mass diluted in water with aqueous HCl to an endpoint between about pH 9 and about 10. In some embodiments, an amount of free caustic is provide that is sufficient to hydrolyze from about 1 to about 100% of carboxylic esters present in SE. If so desired, a substantial excess of free caustic relative to carboxylic ester content may be used in order to ensure a very high degree of ester hydrolysis.

In another aspect of the presently described technology, carboxylic esters present in SE may be hydrolyzed with water under acidic conditions. For example, it is contemplated that the degree of ester hydrolysis may be controlled by the amount of water that is mixed with the SE sulfonic acid, the reaction temperature, and the reaction time. Complete and partial ester hydrolysis of carboxylic esters by this method is contemplated.

It is further contemplated that the sultones, sulfonic acid esters, and/or anhydrides present in SE sulfonic acid products may be hydrolyzed with water under acidic conditions. It is contemplated that suitable reaction conditions will allow the hydrolysis of sultones, sulfonic acid esters, and/or anhydrides, and any other species that may be susceptible to acid hydrolysis to occur with or without hydrolysis of carboxylic esters.

Neutral Bleaching

In at least one embodiment, bleaching of neutralized products of SE may be conducted by treating the products with aqueous hydrogen peroxide, for example 35% $H_2O_2$, in a bleaching reaction that is conducted at a temperature of about 20° C. to about 150° C., alternatively about 50° C. to about 120° C., alternatively about 70° C. to about 100° C. Alternatively, metal hypochlorite, ozone, or any other oxidant or other material that is effective as a bleaching agent may be used. The hydrogen peroxide or alternative oxidizing agent may be used in any amount that is effective in providing a desired color reduction. For example, aqueous hydrogen peroxide may be added to provide about 0.05% to about 5% by weight active hydrogen peroxide, alternatively from about 0.1% to about 3%. The bleaching of the neutralized product may be conducted in the same step as the sultone hydrolysis, or may be conducted in a separate step. For example, if carried out concurrently, hydrogen peroxide can be added at about 2% (wt/wt) concentration (at 100% active) to a reaction vessel used to conduct sultone hydrolysis. The free alkalinity and free peroxide can be measured periodically until the targeted % free alkalinity level, for example 1.8%-2.0% is reached. If the % free alkalinity is lower than the target before sultone hydrolysis is complete, then an additional amount of base can be added to maintain the target levels. In at least one embodiment, it is preferable that the amount of free peroxide in the reaction mixture be maintained above about 20 ppm, alternatively above about 100 ppm, alternatively above about 500 ppm, so as to avoid discoloration of the reaction mass, adding additional amounts of hydrogen peroxide if necessary.

If required or desired, additional hydrogen peroxide can be added after sultone hydrolysis is completed for the purpose of enabling additional bleaching of the SHP. If required or desired, a reducing agent such as $SO_2$ or sulfurous acid, or metal salts thereof, can be added at or near the end of the bleaching step in order to reduce residual free peroxide to a desired level.

In accordance with some embodiments, it is preferable to conduct the bleaching of neutralized products of sulfo-estolides with hydrogen peroxide at a pH in the range of about 4.5 to about 7.5, alternatively about 5 to about 7, wherein these ranges correspond to pH values measured on diluted samples, for example about 1 wt % or about 2 wt % of sample diluted in water. Preferably, the pH of the bleaching reaction mixture is maintained, at least initially, below a pre-determined level that is necessary to minimize hydrogen peroxide decomposition, to prevent severe foaming of the reaction mixture, and to improve color reduction. It has been found that if the pH of the bleaching reaction mixture is at and above that pre-determined level, at least during the initial stage of bleaching reaction, substantial peroxide decomposition and severe foaming occurs. Without intending to be bound by any particular theory, it is believed that such decomposition and severe foaming may be dependent on a number of factors, including dissolved metal ions in the reaction mixture, exposure to metal reaction equipment surfaces, and bleaching reaction temperature. It is contemplated that the decomposition of bleaching agent may be altered or mitigated through the incorporation of stabilizers, including but not limited to metal chelating agents, or alternatively through the passivation of metal surfaces or the use of non-metal surface process equipment.

Adjusting pH to Improve Product Stability Against Inhomogeneity

In some preferred embodiments, a concentrated aqueous solution of SHP, PEHP, and EHP may be prepared in a process comprising at least the steps of sulfonating a feedstock comprising an unsaturated fatty acid, neutralizing the resulting SE sulfonic acid intermediate, and hydrolyzing sultones. In these preferred embodiments, it is preferable that the pH of the final concentrated aqueous solution to be stored, transported, and optionally handled in additional ways and is maintained in a pH range that enables a clear, homogeneous liquid product, free of substantial precipitation or other physical form instability. Surprisingly, it has been discovered that specific pH ranges can lead to physical instability as characterized by precipitation of solids and/or separation of liquid product into two or more layers. Inorganic salt, nonsulfonated-estolide, and fatty acid levels can be controlled to provide a substantially precipitate free phase stable physical form. The ratios of these components will be dependent upon the temperature and concentration of SE in the composition.

Acid Bleaching

One way to reduce color is by bleaching SE sulfonic acid before neutralizing, which can be referred to as acid bleaching. Acid bleaching of SE may have the advantage, by itself or in combination with additional bleaching after neutralization, of reducing the color of SE more than would normally be achieved by neutral bleaching as described above. Acid bleaching may be carried out, for example, by adding about 0.1% to about 8% active $H_2O_2$, alternatively about 0.5% to about 4% active $H_2O_2$, providing for inclusion of water at a level of about 0.1% to about 50%, alternatively about 1% to about 25%, alternatively about 3% to about 12%, and maintaining the bleaching reaction temperature from about 20° C. to about 100° C., alternatively at about 50° C. A critical aspect to SE acid bleaching is the incorporation of water into the bleaching reaction mixture such that the total water in the sulfonic acid mixture is above a level that is necessary to stabilize the hydrogen peroxide in the reaction mixture and to afford an improved bleaching result.

In at least some preferred embodiments, wherein bleached SE sulfonic acid is converted to SHP, it is preferred to maintain peroxide at a level above about 100 ppm of hydrogen peroxide, alternately about 500 ppm, throughout the sultone hydrolysis reaction. Within these embodiments, it is additionally preferred to maintain the hydrolysis reaction mixture, at least initially, at a pH below about 7.5 alternatively about 7.0, wherein these values correspond to pH values measured on diluted samples, for example about 1 wt % or about 2 wt % of sample diluted in water. In at least some embodiments, it is preferable to maintain the sultone hydrolysis reaction mixture, at least initially, at a pH in the range of about 4.5 to about 7.5, alternatively about 5 to about 7, so as to enable additional bleaching of the reaction mixture during the sultone hydrolysis reaction.

In methods comprising the step of bleaching SE sulfonic acid with aqueous hydrogen peroxide to produce a bleached acid, the acid bleaching reaction mixture may further comprise about 1 to about 500 alternatively about 5 to about 100 ppm of a transition metal cation selected from the group $Fe^{2+}$, $Fe^{3+}$, $Mn^{2+}$, $Mn^{3+}$, and $Mn^{4+}$ for the purpose of providing for a substantial improvement in bleaching result and/or acceleration of the bleaching reaction. In addition or alternatively in these methods, aqueous base may be used as a source of water in the bleaching acid reaction mixture so as to enable the production of higher solids in the final SE salt product than can be achieved in comparable processes that utilize water instead of aqueous base. In at least some instances the use of aqueous base in the bleaching acid reaction mixture can substantially increase the stability of peroxide in the reaction mixture.

Hydrogenation

Another way to reduce the color of SE, which is not believed to be known, is to use a partially hydrogenated feedstock, for example an oleic acid feedstock or a soybean oil feedstock, to reduce or eliminate polyunsaturates. In one contemplated process, the proportion of triunsaturates such as linolenic acid can be reduced or eliminated by hydrogenation. In another contemplated process, hydrogenation is carried further to reduce the percentage of polyunsaturates in the fatty acid feedstock to less than about 20%, alternatively less than 10%, alternatively less than 5%. One potential advantage of this process is that hydrogenation of polyunsaturation may produce trans fatty acids, which in this process is contemplated to lead to beneficial differences in the final composition or its performance. The hydrogenation can be carried out either on the parent oil or the fatty acid derived therefrom.

Product Descriptions

The compositions of the present technology defined by Formula 1, are now believed by the present inventors to be comprised of complex mixtures of compounds that are monomeric, dimeric, and higher-order oligomeric species in terms of the number of originating fatty acid chains. The oligomerization in these mixtures is via the formation of ester linkages. Branched oligomers are also contemplated.

The sulfo-estolide functional group corresponds structurally to the condensation of the hydroxyl group of an internal hydroxy sulfonate of fatty acid with the carboxylic acid group of a second fatty acid chain, where the second fatty acid chain may be, but is not necessarily limited to: a) an unsaturated or saturated fatty acid; b) an internal hydroxy sulfonate of fatty acid; c) an internal alkene sulfonate or corresponding cyclic anhydride (i.e. sultone) of fatty acid; or d) an internal mono- or poly sulfo-estolide of two or more fatty acids (i.e., trimer, tetramer, etc.). The position of the sulfonate group along the back bone of the fatty acid chains is dictated by the location of the double bond in the starting material (9-octadecenoic acid for example) and the "direction" in which $SO_3$ adds across the double bond (thus, 9- and 10-sulfonate positions from oleic acid).

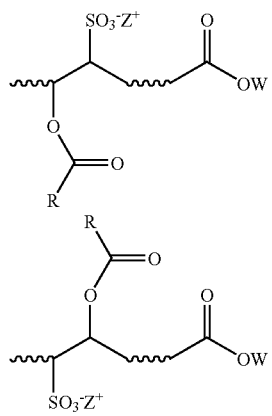

where R:

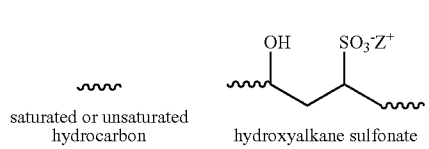

saturated or unsaturated hydrocarbon     hydroxyalkane sulfonate

-continued

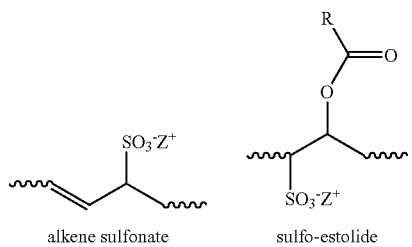

alkene sulfonate     sulfo-estolide

Non-ester-containing monomeric components made by this process are believed to comprise, in part, specific internal hydroxy sulfonates of fatty acid. For example, with 9-octadecenoic acid, the sulfonate groups are believed to be attached to the 9-position and alternatively the 10-position of the fatty acid. Examples are shown below.

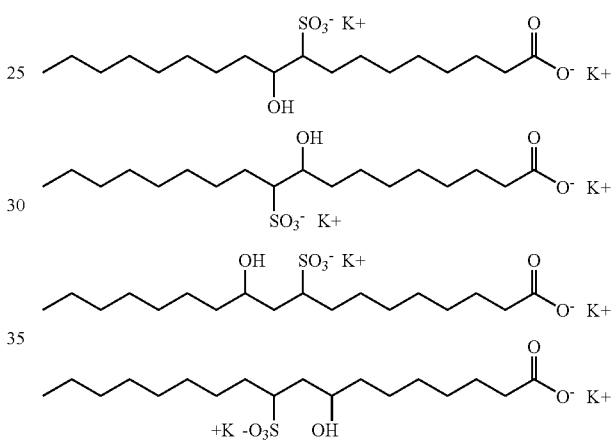

The monomeric components are further believed to comprise, in part, specific internal alkene sulfonates of fatty acid. These components may comprise cis- and/or trans-double bonds. It is also possible that compounds are present where the unsaturation is at the position of the sulfonate group (i.e., vinylic sulfonates). Examples are shown below.

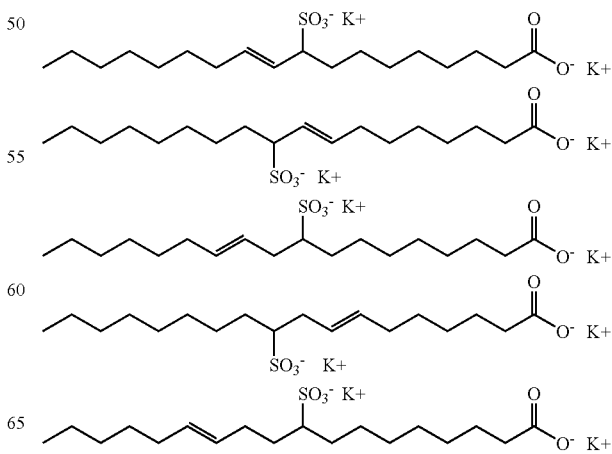

-continued

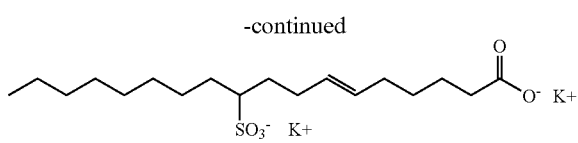

The monomeric components may further comprise disulfonated species, unsaturated fatty acids, and saturated fatty acids.

EHP is sometimes used here as a designation for sulfonated products that have been subjected to complete hydrolysis of sulfo-estolide functionality. Such hydrolysis can be accomplished by, for example, treatment of SHP with excess base under high pH conditions (for example >11) at elevated temperatures (for example 85-100° C.). EHP is believed to comprise a mixture of hydroxyalkane sulfonates and alkene sulfonates of comparable structure to the monomeric components of sulfo-estolide compositions, though not necessarily in comparable ratios. This mixture is comparable in composition to the compositions of sulfonated unsaturated fatty acids that are described in the art, for example, in T. W. Sauls and W. H. C. Rueggeberg, Journal of the American Oil Chemists Society (JAOCS), Volume 33, Number 9, September, 1956, pp 383-389.

It can be appreciated that PHEP will be comprised of elevated amounts of monomeric hydroxyalkane sulfonates and alkene sulfonates while maintaining some level of sulfo-estolide functionality.

General Considerations for Heavy Duty Liquid (HDL) Laundry Detergents

Desirable surfactant attributes for HDL's include being in liquid form at room temperature, an ability to be formulated in cold-mix applications, and an ability to perform as well as or better than existing surfactants.

Desirable attributes for HDLs include, for example, the ability to emulsify, suspend or penetrate greasy or oily soils and suspend or disperse particulates, in order to clean surfaces; and then prevent the soils, grease, or particulates from re-depositing on the newly cleaned surfaces.

It is also desirable to have the ability to control the foaming—for use of an HDL in a high efficiency (it should be appreciated that all high efficiency ("HE") washing machines includes all front loading washing machines as well) washing machine, low foam is desired to achieve the best cleaning and to avoid excess foaming. Other desirable properties include the ability to clarify the formulation and to improve stability.

Formulation Viscosity

Formulations are contemplated having a viscosity of 5 cPs to 200 cPs, measured at 25° C. using a Brookfield Viscometer model LV, spindle #2, speed 5 rpm. Certain SHP, PEHP, or EHP formulations have been found to have lower viscosity than comparable formulations lacking these surfactants, so these compositions function as viscosity reducers, which is very useful for making the contemplated highly concentrated, (e.g. greater than 40% surfactant active) detergent formulations.

Detergent Compositions

A wide variety of detergent compositions can be made that include SE, PHSE, HSE, SHP, PEHP, EHP, or combinations of two or all of these, as described in the present application, with or without other ingredients as specified below. Formulations are contemplated including 1% to 99% SE, PHSE, HSE, SHP, PEHP, and/or EHP, more preferably between 1% and 60%, even more preferably between 1% and 30%, with 99% to 1% water and, optionally, other ingredients as described here.

Surfactants

The detergent compositions can contain co-surfactants, which can be anionic, cationic, nonionic, ampholytic, zwitterionic, or combinations of these.

Anionic Surfactants

Although it is preferred that SHP be the only anionic surfactant used in the formulation, other anionic surfactants can be added. "Anionic surfactants" are defined here as amphiphilic molecules with an average molecular weight of less than about 10,000, comprising one or more functional groups that exhibit a net anionic charge when in aqueous solution at the normal wash pH, which can be a pH between 6 and 11. The anionic surfactant used in the present technology can be any anionic surfactant that is substantially water soluble. "Water soluble" surfactants are, unless otherwise noted, here defined to include surfactants which are soluble or dispersible to at least the extent of 0.01% by weight in distilled water at 25° C. It is preferred that at least one of the anionic surfactants used in the present technology be an alkali or alkaline earth metal salt of a natural or synthetic fatty acid containing between about 4 and about 30 carbon atoms. It is especially preferred to use a mixture of carboxylic acid salts with one or more other anionic surfactants. Another important class of anionic compounds is the water soluble salts, particularly the alkali metal salts, of organic sulfur reaction products having in their molecular structure an alkyl radical containing from about 6 to about 24 carbon atoms and a radical selected from the group consisting of sulfonic and sulfuric acid ester radicals.

Specific types of anionic surfactants are identified in the following paragraphs. At least in some embodiments, alkyl ether sulfates are preferred. A less preferred anionic surfactant is linear alkyl benzene sulfonate due to its lower solubility.

Carboxylic acid salts are represented by the formula:

where $R^1$ is a primary or secondary alkyl group of 4 to 30 carbon atoms and M is a solubilizing cation. The alkyl group represented by $R^1$ may represent a mixture of chain lengths and may be saturated or unsaturated, although it is preferred that at least two thirds of the $R^1$ groups have a chain length of between 8 and 18 carbon atoms. Non-limiting examples of suitable alkyl group sources include the fatty acids derived from coconut oil, tallow, tall oil and palm kernel oil. For the purposes of minimizing odor, however, it is often desirable to use primarily saturated carboxylic acids. Such materials are well known to those skilled in the art, and are available from many commercial sources, such as Uniqema (Wilmington, Del.) and Twin Rivers Technologies (Quincy, Mass.). The solubilizing cation, M, may be any cation that confers water solubility to the product, although monovalent such moieties are generally preferred. Examples of acceptable solubilizing cations for use with the present technology include alkali metals such as sodium and potassium, which are particularly preferred, and amines such as triethanolammonium, ammonium and morpholinium. Although, when used, the majority of the fatty acid should be incorporated into the formulation in neutralized salt form, it is often preferable to leave a small amount of free fatty acid in the formulation, as this can aid in the maintenance of product viscosity.

Primary alkyl sulfates are represented by the formula:

$$R^2OSO_3M$$

where $R^2$ is a primary alkyl group of 8 to 18 carbon atoms. M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperidinium cations and quaternary ammonium cations derived from alkylamines such as ethylamine, diethylamine, triethylamine, and mixtures thereof, and the like). The alkyl group $R^2$ may have a mixture of chain lengths. It is preferred that at least two-thirds of the $R^2$ alkyl groups have a chain length of 8 to 14 carbon atoms. This will be the case if $R^2$ is coconut alkyl, for example. The solubilizing cation may be a range of cations which are in general monovalent and confer water solubility. An alkali metal, notably sodium, is especially envisaged. Other possibilities are ammonium and substituted ammonium ions, such as trialkanolammonium or triallylammonium.

Alkyl ether sulfates are represented by the formula:

$$R^3O(CH_2CH_2O)_nSO_3M$$

where $R^3$ is a primary alkyl group of 8 to 18 carbon atoms, n has an average value in the range from 1 to 6 and M is a solubilizing cation. The alkyl group $R^3$ may have a mixture of chain lengths. It is preferred that at least two-thirds of the $R^3$ alkyl groups have a chain length of 8 to 14 carbon atoms. This will be the case if $R^3$ is coconut alkyl, for example. Preferably n has an average value of 2 to 5. Ether sulfates have been found to provide viscosity build in certain of the formulations of the present technology, and thus are considered a preferred ingredient.

Other suitable anionic surfactants that can be used are alkyl ester sulfonate surfactants including linear esters of $C_8$-$C_{20}$ carboxylic acids (i.e., fatty acids) which are sulfonated with gaseous $SO_3$ according to "The Journal of the American Oil Chemists Society", 52 (1975), pp. 323-329. Suitable starting materials would include natural fatty substances as derived from tallow, palm oil, etc.

The preferred alkyl ester sulfonate surfactants, especially for laundry applications, comprise alkyl ester sulfonate surfactants of the structural formula:

$$R^3-CH(SO_3M)-C(O)-OR^4$$

where $R^3$ is a $C_8$-$C_{20}$ hydrocarbyl, preferably an alkyl or combination thereof $R^4$ is a $C_1$-$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$-$C_{16}$ alkyl, and $R^4$ is methyl, ethyl or isopropyl. Especially preferred are the methyl ester sulfonates where $R^3$ is $C_{10}$-$C_{16}$ alkyl.

Fatty acid ester sulfonates are represented by the formula:

$$R^4CH(SO_3M)CO_2R^5$$

where $R^4$ is an alkyl group of 6 to 16 atoms, $R^5$ is an alkyl group of 1 to 4 carbon atoms and M is a solubilizing cation. The group $R^4$ may have a mixture of chain lengths. Preferably at least two-thirds of these groups have 6 to 12 carbon atoms. This will be the case when the moiety $R^4CH(-)CO_2(-)$ is derived from a coconut source, for instance. It is preferred that $R^5$ is a straight chain alkyl, notably methyl or ethyl.

Alkyl benzene sulfonates are represented by the formula:

$$R^6ArSO_3M$$

where $R^6$ is an allyl group of 8 to 18 carbon atoms, Ar is a benzene ring ($-C_6H_4-$) and M is a solubilizing cation. The group $R^6$ may be a mixture of chain lengths. A mixture of isomers is typically used, and a number of different grades, such as "high 2-phenyl" and "low 2-phenyl" are commercially available for use depending on formulation needs. A plentitude of commercial suppliers exist for these materials, including Stepan (Northfield, Ill.) and Witco (Greenwich, Conn.) Typically they are produced by the sulfonation of alkylbenzenes, which can be produced by either the HF-catalyzed alkylation of benzene with olefins or an $AlCl_3$-catalyzed process that alkylates benzene with chloroparaffins, and are sold by, for example, Petresa (Chicago, Ill.) and Sasol (Austin, Tex.). Straight chains of 11 to 14 carbon atoms are usually preferred.

Paraffin sulfonates having about 8 to about 22 carbon atoms, preferably about 12 to about 16 carbon atoms, in the alkyl moiety, are contemplated for use here. They are usually produced by the sulfoxidation of petrochemically-derived normal paraffins. These surfactants are commercially available as, for example, Hostapur SAS from Clariant (Charlotte, N.C.).

Olefin sulfonates having 8 to 22 carbon atoms, preferably 12 to 16 carbon atoms, are also contemplated for use in the present compositions. The olefin sulfonates are further characterized as having from 0 to 1 ethylenic double bonds; from 1 to 2 sulfonate moieties, of which one is a terminal group and the other is not; and 0 to 1 secondary hydroxyl moieties. U.S. Pat. No. 3,332,880 contains a description of suitable olefin sulfonates, and is incorporated here by reference. Examples of specific surfactant species from that patent include the following:

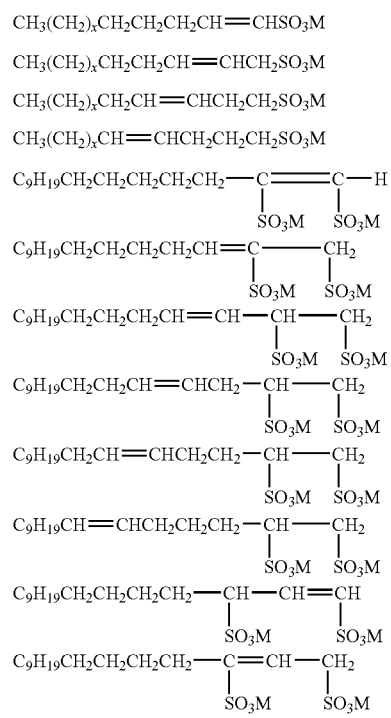

-continued $$C_9H_{19}CH_2CH_2CH_2CH=\underset{\underset{SO_3M}{|}}{C}-\underset{\underset{SO_3M}{|}}{CH_2}-CH_2$$

$$C_9H_{19}CH_2CH_2CH=CH\underset{\underset{SO_3M}{|}}{CH}-\underset{\underset{SO_3M}{|}}{CH_2}-CH_2$$

$$C_9H_{19}CH_2CH=CHCH_2-\underset{\underset{SO_3M}{|}}{CH}-\underset{\underset{SO_3M}{|}}{CH_2}-CH_2$$

$$CH_3(CH_2)_xCH_2CH_2CH(OH)CH_2CH_2SO_3M$$

$$CH_3(CH_2)_xCH_2CH(OH)CH_2CH_2CH_2SO_3M$$

$$CH_3(CH_2)_xCH(OH)CH_2CH_2CH_2CH_2SO_3M$$

$$C_9H_{19}CH_2CH_2CH_2CH=\underset{\underset{OH}{|}}{CH}-\underset{\underset{SO_3M}{|}}{CH}-\underset{\underset{SO_3M}{|}}{CH_2}$$

$$C_9H_{19}CH_2CH_2CH_2CHCH_2CH-\underset{\underset{SO_3M}{|}}{\underset{\underset{SO_3M}{|}}{CH_2}}$$ (with OH)

$$C_9H_{19}CH_2CH_2CHCH_2CH_2CH-CH_2$$ (OH, SO_3M, SO_3M)

$$C_9H_{19}CH_2CHCH_2CH_2CH_2CH-CH_2$$ (OH, SO_3M, SO_3M)

$$C_9H_{19}CH_2CH_2CH_2CH-CH-CH_2CH_2$$ (OH, SO_3M, SO_3M)

$$C_9H_{19}CH_2CH_2CHCH_2-CH-CH_2CH_2$$ (OH, SO_3M, SO_3M)

$$C_9H_{19}CH_2CHCH_2CH_2CH-CH_2-CH_2$$ (OH, SO_3M, SO_3M)

$$C_9H_{19}CHCH_2CH_2CH_2CH-CH_2CH_2$$ (OH, SO_3M, SO_3M)

$$C_9H_{19}CH_2CHCH_2CHCH_2CH_2CH_2$$ (OH, SO_3M, SO_3M)

$$C_9H_{19}CH_2CHCH_2CHCH_2CH_2CH_2$$ (SO_3M, OH, SO_3M)

$$C_9H_{19}CH_2CH_2CHCH_2CHCH_2CH_2$$ (SO_3M, OH, SO_3M)

$$C_9H_{19}CHCH_2CH_2CH_2CHCH_2CH_2$$ (SO_3M, OH, SO_3M)

In the preceding formulas, x is an integer of from about 4 to about 18, preferably from about 4 to about 12, and M represents any cation that forms a water-soluble salt such as alkali metals, e.g., sodium and potassium, and ammonium and substituted ammonium compounds, e.g., trialkylammonium and trialkylolammonium compounds. Specific examples of substituted ammonium compounds are triethylammonium, trimethylammonium, and triethanolammonium. Others will be apparent to those skilled in the art. Such materials are sold as, for example, Bio-Terge AS-40, which can be purchased from Stepan (Northfield, Ill.)

Sulfosuccinate esters represented by the formula:

$$R^7OOCCH_2CH(SO_3^-M^+)COOR^8$$

are also useful in the context of the present technology. $R^7$ and $R^8$ are alkyl groups with chain lengths of between 2 and 16 carbons, and may be linear or branched, saturated or unsaturated. A preferred sulfosuccinate is sodium bis(2-ethylhexyl)sulfosuccinate, which is commercially available under the trade name Aerosol OT from Cytec Industries (West Paterson, N.J.).

Organic phosphate based anionic surfactants include organic phosphate esters such as complex mono- or diester phosphates of hydroxyl-terminated alkoxide condensates, or salts thereof. Included in the organic phosphate esters are phosphate ester derivatives of polyoxyalkylated alkylaryl phosphate esters, of ethoxylated linear alcohols and ethoxylates of phenol. Also included are nonionic alkoxylates having a sodium alkylenecarboxylate moiety linked to a terminal hydroxyl group of the nonionic through an ether bond. Counterions to the salts of all the foregoing may be those of alkali metal, alkaline earth metal, ammonium, alkanolammonium and alkylammonium types.

Fatty acid ester sulfonates are represented by the formula:

$$R^9CH(SO_3M)CO_2R^{10}$$

where the moiety $R^9CH(-)CO_2(-)$ is derived from a coconut source and $R^{10}$ is either methyl or ethyl.

Another class of preferred anionic surfactants contemplated for the present purposes is the alkyl alkoxylated sulfate surfactants which are water soluble salts or acids of the formula $RO(A)_mSO_3M$ where R is an unsubstituted $C_{10}$-$C_{24}$ allyl or hydroxyalkyl group having a $C_{10}$-$C_{24}$ alkyl component, preferably a $C_{12}$-$C_{18}$ alkyl or hydroxyalkyl, more preferably $C_{12}$-$C_{15}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as allyl propoxylated sulfates are contemplated here. Specific examples of substituted ammonium cations include ethanol-, triethanol-, methyl-, dimethyl-, or trimethylammonium cations and quaternary ammonium cations such as tetramethyl-ammonium and dimethyl piperidinium cations and those derived from alkylamines such as ethylamine, diethylamine, triethylamine, mixtures thereof and the like. Exemplary surfactants are $C_{12}$-$C_{15}$ alkyl polyethoxylate (1.0) sulfate ($C_{12}$-$C_{15}$ E(1.0)M), $C_{12}$-$C_{15}$ allyl polyethoxylate (2.25) sulfate ($C_{12}$-$C_{15}$ E(2.25) M), $C_{12}$-$C_{15}$ alkyl polyethoxylate (3.0) sulfate ($C_{12}$-$C_{15}$ E(3.0)M), and $C_{12}$-$C_{15}$ alkyl polyethoxylate (4.0) sulfate ($C_{12}$-$C_{15}$ E(4.0)M), where M is conveniently selected from sodium and potassium.

Other anionic surfactants useful for detersive purposes can also be included in the detergent compositions of the present technology. These can include salts (including, for example, sodium, potassium, ammonium, and substituted ammonium salts such as mono-, di- and triethanolamine salts) of soap, $C_8$-$C_{22}$ primary of secondary alkanesulfonates, $C_8$-$C_{24}$ olefin sulfonates, sulfonated polycarboxylic acids prepared by sulfonation of the pyrolyzed product of alkaline earth metal citrates, e.g., as described in British patent specification No. 1,082,179, $C_8$-$C_{24}$ alkypolyglycolethersulfates (containing up to 10 moles of ethylene oxide); alkyl glycerol sulfonates, fatty acyl glycerol sulfonates, fatty oleoyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$-$C_{18}$ monoesters) and diesters of sulfosuccinates (especially saturated and unsaturated $C_6$-$C_{12}$ diesters), sulfates of alkylpolysaccharides such as the sulfates of alkylpolyglucoside (the nonionic non-sulfated compounds being described below), and alkyl polyethoxy carboxylates such as those of the formula $RO(CH_2CH_2O)_kCH_2COO$-M+ where R is a $C_8$-$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (incorporated here by reference), and Unilever U.S. Pat. No. 6,949,498 column 6, line 4 through column 8, line 30 (incorporated here by reference), from which much of the present discussion comes.

Other anionic surfactants contemplated for use with this formulation include isethionates, sulfated triglycerides, alcohol sulfates, ligninsulfonates, naphthelene sulfonates and alkyl naphthelene sulfonates and the like. Additional anionic surfactants, falling into the general definition but not specifically mentioned above, should also be considered within the scope of the present technology.

Specific anionic surfactants contemplated for use in the present compositions include alcohol ether sulfates (AES), linear alkylbenzene sulfonates (LAS), alcohol sulfates (AS), alpha methyl ester sulfonates (MES), or combinations of two or more of these. The amount of anionic surfactant contemplated can be, for example, 1% to 70% of the composition more preferably between 1% and 60%, even more preferably between 1% and 40%. For a more general description of surfactants, see P&G U.S. Pat. No. 5,929,022; column 3, 2nd paragraph through column 4, end of 1st paragraph (incorporated here by reference), from which much of the present discussion comes.

Cationic Surfactants

Specific cationic surfactants contemplated for use in the present compositions include ditallow dimethylammonium chloride (DTDMAC), fatty alkanolamides (FAA), and quaternized diesters of trialkanolamines and fatty acids. The proportions of cationic surfactants used in a formulation can range, for example, from 0.1% to 20%, more preferably between 1% and 10%, even more preferably between 1% and 5%. See also P&G U.S. Pat. No. 5,929,022; column 6, 2nd paragraph through column 7, 1st paragraph, from which much of the following discussion comes:

Cationic detersive surfactants suitable for use in the laundry detergent compositions of the present technology include those having one long-chain hydrocarbyl group. Examples of such cationic surfactants include the ammonium surfactants such as alkyldimethylammonium halogenides, and those surfactants having the formula:

$$[R^2(OR^3)_y][R^4(OR^3)_y]_2R^5N^+X^-$$

where $R^2$ is an alkyl or alkyl benzyl group having from about 8 to about 18 carbon atoms in the alkyl chain, each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$-$C_4$ alkyl, $C_1$-$C_4$ hydroxyalkyl, benzyl ring structures formed by joining the two $R^4$ groups, —$CH_2CHOH$—$CH(OH)C(O)R^6CH(OH)CH_2OH$ where $R^6$ is any hexose or hexose polymer having a molecular weight less than about 1000, and hydrogen when y is not 0; $R^5$ is the same as $R^4$ or is an allyl chain where the total number of carbon atoms of $R^2$ plus $R^5$ is not more than about 18; each y is from 0 to about 10 and the sum of the y values is from 0 to about 15; and X is any compatible anion. The long chain cationic surfactant can also be the quaternized version of stearamidopropyl dimethylamine (e.g. stearamidopropyl trimethylamine chloride).

Preferred cationic surfactants are the water-soluble quaternary ammonium compounds useful in the present composition having the formula:

$$R^1R^2R^3R^4N^+X^-$$

where R1 is $C_8$-$C_{16}$ alkyl, each of $R^2$, $R^3$ and $R^4$ is independently $C_1$-$C_4$ alkyl, $C_1$-$C_4$ hydroxyalkyl, benzyl, or —$(C_2H_4O)_xH$ where x has a value from 1 to 5, and X is an anion. In an embodiment, not more than one of $R^2$, $R^3$ or $R^4$ is benzyl.

The preferred alkyl chain length for $R^1$ is $C_{12}$-$C_{15}$, particularly where the alkyl group is a mixture of chain lengths derived from coconut or palm kernel fat or is derived synthetically by olefin build up or OXO alcohols synthesis. Preferred groups for $R^2$, $R^3$, and $R^4$ are methyl and hydroxyethyl groups and the anion X may be selected from halide, methosulphate, acetate and phosphate ions.

Examples of suitable quaternary ammonium compounds for use here are:

hexadecyl trimethyl ammonium chloride, also known as cetrimonium chloride, sold commercially as Ammonyx® CETAC by Stepan Co.;

coconut trimethyl ammonium chloride or bromide;

coconut methyl dihydroxyethyl ammonium chloride or bromide;

decyl triethyl ammonium chloride;

decyl dimethyl hydroxyethyl ammonium chloride or bromide;

$C_{12-15}$ dimethyl hydroxyethyl ammonium chloride or bromide;

coconut dimethyl hydroxyethyl ammonium chloride or bromide;

myristyl trimethyl ammonium methyl sulphate;

lauryl dimethyl benzyl ammonium chloride or bromide;

lauryl dimethyl (ethenoxy)4 ammonium chloride or bromide;

choline esters of formula $$R^1R^2R^3R^4N^+X^-$$

where $R^1$ is —$CH_2$—O—C(O)—($C_{12-14}$ alkyl) and $R^2$, $R^3$, and $R^4$ are methyl; and combinations of these.

Other cationic surfactants useful here are also described in U.S. Pat. No. 4,228,044, Cambre, issued Oct. 14, 1980, incorporated herein by reference.

Nonionic Surfactants

Examples of suitable nonionic surfactants include alkyl polyglucosides ("APGs"), alcohol ethoxylates, nonylphenol ethoxylates, and others. The nonionic surfactant may be used as from 1% to 90%, more preferably from 1 to 40% and most preferably between 1% and 32% of a detergent composition. Other suitable nonionic surfactants are described in P&G U.S. Pat. No. 5,929,022; column 4, 2nd paragraph through column 6, end of 1st paragraph, from which much of the following discussion comes:

One class of nonionic surfactants useful in the practice of the present technology are condensates of ethylene oxide with a hydrophobic moiety to provide a surfactant having an average hydrophilic-lipophilic balance (HLB) in the range from 8 to 17, preferably from 9.5 to 14, more preferably from 12 to 14. The hydrophobic (lipophilic) moiety may be aliphatic or aromatic in nature and the length of the polyoxyethylene group which is condensed with any particular hydrophobic group can be readily adjusted to yield a water-soluble compound having the desired degree of balance between hydrophilic and hydrophobic elements.

For "low HLB" nonionics, low HLB can be defined as having an HLB of 8 or less and preferably 6 or less. a "low level" of co-surfactant can be defined as 6% or less of the HDL and preferably 4% or less of the HDL.

Especially preferred nonionic surfactants of this type are the $C_9$-$C_{15}$ primary alcohol ethoxylates containing 3-12 moles of ethylene oxide per mole of alcohol, particularly the $C_{12}$-$C_{15}$ primary alcohols containing 5-8 moles of ethylene oxide per mole of alcohol. One suitable example of such a surfactant is polyalkoxylated aliphatic base, sold for example as Makon® NF-12 by Stepan Co.

Another class of nonionic surfactants comprises alkyl polyglucoside compounds of general formula $$RO\text{—}(C_nH_{2n}O)_tZ_x$$

where Z is a moiety derived from glucose; R is a saturated hydrophobic alkyl group that contains from 12 to 18 carbon atoms; t is from 0 to 10 and n is 2 or 3; x is an average value from 1.3 to 4, the compounds including less than 10% unreacted fatty alcohol and less than 50% short chain alkyl polyglucosides. Compounds of this type and their use in detergent compositions are disclosed in EP-B 0 070 077, EP 0 075 996 and EP 0 094 118.

Very suitable as nonionic surfactants are poly hydroxy fatty acid amide surfactants of the formula $$R^2\text{—}C(O)\text{—}N(R^1)\text{—}Z$$

where $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or alkenyl chain such as coconut alkyl or mixtures thereof, and Z is derived from a reducing sugar such as glucose, fructose, maltose, lactose, in a reductive amination reaction.

Highly preferred nonionics are amine oxide surfactants. The compositions of the present technology may comprise amine oxide in accordance with the general formula:

$$R^1(EO)_x(PO)_y(BO)_zN(O)(CH_2R')_2 \cdot H_2O$$

In general, it can be seen that the preceding formula provides one long-chain moiety $R^1(EO)_x(PO)_y(BO)_z$ and two short chain moieties, —$CH_2R'$. R' is preferably selected from hydrogen, methyl and —$CH_2OH$. In general $R^1$ is a primary or branched hydrocarbyl moiety which can be saturated or unsaturated, preferably, $R^1$ is a primary alkyl moiety. When x+y+z=0, $R^1$ is a hydrocarbyl moiety having a chain length of from about 8 to about 18. When x+y+z is different from 0, $R^1$ may be somewhat longer, having a chain length in the range $C_{12}$-$C_{24}$. The general formula also encompasses amine oxides where x+y+z=0, $R^1$ is $C_8$-$C_{18}$, R' is H and q=from 0 to 2, preferably 2. These amine oxides are illustrated by $C_{12-14}$ alkyldimethyl amine oxide, hexadecyl dimethylamine oxide, octadcylamine oxide and their hydrates, especially the dihydrates as disclosed in U.S. Pat. Nos. 5,075,501 and 5,071,594, which are incorporated herein by reference.

The presently described technology also encompasses amine oxides where x+y+z is different from zero, specifically x+y+z is from about 1 to about 10, and R' is a primary alkyl group containing about 8 to about 24 carbons, preferably from about 12 to about 16 carbon atoms. In these embodiments y+z is preferably 0 and x is preferably from about 1 to about 6, more preferably from about 2 to about 4; EO represents ethyleneoxy; PO represents propyleneoxy; and BO represents butyleneoxy. Such amine oxides can be prepared by conventional synthetic methods, e.g., by the reaction of alkylethoxysulfates with dimethylamine followed by oxidation of the ethoxylated amine with hydrogen peroxide.

Highly preferred amine oxides here are solids at ambient temperature, more preferably they have melting-points in the range 30° C. to 90° C. Amine oxides suitable for use here are made commercially by a number of suppliers, including Akzo Chemie, Ethyl Corp., and Procter & Gamble. See McCutcheon's compilation and Kirk-Othmer review article for alternate amine oxide manufacturers. Preferred commercially available amine oxides are the solid, dihydrate ADMOX 16 and ADMOX 18, ADMOX 12 and especially ADMOX 14 from Ethyl Corp.

Preferred embodiments include, for example, hexadecyldimethylamine oxide dihydrate, octa-decyldimethylamine oxide dihydrate, hexadecyltris(ethyleneoxy)dimethylamine oxide, and tetradecyldimethylamine oxide dihydrate.

In certain of the preferred embodiments in which $R^1$ is H, there is some latitude with respect to having R' slightly larger than H. Specifically, the presently described technology further encompasses embodiments where R'=$CH_2OH$, such as hexadecylbis(2-hydroxyethyl)amine oxide, tallowbis(2-hydroxyethyl)amine oxide, stearylbis(2-hydroxyethyl)amine oxide and oleylbis(2-hydroxyethyl)amine oxide.

Ampholytic Surfactants

Ampholytic synthetic detergents can be broadly described as derivatives of aliphatic or aliphatic derivatives of heterocyclic secondary and tertiary amines, in which the aliphatic radical may be straight chain or branched and where one of the aliphatic substituents contains from about 8 to about 18 carbon atoms and at least one contains an anionic water-solubilizing group, e.g., carboxy, sulfo, sulfato, phosphato, or phosphono (see U.S. Pat. No. 3,664,961, which provides specific examples of ampholytic surfactants from col. 6, line 60, to col. 7, line 53, incorporated here by reference). Examples of suitable ampholytic surfactants include fatty amine oxides and fatty amidopropylamine oxides. A specific suitable example is cocoamidopropyl betaine (CAPB) also known as coco betaine. Ampholytic surfactants can be used at a level from 1% to 50%, more preferably from 1% to 10%, even more preferably between 1% and 5% of the formulation, by weight.

Zwitterionic Surfactants

Zwitterionic synthetic detergents can be broadly described as derivatives of aliphatic quaternary ammonium and phosphonium or tertiary sulfonium compounds, in which the cationic atom may be part of a heterocyclic ring, and in which the aliphatic radical may be straight chain or branched, and where one of the aliphatic substituents contains from about 3 to 18 carbon atoms, and at least one aliphatic substituent contains an anionic water-solubilizing group, e.g., carboxy, sulfo, sulfato, phosphato, or phosphono. (see U.S. Pat. No. 3,664,961, which provides specific examples of zwitterionic surfactants from col. 7, line 65, to col. 8, line 75, incorporated here by reference). Zwitterionic surfactants can be used as from 1% to 50%, more preferably from 1% to 10%, even more preferably from 1% to 5% by weight of the present formulations.

Mixtures of Surfactants

Mixtures of any two or more individually contemplated surfactants, whether of the same type or different types, are contemplated herein.

Laundry Detergent Composition

The formulation and use of the present surfactants will now be illustrated in more detail for a laundry detergent composition.

Four desirable characteristics of a laundry detergent composition, in particular a liquid composition (although the present disclosure is not limited to a liquid composition, or to a composition having any or all of these attributes) are that (1) a concentrated formulation is useful to save on shelf space of a retailer, (2) a "green" or environmentally friendly composition is useful, (3) a composition that works in modern high efficiency washing machines which use less energy and less water to wash clothes than previous machines is useful, and (4) a composition that cleans well in lower temperature water for example less than 70° F.

To save a substantial amount of retailer shelf space, a concentrated formulation is contemplated having two or even three four, five, six, or even greater (e.g., 8×) times potency per unit volume or dose as conventional laundry detergents. The use of less water complicates the formulation of a detergent composition, as it needs to be more soluble and otherwise to work well when diluted in relatively little water.

To make a "green" formula, the surfactants should be ultimately biodegradable and non-toxic. To meet consumer perceptions and reduce the use of petrochemicals, a "green" formula may also advantageously be limited to the use of renewable hydrocarbons, such as vegetable or animal fats and oils, in the manufacture of surfactants.

High efficiency (HE) washing machines present several challenges to the detergent formulation. As of January 2011, all washing machines sold in the US must be HE, at least to some extent, and this requirement will only become more restrictive in the coming years. Front loading machines, all of which are HE machines, represent the highest efficiency, are increasingly being used.

Heavy duty liquid (HDL) detergent formulas are impacted by HE machines because the significantly lower water usage requires that less foam be generated during the wash cycle. As the water usage levels continue to decrease in future generations of HE machines, detergents may be required to transition to no foam. In addition, HE HDLs should also disperse quickly and cleanly at lower wash temperatures.

To work in a modern high efficiency washing machine, the detergent composition needs to work in relatively concentrated form in cold water, as these washing machines use relatively little water and cooler washing temperatures than prior machines. The sudsing of such high-efficiency formulations must also be reduced, or even eliminated, in a low-water environment to provide effective cleaning performance. The anti-redeposition properties of a high efficiency detergent formulation also must be robust in a low-water environment. In addition, formulations that allow the used wash water to be more easily rinsed out of the clothes or spun out of the clothes in a washing machine are also contemplated, to promote efficiency.

Liquid fabric softener formulations and "softergent" (fabric softener/detergent dual functional) single-add formulations also may need to change as water usage continues to decline in HE machines. A washer-added softener is dispensed during the rinse cycle in these machines. The present SE, PHSE, and HSE compositions provide some softening activity, which is contemplated to address these problems.

Laundry detergents and additives containing the presently described SE, PHSE, and HSE compositions are contemplated to provide high concentration formulations, or "green" formulations, or formulations that work well in high efficiency washing machines. Such detergents and additives are contemplated that have at least one of the advantages or desirable characteristics specified above, or combinations of two or more of these advantages, at least to some degree. The ingredients contemplated for use in such laundry detergents and additives are found in the following paragraphs.

In addition to the surfactants as previously described, a laundry detergent composition commonly contains other ingredients for various purposes. Some of those ingredients are also described below.

Builders and Alkaline Agents

Builders and other alkaline agents are contemplated for use in the present formulations.

Any conventional builder system is suitable for use here, including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders could also be used here.

Suitable polycarboxylate builders for use here include citric acid, preferably in the form of a water-soluble salt, and derivatives of succinic acid of the formula:

R—CH(COOH)CH$_2$(COOH)

where R is C$_{10\text{-}20}$ alkyl or alkenyl, preferably C$_{12\text{-}16}$, or where R can be substituted with hydroxyl, sulfo sulfoxyl or sulfone substituents. Specific examples include lauryl succinate, myristyl succinate, palmityl succinate 2-dodecenylsuccinate, or 2-tetradecenyl succinate. Succinate builders are preferably used in the form of their water-soluble salts, including sodium, potassium, ammonium and alkanolammonium salts.

Other suitable polycarboxylates are oxodisuccinates and mixtures of tartrate monosuccinic and tartrate disuccinic acid, as described in U.S. Pat. No. 4,663,071.

Especially for a liquid detergent composition, suitable fatty acid builders for use here are saturated or unsaturated Cl$_{10\text{-}18}$ fatty acids, as well as the corresponding soaps. Preferred saturated species have from 12 to 16 carbon atoms in the alkyl chain. The preferred unsaturated fatty acid is oleic acid. Another preferred builder system for liquid compositions is based on dodecenyl succinic acid and citric acid.

Some examples of alkaline agents include alkalic metal (Na, U, or NH$_4$) hydroxides, carbonates, bicarbonates. Another commonly used builder is borax.

For powdered detergent compositions, the builder or alkaline agent typically comprises from 1% to 95% of the composition. For liquid compositions, the builder or alkaline agent typically comprises from 1% to 60%, alternatively between 1% and 30%, alternatively between 2% and 15%. See U.S. Pat. No. 5,929,022; column 7, start of 2nd paragraph through column 7, end of 6th paragraph, from which much of the preceding discussion comes. Other builders are described in PCT Publ. WO 99/05242, which is incorporated here by reference.

Enzymes

The detergent compositions of the present technology may further comprise one or more enzymes, which provide cleaning performance and/or fabric, care benefits. Said enzymes include enzymes selected from cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, beta-glucanases, arabinosidases or mixtures thereof.

A preferred combination is a detergent composition having a cocktail of conventional applicable enzymes like protease, amylase, lipase, cutinase and/or cellulase in conjunction with the lipolytic enzyme variant D96L at a level of from 50 LU to 8500 LU per liter wash solution.

The cellulases usable in the present technology include both bacterial or fungal cellulase. Preferably, they will have a pH optimum of between 5 and 9.5. Suitable cellulases are disclosed in U.S. Pat. No. 4,435,307, Barbesgoard et al, which discloses fungal cellulase produced from *Humicola insolens*. Suitable cellulases are also disclosed in GB-A-2 075 028; GB-A-2 095 275 and DE-OS-2 247 832, which are incorporated herein by reference.

Examples of such cellulases are cellulases produced by a strain of *Humicola insolens* (*Humicola grisea* var. *thermoidea*), particularly the *Humicola* strain DSM 1800. Other suitable cellulases are cellulases originated from *Humicola insolens* having a molecular weight of about 50 KDa, an isoelectric point of 5.5 and containing 415 amino acids. Especially suitable cellulases are the cellulases having color care benefits. Examples of such cellulases are cellulases described in European patent application No. 91202879.2, filed Nov. 6, 1991 (Novo).

Peroxidase enzymes are used in combination with oxygen sources, e.g. percarbonate, perborate, persulfate, hydrogen peroxide, etc. They are used for "solution bleaching", i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813 and in European Patent application EP No. 91202882.6, filed on Nov. 6, 1991.

Said cellulases and/or peroxidases are normally incorporated in the detergent composition at levels from 0.0001% to 2% of active enzyme by weight of the detergent composition.

Preferred commercially available protease enzymes include those sold under the tradenames Alcalase®, Savinase®, Primase®, Durazym®, and Esperase® by Novo Nordisk A/S (Denmark), those sold under the tradename Maxatase®, Maxacal® and Maxapem® by Gist-Brocades, those sold by Genencor International, and those sold under the tradename Opticlean® and Optimase® by Solvay Enzymes. Other proteases are described in U.S. Pat. No. 5,679,630, issued Oct. 21, 1997 (P&G) can be included in the detergent composition of the present technology. Protease enzyme may be incorporated into the compositions in accordance with the present technology at a level of from about 0.0001% to about 2% active enzyme by weight of the composition.

A preferred protease here referred to as "Protease D" is a carbonyl hydrolase variant having an amino acid sequence not found in nature, which is derived from a precursor carbonyl hydrolase by substituting a different amino acid for the amino acid residue at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135, +156, +166, +195, +197, +204, +206, +210, +216, +217, +218, +222, +260, +265, and/or +274 according to the numbering of *Bacillus amyloliquefaciens* subtilisin, as described in the concurrently filed patent application of A. Baeck et al. entitled "Protease-Containing Cleaning Composition" U.S. Pat. No. 5,679,630, issued Oct. 21, 1997, which is incorporated here by reference in its entirety.

Highly preferred enzymes that can be included in the detergent compositions of the present technology include lipases. It has been found that the cleaning performance on greasy soils is synergistically improved by using lipases. Suitable lipase enzymes include those produced by microorganisms of the *Pseudomonas* group, such as *Pseudomonas stutzeri* ATCC 19.154, as disclosed in British Patent 1,372,034. Suitable lipases include those which show a positive immunological cross-reaction with the antibody of the lipase, produced by the microorganism *Pseudomonas fluorescens* IAM 1057. This lipase is available from Amano Pharmaceutical Co. Ltd., Nagoya, Japan, under the trade name Lipase P "Amano," hereafter referred to as "Amano-P". Further suitable lipases are lipases such as M1 Lipase®. and Lipomax®. (Gist-Brocades). Highly preferred lipases are the D96L lipolytic enzyme variant of the native lipase derived from *Humicola lanuginosa* as described in U.S. Pat. No. 6,017,871 issued Jan. 25, 2000 (P&G). Preferably the *Humicola lanuginosa* strain DSM 4106 is used. This enzyme is incorporated into the composition in accordance with the present technology at a level of from 50 LU to 8500 LU per liter wash solution. Preferably the variant D96L is present at a level of from 100 LU to 7500 LU per liter of wash solution. More preferably at a level of from 150 LU to 5000 LU per liter of wash solution.

By D96L lipolytic enzyme variant is meant the lipase variant as described in patent application WO 92/05249 viz. where the native lipase ex *Humicola lanuginosa* aspartic acid (D) residue at position 96 is changed to Leucine (L). According to this nomenclature said substitution of aspartic acid to Leucine in position 96 is shown as: D96L.

Also suitable are cutinases [EC 3.1.1.50] which can be considered as a special kind of lipase, namely lipases which do not require interfacial activation. Addition of cutinases to detergent compositions have been described in e.g. WO-A-88/09367 (Genencor).

The lipases and/or cutinases are normally incorporated in the detergent composition at levels from 0.0001% to 2% of active enzyme by weight of the detergent composition.

Amylases ($\alpha$ and/or $\beta$) can be included for removal of carbohydrate-based stains. Suitable amylases are Termamyl® (Novo Nordisk), Fungamyl® and BAN® (Novo Nordisk).

The above-mentioned enzymes may be of any suitable origin, such as vegetable, animal, bacterial, fungal and/or yeast origin. See U.S. Pat. No. 5,929,022; column 7, 7th paragraph through column 9, 6th paragraph, from which much of the preceding discussion comes. Preferred compositions optionally contain a combination of enzymes or a single enzyme, with the amount of each enzyme commonly ranging from 0.0001% to 2%.

Other enzymes and materials used with enzymes are described in PCT Publ. WO99/05242, which is incorporated here by reference.

Enzymes are expected to exhibit excellent shelf-life in SHP-containing HDLs. Not to be bound by theory, surfactants with low CMC values tend to be more mild to enzymes based on low monomer concentrations in solution which interfere with enzyme stability. The measured CMC, via the Wilhelmy plate technique, of SHP (produced according to Example 2 below) is 30 mg/L while that of the sodium salt of AES is 80 mg/L and NaLAS is 900 mg/L.

Adjuvants

The detergent compositions optionally contain one or more soil suspending agents or resoiling inhibitors in an amount from about 0.01% to about 5% by weight, alternatively less than about 2% by weight. Resoiling inhibitors include anti-redeposition agents, soil release agents, or combinations thereof. Examples of suitable agents are described in U.S. Pat. No. 5,929,022; column 10, 3rd paragraph through column 10, 5th paragraph, and include water-soluble ethoxylated amines having clay soil removal and anti-redeposition properties. Examples of such soil release and anti-redeposition agents given in the referenced patent include an ethoxylated tetraethylenepentamine. The ethoxylated amines further described in U.S. Pat. No. 4,597,898, VanderMeer, issued Jul. 1, 1986, are incorporated here by reference. Another group of preferred clay soil removal/anti-redeposition agents are the cationic compounds disclosed in European Patent Application 111,965, Oh and Gosselink, published Jun. 27, 1984, incorporated here by reference. Other clay soil removal/anti-redeposition agents which can be used include the ethoxylated amine polymers disclosed in European Patent Application 111,984, Gosselink published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985, all of which are incorporated here by reference.

Other clay soil removal and/or anti-redeposition agents known in the art can also be utilized in the compositions hereof. Another type of preferred anti-redeposition agent includes the carboxymethylcellulose (CMC) materials.

For example, optionally, anti-redeposition polymers can be incorporated into HDL formulations covered by the presently described technologies. In at least some embodiment, it is preferred to keep the level of anti-redeposition polymer below about 2%. It has been found that at levels above about 2%, anti-redeposition polymer may cause formulation instability (e.g. phase separation) and or undue thickening.

Soil release agents are also contemplated as optional ingredients in the amount of about 0.1% to about 5%. See U.S. Pat. No. 5,929,022; column 9, 8th paragraph through column 10, end of 1st partial paragraph.

Chelating agents in the amounts of about 0.1% to about 10%, more preferably about 0.5% to about 5% and even more preferably from about 0.8% to about 3% are also contemplated as an optional ingredient. See U.S. Pat. No. 5,929,022; column 10, 1st paragraph to column 10, end of 2nd paragraph.

Polymeric dispersing agents in the amount of 0% to about 6% are also contemplated as an optional component of the presently described detergent compositions. See U.S. Pat. No. 5,929,022; column 10, start of 7th paragraph to column 10, end of the continuing paragraph from that started on the previous column and is incorporated herein by reference.

A suds suppressor is also contemplated as an optional component of the present detergent composition, in the amount of from about 0.1% to about 15%, more preferably between about 0.5% to about 10% and even more preferably between about 1% to about 7%. See U.S. Pat. No. 5,929,022 column 11. The SE, PHSE, and HSE compositions described in this specification can also function as suds suppressants, alone or in combination with other suds suppressants.

Other ingredients that can be included in a liquid laundry detergent include perfumes, that optionally contain ingredients such as aldehydes, ketones, esters, and alcohols. More compositions that can be included are: carriers, hydrotropes, processing aids, dyes, pigments, solvents, bleaches, bleach activators and enzyme stabilizing packaging systems.

The co-surfactant technology of U.S. Pat. No. 4,561,998 can be used in conjunction with the present technology, for the reasons explained in that patent and is incorporated herein by reference. Co-surfactants and fatty acids identified in U.S. Pat. No. 4,561,998 that can be used in conjunction with anionic surfactants to improve laundering performance include, for example, chloride, bromide and methylsulfate $C_{8-16}$ alkyl trimethylammonium salts, $C_{8-16}$ alkyl di(hydroxyethyl)methylammonium salts, $C_{8-16}$ alkyl hydroxyethyldimethylammonium salts, and $C_{8-16}$ alkyloxypropyl trimethylammonium salts.

Similar to what is taught in U.S. Pat. No. 4,561,998, the compositions herein can also contain from about 0.25% to about 12%, preferably from about 0.5% to about 8%, more preferably from about 1% to about 4%, by weight of a cosurfactant selected from the group of certain quaternary ammonium, diquaternary ammonium, amine, diamine, amine oxide and di(amine oxide) surfactants. The quaternary ammonium surfactants are particularly preferred.

Quaternary ammonium surfactants can have the following formula:

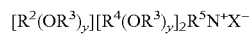

$$[R^2(OR^3)_y][R^4(OR^3)_y]_2R^5N^+X^-$$

wherein $R^2$ is an alkyl or alkyl benzyl group having from about 8 to about 18 carbon atoms in the alkyl chain; each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_{1-4}$ alkyl, $C_{1-4}$ hydroxyalkyl, benzyl, ring structures formed by joining the two $R^4$ groups, —$CH_2$ CHOHCHOHCOR$^6$CHOHCH$_2$ OH wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Preferred of the above are the alkyl quaternary ammonium surfactants, especially the mono-long chain alkyl surfactants described in the above formula when $R^5$ is selected from the same groups as $R^4$. The most preferred quaternary ammonium surfactants are the chloride, bromide and methylsulfate $C_{8-16}$ alkyl trimethylammonium salts, $C_{8-16}$ alkyl di(hydroxyethyl)methylammonium salts, $C_{8-16}$ alkyl hydroxyethyldimethylammonium salts, and $C_{8-16}$ alkyloxypropyl trimethylammonium salts. Of the above, decyl trimethylammonium methylsulfate, lauryl trimethylammonium chloride, myristyl trimethylammonium bromide and coconut trimethylammonium chloride and methylsulfate are particularly preferred.

U.S. Pat. No. 4,561,998 also provides that under cold water washing conditions, i.e., less than about 65° F. (18.3° C.), the $C_{8-10}$ alkyltrimethyl ammonium surfactants are particularly preferred since they have a lower Kraft boundary and, therefore, a lower crystallization temperature than the longer alkyl chain quaternary ammonium surfactants herein.

Diquaternary ammonium surfactants can be of the formula:

$$[R^2(OR^3)_y][R^4OR^3]_y]_2N^+R^3N^+R^5[R^4(OR^3)_y]_2(X^-)_2$$

wherein the $R^2$, $R^3$, $R^4$, $R^5$, y and X substituents are as defined above for the quaternary ammonium surfactants. These substituents are also preferably selected to provide diquaternary ammonium surfactants corresponding to the preferred quaternary ammonium surfactants. Particularly preferred are the $C_{8-16}$ alkyl pentamethylethylenediammonium chloride, bromide and methylsulfate salts.

Amine surfactants useful herein are of the formula:

$$[R^2(OR^3)_y][R^4(OR^3)_y]R^5N$$

wherein the $R^2$, $R^3$, $R^4$, $R^5$ and y substituents are as defined above for the quaternary ammonium surfactants. Particularly preferred are the $C_{12-16}$ alkyl dimethyl amines.

Diamine surfactants herein are of the formula

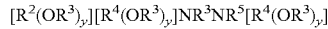

wherein the $R^2$, $R^3$, $R^4$, $R^5$ and y substituents are as defined above. Preferred are the $C_{12-16}$ alkyl trimethylethylene diamines.

Amine oxide surfactants useful herein are of the formula:

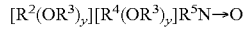

wherein the $R^2$, $R^3$, $R^4$, $R^5$ and y substituents are also as defined above for the quaternary ammonium surfactants. Particularly preferred are the $C_{12-16}$ alkyl dimethyl amine oxides.

Di(amine oxide) surfactants herein are of the formula:

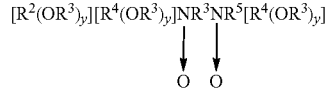

wherein the $R^2$, $R^3$, $R^4$, $R^5$ and y substituents are as defined above, preferably is $C_{12-16}$ alkyl trimethylethylene di(amine oxide).

Other common cleaning adjuncts are identified in U.S. Pat. No. 7,326,675, col. 12, and PCT Publ. WO 99/05242 (Pages 29-56). Such cleaning adjuncts are identified as including bleaches, bleach activators, suds boosters, dispersant polymers (e.g., from BASF Corp. or Rohm & Haas) other than those described above, color speckles, silvercare, anti-tarnish and/or anti-corrosion agents, pigments, dyes, fillers, germicides, hydrotropes, anti-oxidants, enzyme stabilizing agents, pro-perfumes, carriers, processing aids, solvents, dye transfer inhibiting agents, brighteners, structure elasticizing agents, fabric softeners, anti-abrasion agents, and other fabric care agents, surface and skin care agents. Suitable examples of such other cleaning adjuncts and levels of use are found in U.S. Pat. Nos. 5,576,282, 6,306,812 B1 and 6,326,348 B1 and PCT Publ. WO99/05242. All the patents identified in this paragraph are incorporated by reference for their further disclosures of adjuvants.

Fatty Acid

Similar to that disclosed in U.S. Pat. No. 4,561,998, the compositions of the present technology may contain from about 5% to about 40%, preferably from about 7% to about 30%, most preferably from about 10% to about 20%, by weight of a fatty acid containing from about 10 to about 22 carbon atoms. The fatty acid can also contain from about 1 to about 10 ethylene oxide units in the hydrocarbon chain.

Suitable fatty acids are saturated and/or unsaturated and can be obtained from natural sources such as plant or animal esters (e.g., palm kernel oil, palm oil, coconut oil, babassu oil, safflower oil, tall oil, castor oil, tallow and fish oils, grease, and mixtures thereof) or synthetically prepared (e.g., via the oxidation of petroleum or by hydrogenation of carbon monooxide via the Fisher-Tropsch process). Examples of suitable saturated fatty acids for use in the compositions of the present technology include, but are not limited to capric, lauric, myristic, palmitic, stearic, arachidic and behenic acid. Suitable unsaturated fatty acid species include: palmitoleic, oleic, linoleic, linolenic and ricinoleic acid. Examples of preferred fatty acids are saturated $C_{10}$-$C_{14}$ (coconut) fatty acids, from about 5:1 to about 1:1 (preferably about 3:1) weight ratio mixtures of lauric and myristic acid, and mixtures of the above lauric/myristic blends with oleic acid at a weight ratio of about 4:1 to about 1:4 mixed lauric/myristic:oleic.

U.S. Pat. No. 4,507,219 identifies various sulfonate surfactants as suitable for use with the above-identified co-surfactants. The disclosures of U.S. Pat. Nos. 4,561,998 and 4,507,219 with respect to co-surfactants are incorporated here by reference.

Softergent

Softergent technologies as described in, for example, U.S. Pat. Nos. 6,949,498, 5,466,394 and 5,622,925 can be used in compositions of the present technology. The term "softergent" refers to a softening detergent that can be dosed at the beginning of a wash cycle for the purpose of simultaneously cleaning and softening fabrics. The sulfonated estolides of fatty acids of the present technology can be used to make stable, aqueous heavy duty liquid laundry detergent compositions containing a fabric-softening agent that provide exceptional cleaning as well as fabric softening and anti-static benefits.

For example, a softergent composition of the present technology can contain about 0.5% to about 10%, preferably from about 2% to about 7%, more preferably from about 3% to about 5% by weight of a quaternary ammonium fabric-softening agent having the formula:

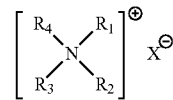

wherein $R_1$ and $R_2$ are individually selected from the group consisting of $C_1$-$C_4$ alkyl, $C_1$-$C_4$ hydroxy alkyl, benzyl, and —$(C_2H_4O)_xH$ where x has a value from 2 to 5; X is an anion; and (1) $R_3$ and $R_4$ are each a $C_8$-$C_{14}$ alkyl or (2) $R_3$ is a $C_8$-$C_{22}$ alkyl and $R_4$ is selected from the group consisting of $C_1$-$C_{10}$ alkyl, $C_1$-$C_{10}$ hydroxy alkyl, benzyl, and —$(C_2H_4O)_x$ H where x has a value from 2 to 5.

Preferred fabric-softening agents are the mono-long chain alkyl quaternary ammonium surfactants wherein the above formula $R_1$, $R_2$, and $R_3$ are each methyl and $R_4$ is a $C_8$-$C_{18}$ alkyl. The most preferred quaternary ammonium surfactants are the chloride, bromide and methylsulfate $C_{8-16}$ allyl trimethyl ammonium salts, and $C_{8-16}$ alkyl di(hydroxyethyl)-methyl ammonium salts. Of the above, lauryl trimethyl ammonium chloride, myristyl trimethyl ammonium chloride and coconut trimethylammonium chloride and methylsulfate are particularly preferred. For example, ADOGEN 412™, a lauryl trimethyl ammonium chloride commercially available from Witco, is a preferred softening agent.

Another class of preferred quaternary ammonium surfactants are the di-$C_8$-$C_{14}$ alkyl dimethyl ammonium chloride or methylsulfates; particularly preferred is di-$C_{12}$-$C_{14}$ alkyl dimethyl ammonium chloride. This class of materials is particularly suited to providing antistatic benefits to fabrics. Materials having two alkyl chain lengths longer than $C_{14}$, like di-$C_{16}$-$C_{18}$ alkyl dimethyl ammonium chloride, which are commonly used in rinse added fabric softeners, are not included in the presently described technology, since they do not yield isotropic liquid detergents when combined with the anionic surfactants described above.

A preferred softergent embodiment of the present technology comprises the detergent composition wherein the weight ratio of anionic surfactant component to quaternary ammonium softening agent is from about 3:1 to about 40:1 and a preferred range from about 5:1 to 20:1.

Odor Control

Odor control technologies as described in, for example, U.S. Pat. No. 6,878,695 can be used in compositions of the present technology.

For example, a composition containing one or more of the sulfonated estolides of fatty acids of the present technology can further comprise a low-degree of substitution cyclodextrin derivative and a perfume material. The cyclodextrin is preferably functionally-available cyclodextrin. The compositions can further comprise optional cyclodextrin-compatible and—incompatible materials, and other optional components. Such a composition can be used for capturing unwanted molecules in a variety of contexts, preferably to control malodors including controlling malodorous molecules on inanimate surfaces, such as fabrics, including carpets, and hard surfaces including countertops, dishes, floors, garbage cans, ceilings, walls, carpet padding, air filters, and the like, and animate surfaces, such as skin and hair.

The low-degree of substitution cyclodextrin derivatives useful in the present technology are preferably selected from low-degree of substitution hydroxyalkyl cyclodextrin, low-degree of substitution alkylated cyclodextrin, and mixtures thereof. Preferred low-degree of substitution hydroxyalkyl beta-cyclodextrins have an average degree of substitution of less than about 5.0, more preferably less than about 4.5, and still more preferably less than about 4.0. Preferred low-degree of substitution alkylated cyclodextrins have an average degree of substitution of less than about 6.0, more preferably less than about 5.5, and still more preferably less than about 5.0.

The compositions of the present technology can comprise a mixture of cyclodextrins and derivatives thereof such that the mixture effectively has an average degree of substitution equivalent to the low-degree of substitution cyclodextrin derivatives described hereinbefore. Such cyclodextrin mixtures preferably comprise high-degree of substitution cyclodextrin derivatives (having a higher average degree of substitution than the low-degree substitution cyclodextrin derivatives described herein) and non-derivatized cyclodextrin, such that the cyclodextrin mixture effectively has an average degree of substitution equivalent to the low-degree of substitution cyclodextrin derivative. For example, a composition comprising a cyclodextrin mixture containing about 0.1% non-derivatized beta-cyclodextrin and about 0.4% hydroxypropyl beta-cyclodextrin having an average degree of substitution of about 5.5, exhibits an ability to capture unwanted molecules similar to that of a similar composition comprising low-degree of substitution hydroxypropyl beta-cyclodextrin having an average degree of substitution of about 3.3. Such cyclodextrin mixtures can typically absorb odors more broadly by complexing with a wider range of unwanted molecules, especially malodorous molecules, having a wider range of molecular sizes preferably at least a portion of a cyclodextrin mixture is alpha-cyclodextrin and its derivatives thereof, gamma-cyclodextrin and its derivatives thereof, and/or beta-cyclodextrin and its derivatives thereof; more preferably a mixture of alpha-cyclodextrin, or an alpha-cyclodextrin derivative, and derivatized beta-cyclodextrin, even more preferably a mixture of derivatised alpha-cyclodextrin and derivatized beta-cyclodextrin; and most preferably a mixture of hydroxypropyl alpha-cyclodextrin and hydroxypropyl beta-cyclodextrin, and/or a mixture of methylated alpha-cyclodextrin and methylated beta-cyclodextrin.

The cavities within the functionally-available cyclodextrin in the compositions of the present technology should remain essentially unfilled (i.e. the cyclodextrin remains uncomplexed and free) or filled with only weakly complexing materials when in solution, in order to allow the cyclodextrin to absorb (i.e. complex with) various unwanted molecules, such as malodor molecules, when the composition is applied to a surface containing the unwanted molecules. Non-derivatized (normal) beta-cyclodextrin can be present at a level up to its solubility limit of about 1.85% (about 1.85 g in 100 grams of water) at room temperature. Beta-cyclodextrin is not preferred in compositions which call for a level of cyclodextrin higher than its water solubility limit. Non-derivatized beta-cyclodextrin is generally not preferred when the composition contains surfactant since it affects the surface activity of most of the preferred surfactants that are compatible with the derivatized cyclodextrins.

The level of low-degree of substitution cyclodextrin derivatives that are functionally-available in the odor control compositions of the present technology is typically at least about 0.001%, preferably at least about 0.01%, and more preferably at least about 0.1%, by weight of the composition. The total level of cyclodextrin in the present composition will be at least equal to or greater than the level of functionally-available cyclodextrin. The level of functionally-available will typically be at least about 10%, preferably at least about 20%, and more preferably at least about 30%, by weight of the total level of cyclodextrin in the composition.

Concentrated compositions can also be used. When a concentrated product is used, i.e., when the total level of cyclodextrin used is from about 3% to about 60%, more preferably from about 5% to about 40%, by weight of the concentrated composition, it is preferable to dilute the concentrated composition before treating fabrics in order to avoid staining. Preferably the concentrated cyclodextrin composition is diluted with about 50% to about 6000%, more preferably with about 75% to about 2000%, most preferably with about 100% to about 1000% by weight of the concentrated composition of water. The resulting diluted compositions have usage concentrations of total cyclodextrin and functionally-available cyclodextrin as discussed hereinbefore, e.g., of from about 0.1% to about 5%, by weight of the diluted composition of total cyclodextrin and usage concentrations of functionally-available cyclodextrin of at least about 0.001%, by weight of the diluted composition.

Forms

The HDL compositions of the present technology can take any of a number of forms and any of the different delivery systems that are currently known or to be developed in the future such as ready-to-use, dilutable, wipes, etc.

For example, the compositions of the present technology can take the form of a dilutable fabric detergent or conditioner, that may be an isotropic liquid, a surfactant-structured liquid, a granular, spray-dried or dry-blended powder, a tablet, a paste, a molded solid, a water soluble sheet, or any other laundry detergent form known to those skilled in the art. A "dilutable" fabric detergent or conditioning composition is defined, for the purposes of this disclosure, as a product intended to be used by being diluted with water or a non-aqueous solvent by a ratio of more than 100:1, to produce a liquor suitable for treating textiles. "Green concentrate" compositions like those on the market today for Fantastic®, Windex® and the like, can be formulated such that they could be a concentrate to be added to a bottle for final reconstitution.

The compositions of the present technology could also be formulated as a gel or a gel packet like the dishwasher products on the market today. Water soluble sheets or sachets, such as those described in U.S. Pat. Appl. No. 20020187909, which is incorporated herein by reference, are also envisaged as a potential form of the present technology. These may be sold under a variety of names, and for a number of purposes. The composition can also be deposited on a wiper or other substrate.

Polymeric Suds Enhancers

In accordance with some embodiments, polymeric suds enhancers such as those described in U.S. Pat. No. 6,903,064 can be used in compositions of the present technology. For example, the detergent compositions of the present technology may further comprises an effective amount of polymeric suds volume and suds duration enhancers. These polymeric materials provide enhanced suds volume and suds duration during cleaning.

One example of a polymeric suds stabilizer suitable for use in a composition of the present technology is selected from the group consisting of:

(i) a polymer comprising at least one monomeric unit having the formula:

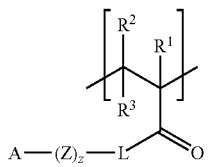

wherein each of $R^1$, $R^2$ and $R^3$ are independently selected from the group consisting of hydrogen, $C_1$ to $C_6$ alkyl, and mixtures thereof; L is O; Z is $CH_2$; z is an integer selected from about 2 to about 12; A is $NR^4R^5$, wherein each of $R^4$ and $R^5$ is independently selected from the group consisting of hydrogen, $C_1$ to $C_8$ alkyl, and mixtures thereof, or $NR^4R^5$ form an heterocyclic ring containing from 4 to 7 carbon atoms, optionally containing additional hetero atoms, optionally fused to a benzene ring, and optionally substituted by $C_1$ to $C_8$ hydrocarbyl;

(ii) a proteinaceous suds stabilizer having an isoelectric point form about 7 to about 11.5;

(iii) a zwitterionic polymeric suds stabilizer; and (iv) mixtures thereof.

Preferably, the exemplary polymeric suds stabilizer described above has a molecular weight of from about 1,000 to about 2,000,000 daltons and more preferably the molecular weight is about 5,000 to about 1,000,000.

Methods of Laundering Fabrics

Methods for laundering fabrics with SE, PHSE, or HSE-based formulations are contemplated. Such methods involve placing fabric articles to be laundered in a high efficiency washing machine or a regular (non-high efficiency) washing machine and placing an amount of the SE, PHSE, or HSE-based composition sufficient to provide a concentration of the composition in water of from about 0.001% to about 5% by weight when the machine is operated in a wash cycle. A high efficiency machine is defined by the Soap and Detergent Association as any machine that uses 20% to 66% of the water, and as little as 20%-50% of the energy, of a traditional, regular agitator washer (SDA "Washers and Detergents" publication 2005; http://www.cleaning101.com/laundry/HE.pdf. The wash cycle is actuated or started to launder the fabric articles.

EXAMPLES

The compositions and processes described here, and ways to make and use them are illustrated by the following examples. Examples stated in the present or future tense are not represented as having been carried out.

Example 1

Preparation of SE Sulfonic Acid

The fatty acid feedstock used was derived from a vegetable oil source. For the purpose of sulfonation, the feedstock had an equivalent weight of about 270.6, as determined by iodine value. The feedstock was comprised of about 80% C-18:1, about 12.5% C-18:2, and about 7.5% saturated fatty acids, as measured by area count data obtained by gas chromatography using a flame ionization detector.

The feedstock was sulfonated on a falling film reactor using a feedstock temperature of about 15° C., an air/$SO_3$ temperature of about 40° C., a sulfonator jacket temperature of about 42° C., and a molar ratio of $SO_3$ to alkene functionality of about 1.0. After passing through a degassing unit, the acid produced from the sulfonation reaction was collected in small glass jars, frozen in an ice bath, and then stored in a freezer until further processing.

Analysis of Acid: The carboxylic acid content in the SE sulfonic acid product was determined by dissolving an aliquot of product in water that contained sufficient KOH to afford a solution with a pH greater than about 10.5. Titration of the solution with aqueous HCl indicated a free carboxylate content of about 2.04 milliequivalents per gram of sulfonated acid (meq/g). The sulfonic acid product was analyzed for carboxylic ester content by subjecting an aliquot of the acid to exhaustive alkaline hydrolysis conditions and then analyzing for carboxylate content. To accomplish this hydrolysis, an aliquot of product that was dissolved in dilute aqueous KOH was then digested for about 16 hours in an 85° C. oven, ensuring that the pH of the solution remained above about 10.5, and was then titrated with aqueous HCl. The carboxylate content, on the basis of starting sulfonic acid product mass, was thereby determined to be about 3.18 meq/g. The change in carboxylate content upon hydrolysis is attributable to the hydrolysis of carboxylic esters. Therefore, the amount of carboxylic ester functionality was found to be about 36 mol percent of the total carboxylic functionality (carboxylic acid+carboxylic ester) present in the SE sulfonic acid product. $^1H$ and $^{13}C$ NMR spectra of the acid product dissolved in $CDCl_3$ displayed signals that are consistent with the structure of alpha-sulfo-estolide functionality. In addition, $^1H$ NMR spectral data indicated that the SE sulfonic acid composition was further comprised of approximately 10 mol % of internal gamma sultones (1,3 diallyl 1,3 sultones) relative to the total carboxylic functionality (carboxylic acid+ester).

Example 2

Preparation of Potassium Salts of SHP

The fatty acid feedstock used in this example had an equivalent weight of about 280 and was derived from a tallow source that typically affords fatty acids comprising about 70% C18:1, about 12% polyunsaturated acid, and about 10-15% saturated fatty acid. The feedstock was sulfonated on a film reactor using a molar ratio of $SO_3$ to alkene functionality of about 0.91. The sulfonic acid produced from the sulfonator was continuously neutralized in a loop reactor with aqueous KOH to produce a neutralized material that, when titrated to bromophenol blue endpoint with aqueous HCl, was analyzed as containing about 2.5% free alkalinity (base value, expressed in terms of wt. % KOH). If measured, the pH of this material, diluted in water, would be in the range of about 5.5 to about 7.5. The neutralized material was charged to a batch reactor and was then maintained at 60-65° C. in order to hydrolyze sultones, as well as any potential sulfonic acid esters and anhydrides that may be present in the material. During the hydrolysis, the base value was maintained in the range of about 1.5 to about 1.8%. The hydrolysis reaction was continued until base value remained constant. The pH of the final sultone hydrolyzed product (SHP) was about 5.6 to about 5.9. The solids level in the product was measured by gravimetric changes upon drying in a 105° C. oven and was found to be about 54% by weight. $^1$H NMR spectroscopy of an aliquot of the SHP indicated essentially complete hydrolysis of sultones and the presence of internal hydroxyalkane sulfonate groups that result from the hydrolysis of 1,3 dialkyl 1,3 sultones.

The SHP was characterized in terms of free carboxylic acid and potassium carboxylate functionality by titration with aqueous HCl. Titration of the product, as produced, indicated a carboxylate salt content of 0.25 milliequivalents per gram (meq/g). Titration of an aliquot that had been first adjusted to pH>10 with KOH indicated a carboxylate salt content of 0.78 meq/g. The difference between these two titration results corresponded to the unneutralized carboxylic acid content within the product, the calculated result being 0.53 meq/g. The carboxylic ester content within the product was then determined by first hydrolyzing the ester functionality at elevated temperature using excess caustic. To accomplish this hydrolysis, a 15 gram aliquot of product was mixed with 3 grams of 45% aqueous KOH in a vial and the resulting solution was digested in an 85° C. oven for several hours until measured carboxylate meq/g was observed to be constant. The change in carboxylate meq/g upon hydrolysis, correcting for dilution of the sample upon addition of caustic, was taken to be a quantitative measure of the carboxylic ester content in the product. Based on this process, the ester content was found to be 0.56 meq/g. Since the total amount of carboxylic acid, carboxylate salt, and carboxylic ester was found to add up to 1.34 meq/g, the molar percentage of fatty acid functionality in the composition that was present as carboxylic ester was calculated to be 42%.

The product was further characterized by $^1$H, $^{13}$C and 2D NMR spectroscopic methods on a JEOL ECA 500 spectrometer. A sample of the product was adjusted to pH 10 to ensure that all carboxylic acid functionality was converted to carboxylate salt form. An aliquot of this sample was then dried under vacuum to afford a semi-solid residue that was dissolved in $D_2O$. Quantitative $^{13}$C NMR spectroscopy demonstrated two sets of carbonyl carbons, in the ranges of about 184 to about 183 ppm and about 175 to about 173 ppm, corresponding to carboxylate (COO—K+) and carboxylic ester (COO-alkyl) functionality, respectively. The integrations of these two sets of peaks were in an approximate 6:4 ratio, respectively, consistent with approximately 40% of all carboxylic functionality in the product being present as carboxylic esters. 2D experiments provided evidence in both $^1$H and $^{13}$C spectra for the presence of substantial amounts alpha-sulfo-estolide functionality within the product mixture.

LC/MS" was used to further characterize the reaction product. Chromatographic separation on a reverse phase column revealed the presence of multiple components in the reaction product. Mass spectral data on some of these separated components provided evidence for the presence of sulfonated compounds that may be viewed as being comprised of two fatty acid chains, as well as sulfonated compounds that may viewed as being comprised of three fatty acid chains.

Examples 3-5

Preparation of Potassium Salts of SHP

In these examples, an oleic fatty acid feedstock was used that was derived from a vegetable oil source. For the purpose of sulfonation, the feedstock had an equivalent weight of about 274.6, as determined by iodine value. The feedstock was comprised of about 78% C-18:1, about 12% C-18:2, and about 9% saturated fatty acids.

For Example 3, the feedstock was sulfonated on a film reactor at a molar ratio of $SO_3$ to alkene functionality of 0.95 to produce SE sulfonic acid. This acid was continuously neutralized in a loop reactor with 45 percent (wt/wt) aqueous KOH (caustic) at a SE acid to caustic mass ratio of about 0.822 to about 0.178. The neutralized material that was collected off of the loop reactor was then subjected to a sultone hydrolysis step by maintaining the liquid at 85° C. for 16 hours.

For Examples 4 and 5, the feedstock was sulfonated on a film reactor at a molar ratio of $SO_3$ to alkene functionality of 0.70 and 0.50, respectively, to produce SE sulfonic acids that were collected in small glass jars, frozen in an ice bath, and then stored in a freezer until further processing. Thawed acids were converted to SHP by mixing SE acid with aqueous KOH in a batch reaction to afford neutralized salts solutions, followed by hydrolysis of sultones at 85° C. for 4 hours.

The SHP products obtained in these examples were analyzed for ester content as follows. Total meq/g of carboxylic acid and carboxylate salt in SHP was determined by titration of a sample, adjusted to pH>11, with 0.1 N HCl. Total meq/g of carboxylic acid, carboxylate salt, and carboxylic ester in SHP was determined by 0.1 N HCl titration of a sample that had been exhaustively hydrolyzed with excess KOH at 85° C. for 16 hours. The mole percentage of total carboxylic functionality that was present as carboxylic esters in the SHP was then calculated.

In addition, the SHP was analyzed by $^1$H NMR spectroscopy in terms of a molar amount of specific internal alkene sulfonate functionality that is characterized by proton signal at ppm, and specific internal hydroxyalkane sulfonate functionality that is characterized by proton signals at 4.1 and 3.9 ppm relative to total carboxylic functionality. Results are summarized in Table 1.

TABLE 1

|  | Example 3 | Example 4 | Example 5 |
|---|---|---|---|
| molar ratio of $SO_3$ to alkene functionality | 0.95 | 0.70 | 0.50 |
| wt fraction SE sulfonic acid in neutralization | 0.677 | 0.446 | 0.448 |
| wt fraction 45% aq. KOH in neutralization | 0.323 | 0.166 | 0.166 |
| wt fraction additional water in neutralization | 0 | 0.388 | 0.386 |
| pH (2 percent SHP solution (wt/wt) in $H_2O$) | 7.1 | 6.6 | 7.9 |

TABLE 1-continued

|  | Example 3 | Example 4 | Example 5 |
|---|---|---|---|
| percent solids (gravimetric, 105° C. oven for 2 hours) | 77.7 | 50.4 | 50.9 |
| Ester Content (mole percent carboxylic esters relative to total carboxylic functionality) | 49.5 | 38.9 | 31.9 |
| moles internal 2-alkene sulfonate units per mole total carboxylic functionality[a] | 0.17 | 0.17 | 0.11 |
| moles internal 2-hydroxyalkane sulfonate per mole total carboxylic functionality[b] | 0.07 | 0.04 | 0.02 |

Notes:
a. Internal 2-alkene sulfonate functional units may be comprised of compounds of the following formula, wherein Q and Q' are alkylene segments meant to designate the location of the functional unit as "internal" in a hydrocarbon chain, such as in a fatty carboxylic acid or ester chain:

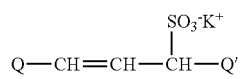

b. Internal 2-hydroxyalkane sulfonate functional units may be comprised of compounds the formula, wherein Q and Q' are alkylene segments meant to designate the location of the functional unit as "internal" in a hydrocarbon chain, such as in a fatty carboxylic acid or ester chain:

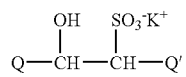

Examples 6-9

Preparation of Potassium Salts of SHP from Mixtures of Oleic Acid with Saturated Fatty Acids In these examples, which are summarized in Table 5, mixtures of unsaturated and saturated fatty acids were subjected to the sequential process steps of sulfonation with $SO_3$ on a film reactor to produce SE sulfonic acid, continuous neutralization of the sulfonic acid in a loop reactor, and hydrolysis of sultones in a batch reactor to produce SHP. The saturated fatty acids were incorporated to function as chain termination agents in the esterification reactions that may otherwise lead to substantial levels of oligomeric products such as compositions of Formula 1 where n=2 or more. In the sulfonation step, the feedstock temperature of about 25° C., an air/$SO_3$ temperature of about 41° C., a sulfonator jacket temperature of about 25° C.

The oleic fatty acid used to prepare the fatty acid mixtures had an equivalent weight for the purpose of sulfonation of about 274.6, as determined by an iodine value of 92.4, and was comprised of about 78% C-18:1, about 12% C-18:2, and about 9% saturated fatty acids. The coconut fatty acid used to prepare the fatty acid mixtures in Examples 6, 7, and 8 had an iodine value of 2.1, and was comprised of approximately 8% C-8, 6% C-10, 51% C-12, 19% C-14, 9% C-16, and 3% C-18 saturated fatty acids. The capric acid used to prepare the fatty acid mixture in Example 9 had an iodine value of about 0.2 and was comprised of about 99% C10 saturated fatty acid.

The SHP samples produced were analyzed for carboxylic ester content as described in Examples 3-5. The SHP of Example 7 was further analyzed in terms of gravimetric analysis of petroleum ether extractables (PEX) that were extracted from aqueous ethanol solutions at approximately pH 3. These gravimetric analyses were conducted on separate aliquots before and then after a step of exhaustive ester hydrolysis that was conducted by means of incubation with excess KOH at 85° C. for 16 hours. The change in PEX before and after ester hydrolysis was then used to calculate an estimated degree of incorporation of non-sulfonated fatty acids into the SHP, as summarized in Table 2. $^1$H NMR analyses of the PEX samples indicated that both extracts consisted essentially of about 90 mol percent saturated fatty acid and about 10 mol percent monounsaturated fatty acid. This result confirmed that of a significant level (roughly 40 percent) of the coconut fatty acid (chain termination agent) was incorporated into the SHP as carboxylic esters.

TABLE 2

|  | Example 6 | Example 7 | Example 8 | Example 9 |
|---|---|---|---|---|
| Chain Termination Agent | Coconut Fatty Acid | Coconut Fatty Acid | Coconut Fatty Acid | Capric Acid |
| weight fraction of vegetable oleic acid in fatty acid feedstock | 0.80 | 0.68 | 0.68 | 0.65 |
| weight fraction of Chain Termination Agent in fatty acid feedstock | 0.20 | 0.32 | 0.32 | 0.35 |
| molar ratio of $SO_3$ to alkene functionality | 0.95 | 0.95 | 0.75 | 0.95 |
| wt fraction SE sulfonic acid in neutralization | 0.303 | 0.260 | 0.338 | 0.301 |
| wt fraction 45% aq. KOH in neutralization | 0.124 | 0.130 | 0.136 | 0.133 |
| wt fraction additional water in neutralization | 0.573 | 0.610 | 0.525 | 0.566 |
| pH (2 percent SHP solution (wt/wt) in $H_2O$ | 6.6 | 8.5 | 6.7 | 6.7 |
| percent solids (gravimetric, 105° C. oven for 2 hours) | 34.9 | 31.0 | 34.6 | 33.9 |
| Ester Content (mole percent carboxylic esters relative to total carboxylic functionality) | 36.6 | 33.5 | 30.2 | 29.1 |
| weight percent petroleum ether extractables in SHP (wt/wt total solids) |  | 18.76 |  |  |

TABLE 2-continued

|  | Example 6 | Example 7 | Example 8 | Example 9 |
|---|---|---|---|---|
| weight percent petroleum ether extractables after exhaustive ester hydrolysis (wt/wt total solids, corrected for dilution with caustic) |  | 31.61 |  |  |
| Percentage of non-sulfonated fatty acids that was incorporated into SHP as carboxylic esters |  | 40.7 |  |  |

Example 10

Ester Hydrolysis of SHP with Excess KOH to Produce EHP

An approximately 54% solids solution of the potassium salts of SHP, was prepared as described in Example 2. To a small vial was added about 15.0 g of this product and about 3.0 g of about 45 wt. % aqueous potassium hydroxide, which corresponded to a roughly 1.5 times the amount of caustic required to neutralize free carboxylic acids and to hydrolyzed carboxylic esters in the SHP. The contents of the vial were thoroughly mixed and then the vial was sealed and placed in an 85° C. oven for about 16 hours. Upon cooling, the obtained EHP was homogenous, was free of precipitation or solids, and was a highly flowable liquid. NMR analysis of the EHP indicated that there was no detectable carboxylic acid ester functionality, as judged by a lack of $^{13}C$ signals for ester carbonyl and by a lack of $^{1}H$ and $^{13}C$ signals that had been identified in the starting material as being consistent with alpha-sulfo estolide functionality. In addition, $^{1}H$ NMR data indicated hydroxyalkane sulfonate functionality that is signatured by a signal at about 3.9 ppm and that results from the hydrolysis of sulfo-estolide functional groups, at a level of about 38 mol percent relative to total carboxylic functionality. The spectroscopic analysis of the EHP was consistent with the product comprising a mixture of saturated and unsaturated monomeric fatty acid carboxylates, alkene sulfonate-functionalized fatty acid carboxylates, and hydroxy sulfonate-functionalized fatty acid carboxylates.

Example 11

Ester Hydrolysis of SHP to Produce EHP

To a quart (1-liter) jar was added about 788 g of the SHP Example 2 and about 109.2 g of 45 wt. % aqueous KOH, which corresponded to a molar amount of KOH necessary to: (a) neutralized all free carboxylic acids in the SHP; and (b) to hydrolyzed the carboxylic esters in the SHP with 1.05 molar equivalents of free caustic. The contents were thoroughly mixed and then the jar was sealed and placed in an approximately 85° C. oven for about 40 hours. Upon cooling, the obtained EHP was homogeneous, free of precipitation or solids, and was a highly flowable liquid. The EHP was analyzed by titration with aqueous HCl and was found to comprise about 1.17 meq/g of potassium carboxylate. Based on the mass balance from the reagent charges for the ester hydrolysis reaction and the change in carboxylate content, the degree of ester hydrolysis was calculated to be about 98.6 mol percent. At this level of ester hydrolysis, the carboxylic ester content in the EHP was calculated to about 0.6 mol percent of total carboxylic functionality in the EHP.

Example 12

Partial Ester Hydrolysis of SHP to Produce PEHP

To a quart (1-liter) jar was added about 824 g of the SHP of Example 2 and about 82.5 g of 45 wt. % aqueous KOH, which corresponded to a molar amount of KOH necessary to: (a) neutralized all free carboxylic acid; and (b) to hydrolyzed a portion of the carboxylic esters in the SHP with 0.50 molar equivalents of free caustic. The contents were thoroughly mixed and then the jar was sealed and placed in an approximately 85° C. oven for about 24 hours. Upon cooling, the obtained PEHP was homogeneous, free of precipitation or solids, and was a highly flowable liquid. The PEHP was analyzed by titration with aqueous HCl and was found to comprise about 0.96 meq/g of potassium carboxylate. Based on the mass balance from the reagent charges for the ester hydrolysis reaction and the change in carboxylate content, the degree of ester hydrolysis was calculated to be about 50.5 mol percent. At this level of ester hydrolysis, the carboxylic ester content in the PEHP was calculated to about 21 mol percent of total carboxylic functionality in the PEHP.

Example 13

Partial Ester Hydrolysis of SE Sulfonic Acid with Water to Produce PEHP Sulfonic Acid SE sulfonic acid was obtained under conditions comparable to the sulfonation step of Example 3. This acid was found to comprise about 30 mol % carboxylic esters relative to total carboxylic functionality, as determined by the methods of titration as described in Example 1. To a 2 ounce jar was added about 15 g of the SE sulfonic acid and about 3.75 g of water. The contents were thoroughly mixed and then the jar was sealed and placed in an approximately 85° C. oven for about 14 hours. The resulting PEHP sulfonic acid was found to comprise about 18 mol % carboxylic esters relative to total carboxylic functionality. It is thereby observed that about 40 percent of the carboxylic esters present in starting SE sulfonic acid had been hydrolyzed. In addition, $^{1}H$ NMR spectroscopy indicated that about 80 percent of the sultones present in the starting SE sulfonic acid had been hydrolyzed in the PEHP sulfonic acid. The PEHP sulfonic acid could be subsequently processed in all methods and processing steps that are suitable and are presently described for the processing of SE sulfonic acid.

Example 14

Preparation of a Bleached Aqueous Concentrate of SHP Potassium Salts

The feedstock used in this example had an equivalent weight of about 274.6 and was comprised of about 78% C-18:1, about 12% C-18:2, and about 9% saturated fatty acids. The feedstock was sulfonated on a falling film reactor at a rate of about 129.3 lbs per hour using a molar ratio of $SO_3$ to alkene functionality of about 0.95. The SE sulfonic acid was continuously neutralized in a loop reactor with concurrent addition of about 51.1 lbs per hour of 45% aqueous KOH and about 46.5 lbs per hour of water. The temperature of the reaction mixture in the loop reactor was about 85° C. Neutralized SE solution was continuously fed from the loop reactor to an in-line mixer, where about 4.9 lbs per hour of 50% aqueous hydrogen peroxide was homogenized into the solution, which was about pH 5.5. This reaction mixture was then fed to a stirred tank reactor. After collecting about 60 gallons of reaction mixture, concurrent sultone hydrolysis and bleaching were continued at about 80° C. for about 4 additional hours, adding additional 45% aqueous KOH as necessary to maintain the pH of the reaction mixture in the range of about 5.2 to about 6.2. The SHP produced from this reaction was at a pH of about 6.2, was comprised of about 70.5% solids and about 0.5% (wt/wt) active peroxide, and had a Klett color at 1 percent solids concentration of 20.

Example 15A-D

Impact of pH on Bleaching of SHP with Hydrogen Peroxide

An approximately 73% solids solution of SHP was produced from vegetable oil-derived oleic acid (equivalent weight of about 274.6) by sulfonation on a film reactor at a molar ratio of $SO_3$ to alkene functionality of about 0.95, neutralization with aqueous KOH with a loop reactor, and sultone hydrolysis in a batch reactor. The SHP was obtained at a pH of about 5.25, measured at a concentration of 2 wt % of SHP solution diluted with deionized water. Color was measured on solutions of 5 wt % of SHP solution diluted with deionized water using a Klett-Summerson photoelectric colorimeter equipped with a 4 cm pathlength glass cell. The Klett color of the diluted unbleached SHP at was 729. pH of the SHP was adjusted to several different values by the addition of 45% aqueous KOH. Bleaching of the SHP was conducted at about 85° C. using 3 percent active $H_2O_2$ (wt/wt), provided to the reaction mixture in the form of 35% aqueous $H_2O_2$. pH values of the bleaching reaction mixtures were observed to drift slightly downward by about 0.2 to about 0.4 pH units. Results from the bleaching reactions are summarized in Table 3. The reaction corresponding to entry 15-D demonstrated a rapid decomposition of hydrogen peroxide, as evidenced by severe and rapid foaming of the reaction mass. This result demonstrates the importance of maintaining pH below a level necessary to minimize hydrogen peroxide decomposition, so to prevent severe foaming of the reaction mixture.

TABLE 3

| | Entry | | | |
|---|---|---|---|---|
| | 15-A | 15-B | 15-C | 15-D |
| Initial pH (measured at 2 wt % SHP diluted in $H_2O$) | 5.25 | 6.2 | 6.5 | 6.9 |
| Bleached SHP Klett color (5 wt % solids in $H_2O$) | 105 | 93 | 93 | Not measured |
| Extent of reaction foaming (% volume expansion) | <5 | <5 | ~50 | >100: Foamed out of reactor |

Examples 16-17

Influence of pH on the Physical Stability of SHP Solutions

The influence of pH on the physical stability of SHP at ambient conditions (approximately 22° C.) was assessed by means of visual observation and measurement of sample turbidity. For the purposes of these examples, a physically stable sample was defined as a material that was a clear, homogeneous liquid product, free of precipitation of solids or separation of two or more fluid phases, as could be confirmed in terms of a turbidity reading of less than 20 NTU. Sample turbidity was measured on un-diluted samples using a HF Scientific Micro 100 Laboratory Turbidimeter equipped with a 30 mL cuvette. Samples were prepared by adjusting pH with aqueous KOH, as indicated in Table 4. pH was measured on 2 wt % SHP solutions diluted with de-ionized water. The results in Table 4 demonstrate that the physical stability of SHP samples can be improved by adjusting the pH to a value that is above, or alternatively below, a range of pH values that otherwise may result in physical separation and inhomogeneity of the product.

TABLE 4

| Example 16 SHP of Example 15 prior to bleaching: ~73% solids | | | Example 17 SHP of Example 8 ~35% Solids | | |
|---|---|---|---|---|---|
| pH | Appearance | Turbidity (NTU) | pH | Appearance | Turbidity (NTU) |
| 5.3 | Clear | 0.7 | 6.1 | Clear | 2.6 |
| 6.2 | Opaque, with precipitation | 550 | 6.7 | Opaque, with precipitation | >1000 |
| 6.9 | Opaque, with precipitation | >1000 | 9.0 | Clear | 9.0 |
| 7.8 | Opaque, with precipitation | >1000 | | | |
| 8.3 | Clear | 0.6 | | | |

Example 18

Peroxide Beaching of Aqueous Concentrate of SHP Potassium Salts Followed by pH Adjustment to Improve Physical Stability The 73% solids solution of SHP was that was described in Example 15, prior to bleaching, was used in this example. To a 1 liter jacketed glass reactor equipped with overhead mechanical stirrer was added about 510 g of SHP that had been adjusted with 45% aqueous KOH to a pH of about 6.0, measured at 2 percent (wt/wt) of SHP diluted in deionized water. Upon heating the SHP to about 80° C., about 30.6 g of 50% aqueous $H_2O_2$ was added. A manageable amount of peroxide decomposition was noted as evidenced by modest foaming and an approximately 3-4° C. exotherm. The reaction mixture was then maintained at about 85° C. for 4 hours and then aliquots of 45% aqueous KOH were added incrementally every 10 minutes in order to slowly adjust the pH of the reaction mixture towards higher values. Samples of reaction mixture were collect for analysis of color and peroxide concentration, and for assessment of physical stability upon cooling. Results are summarized in Table 5. These results demonstrate that an upward adjustment of pH following bleaching of SHP can be used to facilitate peroxide decomposition. Further, these results demonstrate that when such processing action is taken for high solids SHP, it is preferable to adjust pH to a level that is sufficient to afford a product that remains homogeneous upon cooling to ambient storage conditions.

TABLE 5

| pH (2% SHP diluted in $H_2O$) | Klett color (5% SHP diluted in $H_2O$) | Peroxide concentration (ppm $H_2O_2$) | Product appearance after 16 hrs at 22° C. |
|---|---|---|---|
| 5.7[a] | 47 | 4100 | Clear, homogeneous |
| 6.3 | | 3200 | Opaque, fatty acid precipitation |
| 7.6 | 45 | 146 | Opaque, fatty acid precipitation |
| 8.4 | 50 | 82 | Slightly turbid, homogeneous |

[a]after 4 hrs of bleaching at 85° C. and prior to incremental KOH additions.

Alternatively to the exemplified process of reducing peroxide in the bleached SHP by addition of KOH, the bleaching reaction mixture could be treated with a reducing agent such as $SO_2$, sulfuric acid, or metal salts thereof, in order to substantially reduce the amount of residual peroxide in the bleached material. Optionally, the reduced peroxide product could be adjusted in pH either downward or upward to produce a product that remains homogeneous upon storage at ambient temperatures.

Examples 19-22

Bleaching of SE Sulfonic Acid with Aqueous Hydrogen Peroxide

SE sulfonic acid was obtained under conditions comparable to the sulfonation step of Example 3. The color of this acid was measured to be 618 Klett at a 1 wt. % concentration in methanol on a LICO colorimeter, using an 11 mm diameter cylindrical cuvette. Samples of the SE sulfonic acid were mixed with 3.5% active hydrogen peroxide (wt/wt), provided to the reaction mixture in the form of 50% aqueous $H_2O_2$, together with varying levels of additional water. The samples were then digested in an approximately 50° C. oven, and Klett color was monitored as a function of time. Results are summarized in Table 6. These data indicate that a substantial reduction of SE sulfonic acid color is realized by bleaching with aqueous hydrogen peroxide and that there is substantial benefit to conducting this bleaching in the presence of additional added water.

TABLE 6

| | Example 19 | Example 20 | Example 21 | Example 22 |
|---|---|---|---|---|
| Percent additional water in acid mixture[a] | 0 | 3 | 6 | 9 |
| Time | Klett Color (1% acid in methanol) | | | |
| 30 minutes | 127 | 100 | 101 | 111 |
| 60 minutes | 125 | 96 | 83 | 79 |
| 90 minutes | 117 | 87 | 75 | 72 |
| 120 minutes | 111 | 79 | 68 | 62 |

[a]in addition to water provided from 50% aqueous $H_2O_2$.

Example 23

Preparation of SHP from Partially Bleached SE Sulfonic Acid

SE sulfonic acid was obtained under conditions comparable to the sulfonation step of Example 3. The color of this acid was measured to be 630 Klett at a 1 wt. % concentration in methanol on a LICO calorimeter, using an 11 mm diameter cylindrical cuvette.

In a first reaction sequence (Table 7, Entry 23-A), the SE sulfonic acid was bleached for 15 minutes at 50° C. with 3.5 percent active hydrogen peroxide (wt/wt), provide to the reaction mixture in the form of 35% aqueous $H_2O_2$, in the presence of an additional 5.2 percent (wt/wt) of water. The bleached acid was then was neutralized, adding aqueous KOH to obtain a solution with a pH of about 6.5. The temperature of the reaction mixture was then increased to 80° C. and additional aqueous KOH was added in increments over 2 hours so as to maintain the reaction mixture between about pH 6.5 to about pH 7.0. The reaction mixture was then maintained at 80° C. for an additional 2 hours to produce an SHP of approximately 50% solids.

In a second reaction sequence (Table 7, Entry 23-B), the same reaction sequence used for Entry 23-A was used, except that additional 35% hydrogen peroxide (0.82% active peroxide wt/wt on acid) was added 1 hour into the incremental aqueous KOH addition and then again upon completion of the incremental aqueous KOH addition.

In a third reaction sequence (Table 7, Entry 23-C), non-bleached SE sulfonic acid was neutralized with aqueous KOH to obtain a solution with a pH of about 6.5. The temperature of the reaction mixture was increased to 80° C., and then 3.5 percent active hydrogen peroxide (wt/wt relative to SE sulfonic acid) was added in the form of 35% aqueous $H_2O_2$. Additional aqueous KOH was added in increments over 2 hours so as to maintain the reaction mixture between about pH 6.5 to about pH 7.0. Additional 35% hydrogen peroxide (0.82% active peroxide wt/wt on acid) was added 1 hour into the incremental aqueous KOH addition and then again upon completion of the incremental aqueous KOH addition. The reaction mixture was maintained at 80° C. for an additional 2 hours to produce an SHP of approximately 50% solids. The Klett color values of the bleached SHP samples produced were measured on 5% solids aqueous solutions using a Klett-Summerson photoelectric calorimeter equipped with a 4 cm path length glass cell.

Results are summarized in Table 7. These results indicate that an improved SHP color can be achieved through the use of acid bleaching, particularly when, upon neutralization of the acid, additional hydrogen peroxide is provided during subsequent sultone hydrolysis processing.

TABLE 7

| Entry | Process | Klett Color (5% Solids in $H_2O$) |
|---|---|---|
| 23-A | Acid bleaching, no additional $H_2O_2$ provided after neutralization or during sultone hydrolysis | 155 |
| 23-B | Acid bleaching, neutralization, and additional incremental additions of $H_2O_2$ provided during sultone hydrolysis | 80 |
| 23-C | No acid bleaching, $H_2O_2$ after neutralization with incremental additions of $H_2O_2$ provided during sultone hydrolysis | 198 |

Example 24

Preparation of SE from a Mixture of Unsaturated Triglyceride and a Saturated Fatty Acid The feedstock used in this example was a mixture of 58 percent (wt/wt) commercial soybean oil (refined, bleached, de-gummed) and 42 percent (wt/wt) octanoic acid. For the purpose of sulfonation, the equivalent weight of the feedstock mixture was 277 grams per mole of unsaturation. The molar ratio of octanoic acid to unsaturation in the feedstock mixture was about 0.8. About 17.5 g of the feedstock was diluted in about 40 mL of pentane and the resulting solution was then sulfonated by bubbling through the liquid about 4.06 g of gaseous $SO_3$ diluted in $N_2$ (about 0.8 moles $SO_3$ per mole of unsaturation) while maintaining the reaction temperature in the range of about 0 to 5° C. The reaction mass was then stripped of pentane under vacuum and was then maintained at about 20° C. for 18 hours. Titration of the obtained SE sulfonic acid with 0.14 N NaOH in water indicated a carboxylic acid content of 1.92 milli-equivalents per gram. Based on this result relative to the mole balance of reagents used, the degree of octanoic acid that was incorporated into the product as carboxylic esters was calculated to be about 18 mole percent relative to the initial charge of octanoic acid.

Example 25

Foaming Reduction

The SHP of Example 2 was used in this example. The materials listed in Tables 11 and 12 were tested for foaming under the conditions stated in the table.

TABLE 8

| | Chicago Tap Water | | w/Castor Oil | |
|---|---|---|---|---|
| Component* | Height (mL) after 5 seconds | Height (mL) after 5 minutes | Height (mL) after 5 seconds | Height (mL) after 5 minutes |
| Neodol 25-7 | 260 | 250 | 177.5 | 145 |
| Neodol 25-9 | 250 | 245 | 175 | 125 |
| SHP | 130 | 100 | 100 | 100 |
| NaLAS | 500+ | 500+ | 200 | 200 |
| 50%-50% SHP-NaLas | 225 | 225 | 195 | 195 |
| Steol CS-370 | 390 | 380 | 305 | 300 |
| Steol CS-270 | 397.5 | 382.5 | 307.5 | 305 |
| MES C16 | 220 | 142.5 | 157.5 | 135 |

TABLE 9

| | Chicago Tap Water | | w/Castor Oil | |
|---|---|---|---|---|
| Component | Height (mL) After 5 seconds | Height (mL) After 5 minutes | Height (mL) After 5 seconds | Height (mL) After 5 minutes |
| LAS | 500+ | 500+ | 200 | 200 |
| AES-3EO | 390 | 380 | 305 | 300 |
| AES-2EO | 397.5 | 382.5 | 307.5 | 305 |
| AB C12-C15-7EO | 260 | 250 | 177.5 | 145 |
| AE C12-C15-9EO | 250 | 245 | 175 | 125 |
| 50%-50% LAS & SHP | 225 | 225 | 195 | 195 |
| MES C16 | 220 | 142.5 | 157.5 | 135 |
| SHP | 130 | 100 | 100 | 100 |

In Tables 8 and 9, Neodol 25-7 is an alcohol ethoxylate $C_{12}$-$C_{15}$ chain length with 7 moles of ethylene oxide (Shell Chemicals, Houston, Tex.); Neodol 25-9 is an alcohol ethoxylate $C_{12}$-$C_{15}$ chain length with 9 moles of ethylene oxide; NaLAS is linear alkylbenzene sulfonic acid, sodium salt; Steol® CS-370 is sodium laureth sulfate 3-mole ethylene oxide (Stepan Company, Northfield, Ill.); Steol® CS-270 is sodium laureth sulfate 2-mole ethylene oxide; MES C16 is a C16 methyl ester sulfonate Tables 8 and 9 demonstrate that SHP exhibits significantly lower foaming (from 10 to 90% lower) than many of the major surfactants employed in laundry detergents currently available on the market. SHP also lowered the foaming of other surfactants when combined with them as shown in the 50:50 sample of Example 1 with LAS. The 50:50 Example 1:LAS sample showed a 50% decrease in foam height compared to LAS alone.

Example 26

SHP as a Builder Solubilizer

The SHP of Example 2 was used in this example. A high efficiency base formula was used for analysis. The formula with SHP had sodium carbonate levels increased until there was no longer a clear/homogeneous solution. The same was carried out with sodium LAS and sodium AES separately in the high efficiency base line formula. These results show that SHP solubilizes sodium carbonate at a higher amounts (from 20-80% more) than both LAS and AES while maintaining a clear/homogeneous liquid. Specifically, this data shows that SHP possesses the ability to solubilize sodium carbonate by 25% higher amount than either LAS or AES at room temperature, and 50% higher amount at elevated temperatures (40° C.).

Example 27

Interaction of SHP, PEHP, and EHP Compositions with Cationic Agents

Although the SE, PHSE, or HSE-based compositions are anionic surfactants, they show less tendency to couple with cationic surfactants than conventional anionic surfactants used in cleaning products, for example, LAS.

Procedure: the compositions described in Table 10 are made according to the following steps:

Add the water and trisodium citrate and mix until the solution is clear.

Add BIO-SOFT® N25-9 little by little until the solution is homogeneous.

Add BIO-SOFT® N25-3 and mix until the solution is homogeneous.

The final solution is cloudy.

Add the hydrotrope and mix until solution is clear.

To determine the coupling ability vs. sodium linear alkyl benzene sulfonate (NaLAS), sodium xylene sulfonate (SXS) and the SHP of Example 2, measure the amount of hydrotrope needed to clear the solution.

TABLE 10

| Formula | Agent % actives | with SXS % actives | with LAS % actives |
|---|---|---|---|
| Bio-soft N25-9 (HLB 13) | 5 | 5 | 5 |
| Bio-Soft N25-3 (HLB 8) | 5 | 5 | 5 |
| trisodium citrate*2H$_2$O | 1 | 1 | 1 |
| hydrotrope requirement (actives) | 6.2 | 5.3 | 8.3 |
| Final appearance | clear solution | clear solution | did not clear, just got thicker |

Examples 28A-G

SLA Supplemental Laundry Detergent Examples

Examples 28A-G refer to the following seven experiments:
A. Cleaning: SHP of Example 3 versus LAS
B. Cleaning: SHP of Example 7 versus LAS
C. Cleaning: C12EO2 co-surfactant
D. Cleaning: Amine oxide co-surfactant
E. Thickening with polymers
F. High surfactant concentrates
G. Ability to modify rheology (thin) concentrated MES surfactant systems For cleaning experiments A-D, 60 g of heavy duty liquid (HDL) was added to 90 F water in a high efficiency (HE) Whirlpool Duet Sport machine on Normal setting (54 minutes full cycle). Two runs per HDL, with 4 stain cloths per run, were carried out. Experimental stain cloths employed used include: dust/sebum on cotton, grass on cotton and spaghetti sauce on cotton (purchased from scientific Services, Sparrow Bush, N.Y.); and, WFK-10C and EMPA106 (purchased from Testfabrics, West Pittston, Pa.). Each wash also included 6 pounds of cotton, pillowcase ballast. At the end of each wash, the stain cloth were static dried and then L, a, b readings taken on a HunterLab LabScan XE spectrophotometer. L, a, b readings are also taken of the clean, unsoiled cotton fabric from which each stain was applied. Cleaning was then calculated by the following equation (as reported in the literature— Neiditch, O. W., et al, *Journal of the American Oil Chemist's Society*, December, 1980, 426):

$$SRI = 100 - \sqrt{(L_{clean} - L_{washed})^2 + (a_{clean} - a_{washed})^2 + (b_{clean} - b_{washed})^2}$$

where the SRI is the Stain Removal Index.

Example 28A

In this example, the cleaning benefits of the SHP of Example 3 are demonstrated. The following HDL composition, in Table 11, was formulated with SHP:

TABLE 11

| | % Inclusion (100% active) | |
|---|---|---|
| Ingredient | Comparative Formula 1 | A |
| SHP of Example 3 | | 15.0 |
| sodium linear alkylbenzene sulfonate | 15.0 | |
| C$_{12-15}$EO$_7$* | 5.0 | 5.0 |
| Monoethanolamine | 1.0 | 1.0 |
| Triethanolamine | 1.0 | 1.0 |
| Sodium Citrate | 1.0 | 1.0 |
| Water | 77.0 | 77.0 |
| pH | 10.0 | |

*BIO-SOFT ® N25-7, Stepan Company, Northfield, IL.

Comparative Formula 1 gave an SRI value of 92.9 on spaghetti sauce while Formula A gave a value of 94.7. This indicates that the SHP-containing formula cleans better than the LAS formula on this difficult to remove stain and that the SHP acts as a good cleaning agent when employed in a laundry detergent application.

Example 28B

In this example, the cleaning benefits of the SHP of Example 7 are demonstrated.

The following HDL composition in Table 12 was formulated with SHP:

TABLE 12

| | % Inclusion (100% active) | |
|---|---|---|
| Ingredient | Comparative Formula 2 | B |
| SHP of Example 7 | | 15.0 |
| sodium linear alkylbenzene sulfonate | 15.0 | |
| C$_{12-15}$EO$_7$* | 5.0 | 5.0 |
| Monoethanolamine | 1.0 | 1.0 |
| Triethanolamine | 1.0 | 1.0 |
| Sodium Citrate | 1.0 | 1.0 |
| Water | 77.0 | 77.0 |
| pH | 10.0 | |

*BIO-SOFT ® N25-7, Stepan Company, Northfield, IL.

Cleaning results were shown in Table 13 below:

TABLE 13

| | SRI | |
|---|---|---|
| Stain Cloth | Comparative Formula 2 | B |
| Spaghetti sauce on cotton | 92.9 | 94.9 |
| Dust/sebum on cotton | 81.4 | 83.0 |

These results demonstrate that the SHP formula gives better cleaning results than the analogous LAS formula on both spaghetti sauce and dust/sebum on cotton.

Example 28C

In this example, the cleaning benefit of adding a low HLB nonionic co-surfactant is demonstrated.

The following HDL compositions in Table 14 was formulated with and without $C_{12}EO_2$:

TABLE 14

| | % Inclusion (100% active) | |
|---|---|---|
| Ingredient | Formula C | Formula D |
| SHP of Example 3 | 10.0 | 10.0 |
| $C_{12-15}EO_7$* | 10.0 | 6.0 |
| $C_{12}EO_2$** | 0.0 | 4.0 |
| Monoethanolamine | 1.0 | 1.0 |
| Triethanolamine | 1.0 | 1.0 |
| Sodium Citrate | 1.0 | 1.0 |
| Sodium xylene sulfonate | 2.0 | 2.0 |
| Water | 75.0 | 75.0 |

*BIO-SOFT ® N25-7, Stepan Company, Northfield, IL.
**BIO-SOFT ® AE-2, Stepan Company, Northfield, IL.

Cleaning results are shown in Table 15 below:

TABLE 15

| | SRI | |
|---|---|---|
| Stain Cloth | Formula C | Formula D |
| WFK-10C | 82.2 | 84.1 |
| Grass on cotton | 78.9 | 80.5 |
| Spaghetti sauce on cotton | 92.8 | 95.4 |
| Dust/sebum on cotton | 82.1 | 82.5 |

These results demonstrate that although Formula C is already a good cleaning detergent, use of a low HLB nonionic co-surfactant in place of some of the higher HLB nonionic as done in Formula D renders cleaning even better. Although use of a low HLB nonionic co-surfactant is not required to achieve excellent cleaning benefits, its use at a low level is preferred.

Example 28D

In this example, the cleaning benefit of adding an amine oxide or cationic co-surfactant is demonstrated.

Formulas E and F shown in Table 16 were created by modifying Formula A:

TABLE 16

| | % Inclusion | |
|---|---|---|
| Ingredient | E | F |
| SHP of Example 3 | 13.0 | 13.0 |
| lauryl dimethylamine oxide* | 2.0 | |
| cetyl trimethyl ammonium chloride** | | 2.0 |
| $C_{12-15}EO_7$*** | 5.0 | 5.0 |
| Monoethanolamine | 1.0 | 1.0 |
| Triethanolamine | 1.0 | 1.0 |

TABLE 16-continued

| | % Inclusion | |
|---|---|---|
| Ingredient | E | F |
| Sodium Citrate | 1.0 | 1.0 |
| Water | 77.0 | 77.0 |

*AMMONYX ® LO
**AMMONYX ® CETAC 30
***BIO-SOFT ® N25-7 - all from Stepan Company, Northfield, IL.

Cleaning results are shown in Table 17:

TABLE 17

| | SRI | | |
|---|---|---|---|
| Stain Cloth | A | E | F |
| WFK-10C | 84.3 | 85.2 | 85.1 |
| Dust/sebum on cotton | 80.3 | 82.5 | 83.6 |

These results demonstrate that although Formula A is already a good cleaning detergent, use of a cationic or amine oxide co-surfactant in place of some SHP renders cleaning even better. Although use of a cationic or amine oxide co-surfactant is not required to achieve excellent cleaning benefits, their use at a low level is preferred.

Example 28E

HDLs with lower than about 40% total surfactant and containing more than about 5% of at least some SHP compositions, for example the SHP of Example 3, are often on the lower viscosity side of the consumer acceptable range. Due to this, it is desirable, although not imperative, to have thickeners which afford higher viscosities when added to SHP-containing HDLs. Acrylic acid-based and hydroxyethylcellulose (HEC) thickeners were tried in, and found to thicken, Formulation A which has a nominal viscosity of 5 cPs. The thickeners used, along with results are shown in Table 18 below:

TABLE 18

| Thickener | Concentration (Weight %) | Viscosity* (cPs) |
|---|---|---|
| None | | 5 |
| Accusol 820; acrylic; Rohm and Haas | 0.8 | 40 |
| Accusol 810A; acrylic; Rohm and Haas | 0.8 | 61 |
| Natrusol 250 GR; HEC; Aqualon | 0.8 | 44 |
| Cellosize QP 100MH; high MW HEC; Dow | 0.2 | 105 |
| | 0.6 | 860 |
| | 1.0 | 1560 |

*Measured with a Brookfield viscometer.

Example 28F

This example demonstrates the ability of SHP-containing HDLs to be concentrated to quite high overall surfactant levels. The following Table 19 details HDL formulas, along with their viscosities, ranging from 44% surfactant up to 66% surfactant:

TABLE 19

| Ingredient | 44% Surfactant Formula | 55% Surfactant Formula | 66% Surfactant Formula |
|---|---|---|---|
| SHP of Example 2 | 33 | 41 | 49 |
| $C_{12-15}EO_7$* | 11 | 14 | 17 |

TABLE 19-continued

| Ingredient | 44% Surfactant Formula | 55% Surfactant Formula | 66% Surfactant Formula |
|---|---|---|---|
| Monoethanolamine | 2.0 | 2.5 | 3.0 |
| Triethanolamine | 2.0 | 2.5 | 3.0 |
| Sodium Citrate | 2.0 | 2.5 | 3.0 |
| Water | 50.0 | 37.5 | 25.0 |
| Viscosity (cPs) | 411 | 541 | 810 |

All of the formulas are stable, isotropic and flowable.

Example 28G

It is often desirable to be able to ship and pump concentrated solutions of surfactant. A mixture of 26.25% of the SHP of Example 2, 26.25% C16 methylester sulfonate and 47.5% water was found to be flowable and pumpable at room temperature (22° C.).

Examples 29A-U

Green Laundry Detergent Formulas

As petroleum reserves continue to dwindle, it is becoming increasingly important to have effective laundry detergents based on bio-renewable sources. Bio-renewable sources include both animal and plant based feedstocks, although plant-based ones are preferred. We define here a Bio-renewable Carbon Index (BCI) for a given ingredient as:

BCI=100× (the number of bio-renewable carbon atoms in the molecule/the total number of carbon atoms in the molecule)

The following Table 20 details several prophetic core surfactant formulas wherein the BCI for the overall core formula is 100:

TABLE 20

| Surfactant* | Generic Formula | A | B | C | D | E | F | G | H | I | J | K |
|---|---|---|---|---|---|---|---|---|---|---|---|---|
| SE, PHSE, HSE | 2-90 | 20 | 30 | 15 | 10 | 10 | 10 | 15 | 10 | 20 | 20 | 30 |
| C16 methyl ester sulfonate | 0-30 | | | 5 | | | | | | | | |
| C12 methyl ester sulfonate | 0-30 | | | | 10 | | | | | | | |
| Sodium lauryl sulfate | 0-30 | | | | | 10 | | | | | | |
| Sodium coca sulfate | 0-30 | | | | | | 10 | | | | | |
| Sodium stearoyl lactylate | 0-30 | | | | | | | 5 | | | | |
| Sodium lauroyl lactate | 0-30 | | | | | | | | 10 | | | |
| alkyl polyglucoside (APG) | 0-60 | 20 | 10 | 20 | 20 | 20 | 20 | 20 | 20 | | | |
| Polyglycerol monoalkylate | 0-60 | | | | | | | | | 20 | | |
| Lauryl lactyl lactate | 0-30 | | | | | | | | | | 20 | 10 |
| Saponin | 0-30 | | | | | | | | | | | |
| Rhamnolipid | 0-30 | | | | | | | | | | | |
| Sphingolipid | 0-30 | | | | | | | | | | | |
| Glycolipid | 0-30 | | | | | | | | | | | |
| Abietic acid derivative | 0-30 | | | | | | | | | | | |
| Polypeptide | 0-30 | | | | | | | | | | | |

| Surfactant* | Generic Formula | L | M | N | O | P | Q | R | S | T | U |
|---|---|---|---|---|---|---|---|---|---|---|---|
| SE, PHSE, HSE | 2-90 | 30 | 30 | 30 | 30 | 30 | 30 | 50 | 40 | 30 | |
| C16 methyl ester sulfonate | 0-30 | | | | | | | | | | |
| C12 methyl ester sulfonate | 0-30 | | | | | | | | | | |
| Sodium lauryl sulfate | 0-30 | | | | | | | | 10 | 20 | 20 |
| Sodium coco sulfate | | | | | | | | | | | |
| Sodium stearoyl lactylate | 0-30 | | | | | | | | | | |
| Sodium lauroyl lactate | 0-30 | | | | | | | | | | |
| alkyl polyglucoside (APG) | 0-60 | | | | | | | 20 | 20 | 20 | |
| Polyglycerol monoalkylate | 0-60 | | | | | | | | | | |
| Lauryl lactyl lactate | 0-30 | | | | | | | | | | 10 |
| Saponin | 0-30 | 10 | | | | | | | | | |
| Rhamnolipid | 0-30 | | 10 | | | | | | | | |
| Sphingolipid | 0-30 | | | 10 | | | | | | | |
| Glycolipid | 0-30 | | | | 10 | | | | | | |
| Abietic acid derivative | 0-30 | | | | | 10 | | | | | |
| Polypeptide | 0-30 | | | | | | 10 | | | | |

*For the methyl ester sulfonates, the methanol from which the ester is made is from bio-renewable sources. APGs of varying HLB values are available from Henkel - a preferred APG is Glucopon 425N. A preferred polyglycerol monoalkylate is triglycerol monolaurate as described in Kato, et al., Journal of Surfactants and Detergents, October, 2003, Vol. 6, Number 4, pg.331. Tea saponin is available from Shanghai Greenway. Quillaja saponin is available from Sigma Chemical Co. More details of many of these surfactants are described in Surfactant Science Series, Marcel Dekker, Vols. 25 and 48, incorporated herein by reference.

These core surfactant formulations are not intended to be limiting in any way—optional ingredients described herein regarding the presently described technology can be added in the proportions described. In each case, these are intended to be liquid detergent formulas and, after the addition of optional ingredients, water would be used to bring the total weight up to 100%. There is no limit to the pH that these formulations can take but pH values between 7 and 12 are preferred and between 8 and 10 most preferred.

Examples 30A-GG

Premium to Mid-Tier Laundry Detergent Formulas

The following prophetic formulas, in Table 21, are intended to cover liquid laundry detergent formulas. Unless more narrowly defined in the table, the pH of these formulas is between a pH of about 7 to about 10, preferably between about 7.5 to about 9.5 and most preferably between about 8.5 to about 9.0. These formulas are not intended to be limiting in any way—optional ingredients described herein regarding the present technology can be added in the proportions described. In each case, these are intended to be liquid detergent formulas and, after the addition of optional ingredients, water would be used to bring the total weight up to 100%.

TABLE 21

| Ingredient* | Generic Formula | % Inclusion by Weight (Based on 100% Active) | | | | | | | | |
|---|---|---|---|---|---|---|---|---|---|---|
| | | A | B | C | D | E | F | G | H | I |
| SE, PHSE, HSE | 2-90 | 23 | 23 | 5.6 | 23 | 23 | 21 | 29 | 29 | 38 |
| Nonionic surfactant | 2-40 | 14 | 14 | 14 | 14 | 14 | 12 | 16 | 16 | 18 |
| AES | 0-35 | | | 17.4 | | | | | | |
| C16MES | 0-25 | | | | | | | | | |
| Cocoamide DEA | 0-25 | | | | | | | | | |
| AMMONYX ® LO | 0-6 | | | | | | | 2 | | |
| $C_{12}EO_3$ | 0-6 | | | | | | | 2 | | |
| Coconut fatty acid | 0-10 | | | | | | | | | |
| Borax pentahydrate | 0-3 | 2.7 | 2.7 | 2.7 | | 2.7 | 2.7 | 2.2 | 2.2 | 1.5 |
| Propylene glycol | 0-6 | 2.6 | 2.6 | 2.6 | 4.0 | 2.6 | 2.6 | 2.1 | 2.1 | 1.4 |
| Calcium chloride | 0-2 | | | | 0.2 | | | | | |
| Glycerol | 0-6 | | | | | | | | | |
| Sodium citrate | 0-10 | 3.9 | 3.9 | 3.9 | 3.9 | 3.9 | 3.9 | 3.9 | 3.9 | 5.0 |
| Triethanolamine | 0-6 | | | | | | | | | |
| Monoethanolamine | 0-6 | 3.5 | 3.5 | 3.5 | 3.5 | 3.5 | 3.5 | 3.5 | 3.5 | 4.5 |
| Fluorescent whitening agent (FWA) | 0-1 | 0.15 | 0.15 | 0.15 | 0.15 | 0.15 | 0.15 | 0.15 | 0.15 | 0.2 |
| Anti-redeposition agent | 0-1.5 | | | | | 0.8 | 0.8 | | 0.8 | |
| Thickener | 0-2 | 0.25 | 0.25 | 0.15 | 0.2 | 0.2 | 0.2 | | | |
| Thinner | 0-20 | | | | | | | | | 1-3 |
| Protease | 0-2 | 0.8 | 0.8 | 0.8 | 0.8 | 0.8 | 0.8 | 0.8 | 0.8 | 1.1 |
| Amylase | 0-2 | 0.4 | 0.4 | 0.4 | 0.4 | 0.4 | 0.4 | 0.4 | 0.4 | 0.55 |
| Lipase | 0-2 | 0.2 | | | | | | | | |
| Mannanase | 0-2 | 0.1 | | | | | | | | |
| Cellulase | 0-2 | 0.02 | | | | | | | | |
| pH | | | | | | | | 7.0-7.5 | | |

| Ingredient* | % Inclusion by Weight (Based on 100% Active) | | | | | | | | | |
|---|---|---|---|---|---|---|---|---|---|---|
| | J | K | L | M | N | O | P | Q | R | S |
| SE, PHSE, HSE | 38 | 38 | 38 | 46 | 46 | 46 | 6 | 11.4 | 6 | 11.4 |
| Nonionic surfactant | 11 | 18 | 11 | 24 | 14 | 14 | 10 | 10 | 10 | 10 |
| AES | | | | | | | 5.4 | | 5.4 | |
| C16MES | | | | | | | | | | |
| Cocoamide DEA | | | | | | | | | | |
| AMMONYX ® LO | | | | | | | 1 | 1 | 1 | 1 |
| $C_{12}EO_3$ | 7 | | 7 | | 10 | 10 | | | | |
| Coconut fatty acid | | | | | | | 1 | | 1 | |
| Borax pentahydrate | 1.5 | 1.5 | 1.5 | | 0.5 | 0.5 | | 2.2 | | |
| Propylene glycol | 1.4 | 1.4 | 1.4 | 3.0 | 1.0 | 1.0 | 2.1 | 2.1 | | |
| Calcium chloride | | | | 0.1 | | | 0.15 | | | |
| Glycerol | | | | | | | | | | |
| Sodium citrate | 5.0 | 5.0 | 5.0 | 5.0 | 5.0 | 5.0 | 1.4 | 1.4 | 3.5 | 3.5 |
| Triethanolamine | | | | | | | 0.52 | 0.52 | 0.52 | 0.52 |
| Monoethanolamine | 4.5 | 4.5 | 4.5 | 4.5 | 4.5 | 4.5 | 0.53 | 0.53 | 0.53 | 0.53 |
| Fluorescent whitening agent (FWA) | 0.2 | 0.2 | 0.2 | 0.2 | 0.2 | 0.2 | 0.15 | 0.15 | 0.15 | 0.15 |
| Anti-redeposition agent | | | | | | | | | | |
| Thickener | | | | | | | 0.15 | 0.25 | 0.15 | 0.25 |

TABLE 21-continued

| | | | | | | | | |
|---|---|---|---|---|---|---|---|---|
| Thinner | | 1-3 | | 3-7 | | 2-5 | | |
| Protease | 1.1 | 1.1 | 1.1 | 1.2 | 1.2 | 1.2 | 0.6 | 0.6 |
| Amylase | 0.55 | 0.55 | 0.55 | 0.6 | 0.6 | 0.6 | 0.3 | 0.3 |
| Lipase | | 0.25 | 0.25 | | | | | |
| Mannanase | | 0.13 | 0.13 | | | | | |
| Cellulase | | 0.02 | 0.02 | | | | | |
| pH | 7.0-7.5 | | | | | | | |

| | % Inclusion by Weight (Based on 100% Active) | | | | | | | | | |
|---|---|---|---|---|---|---|---|---|---|---|
| Ingredient* | T | U | V | W | X | Y | Z | AA | BB | CC |
| SE, PHSE, HSE | 11.4 | 29 | 38 | 38 | 46 | 6.4 | 12.4 | 12.4 | 10.4 | 25 |
| Nonionic surfactant | 10 | 16 | 18 | 11 | 14 | | | | | |
| AES | | | | | | 6 | | | | |
| C16MES | | | | | | 4 | 4 | 4 | 4 | 11 |
| Cocoamide DEA | | | | | | 9.8 | 9.8 | 9.8 | 9.8 | 17 |
| AMMONYX ® LO | | | | | | | | | 2 | 2 |
| $C_{12}EO_3$ | | | | 7 | 10 | | | | | |
| Coconut fatty acid | | | | | | | | | | |
| Borax pentahydrate | | | | | | 1.7 | 1.7 | | 1.7 | 1.2 |
| Propylene glycol | | | | | | | | | | |
| Calcium chloride | | | | | | | | 0.15 | | |
| Glycerol | | | | | | 4.6 | 4.6 | 5.5 | 4.6 | 3 |
| Sodium citrate | 3.5 | 3.9 | 5.0 | 5.0 | 5.0 | | | | | |
| Triethanolamine | 0.52 | | | | | | | | | |
| Monoethanolamine | 0.53 | 3.5 | 4.5 | 4.5 | 4.5 | | | | | |
| Fluorescent whitening agent (FWA) | 0.15 | 0.15 | 0.2 | 0.2 | 0.2 | 0.15 | 0.15 | 0.15 | 0.15 | 0.15 |
| Anti-redeposition agent | | | | | | | | | | |
| Thickener | 0.25 | | | | | 0.1 | 0.25 | 0.25 | 0.25 | |
| Thinner | | 1-3 | | | | | | | | |
| Protease | | | | | | 0.6 | 0.6 | 0.6 | 0.6 | 1 |
| Amylase | | | | | | 0.3 | 0.3 | 0.3 | 0.3 | 0.5 |
| Lipase | | | | | | | | | 0.2 | |
| Mannanase | | | | | | | | | 0.1 | |
| Cellulase | | | | | | | | | 0.02 | |
| pH | | | | | | | | | | |

| | % Inclusion by Weight (Based on 100% Active) | | | |
|---|---|---|---|---|
| Ingredient* | DD | EE | FF | GG |
| SE, PHSE, HSE | 27 | 25 | 27 | 35 |
| Nonionic surfactant | | | | |
| AES | | | | |
| C16MES | 11 | 11 | 11 | 13 |
| Cocoamide DEA | 17 | 10 | 10 | 12 |
| AMMONYX ® LO | | 2 | | |
| $C_{12}EO_3$ | | 7 | 7 | 10 |
| Coconut fatty acid | | | | |
| Borax pentahydrate | 1.2 | 1.2 | 1.2 | 1.2 |
| Propylene glycol | | | | |
| Calcium chloride | | | | |
| Glycerol | 3 | 3 | 3 | 3 |
| Sodium citrate | | | | |
| Triethanolamine | | | | |
| Monoethanolamine | | | | |
| Fluorescent whitening agent (FWA) | 0.2 | 0.2 | 0.2 | 0.2 |
| Anti-redeposition agent | | | | |
| Thickener | | | | |
| Thinner | | | | |
| Protease | 1 | 1 | 1 | 1 |

TABLE 21-continued

| | | | | |
|---|---|---|---|---|
| Amylase | 0.5 | 0.5 | 0.5 | 0.5 |
| Lipase | | | | |
| Mannanase | | | | |
| Cellulase | | | | |
| pH | | | | |

*A preferred nonionic surfactant is BIO-SOFT ® N25-7, Stepan Company. A preferred AES is STEOL ® CS-460, Stepan Company. A preferred FWA is TINOPAL CBS-X, Ciba. A preferred thickener is Cellosize QP 100MH, Dow. Preferred thinners include: $C_{12}EO_2$, $C_{12}EO_3$ (in addition to that already included in certain formulas in the table), ethanol, isopropanol, sodium xylene sulfonate, sodium cumene sulfonate, 2-methoxy ethanol, 2-butoxyethanol, methoxy ethoxy ethanol and combinations of these. A preferred preservative for these formulas is Neolone M-10 from Rohm and Haas used at 75 ppm on a 100% active basis.

Examples 31A-EE

Bargain Laundry Detergent Formulas

The following prophetic formulas, in Table 22, are intended to cover liquid laundry detergent formulas. Unless more narrowly defined in the table, the pH of these formulas is between pH 10 and 12.5, preferably between 11.0 and 12.0 and most preferably between 11.3 and 11.8. These formulas are not intended to be limiting in any way—optional ingredients described herein regarding the present technology can be added in the proportions described. In each case, these are intended to be liquid detergent formulas and, after the addition of optional ingredients, water would be used to bring the total weight up to 100%.

TABLE 22

| | | % Inclusion by Weight (Based on 100% Active) | | | | | | | | |
|---|---|---|---|---|---|---|---|---|---|---|
| Ingredient* | Generic Formula | A | B | C | D | E | F | G | H | I |
| SE, PHSE, HSE | 2-90 | 1 | 7.3 | 5.5 | 5.5 | 5.5 | 3 | 14 | 28 | 37 |
| Nonionic surfactant | 2-40 | 6 | 6 | 10 | 10 | 8 | 12 | 12 | 24 | 28 |
| AES | 0-35 | 6.3 | | | | | 11 | | | |
| AMMONYX ® LO | 0-6 | | | 1.5 | 1.5 | | | | | |
| $C_{12}EO_3$ | 0-6 | | | 2 | 2 | 4 | | | | |
| Coconut fatty acid | 0-10 | 0.2 | | | | | | | | |
| Sodium metasilicate | 0-10 | | | | | | | | | |
| Sodium carbonate | 0-10 | 3 | 3 | 3 | 3 | 3 | 6 | 6 | 7 | 8 |
| Fluorescent whitening agent (FWA) | 0-1 | 0.15 | 0.15 | 0.15 | 0.15 | 0.15 | 0.2 | 0.2 | 0.2 | 0.25 |
| Anti-redeposition agent | 0-1.5 | | | | 0.5 | | | | | |
| Thickener | 0-2 | 0.05 | 0.35 | 0.35 | 0.35 | 0.35 | 0.2 | 0.35 | | |
| Thinner | 0-20 | | | | | | | | | |
| pH | | | | | | | | | | |

| | % Inclusion by Weight (Based on 100% Active) | | | | | | | | |
|---|---|---|---|---|---|---|---|---|---|
| Ingredient* | J | K | L | M | N | O | P | Q | R | S |
| SE, PHSE, HSE | 37 | 35 | 37 | 35 | 45 | 43 | 45 | 43 | 7 | 14 |
| Nonionic surfactant | 28 | 28 | 18 | 18 | 30 | 30 | 17 | 17 | 13 | 13 |
| AES | | | | | | | | | 7 | |
| AMMONYX ® LO | | 2 | | 2 | | 2 | | 2 | | |
| $C_{12}EO_3$ | | | 10 | 10 | | | 13 | 13 | | |
| Coconut fatty acid | | | | | | | | | | |
| Sodium metasilicate | | | | | | | | | 3 | 3 |
| Sodium carbonate | 8 | 8 | 8 | 8 | 8 | 8 | 8 | 8 | | |
| Fluorescent whitening agent (FWA) | 0.25 | 0.25 | 0.25 | 0.25 | 0.25 | 0.25 | 0.25 | 0.25 | 0.2 | 0.2 |
| Anti-redeposition agent | | | | | | | | | | |
| Thickener | | | | | | | | | 0.2 | 0.35 |
| Thinner | 3 | 3 | | | 5 | 5 | | | | |
| pH | | | | | | | | | 11.5 to 12.0 | |

TABLE 22-continued

| Ingredient* | % Inclusion by Weight (Based on 100% Active) | | | | | | | | | | | |
|---|---|---|---|---|---|---|---|---|---|---|---|---|
| | T | U | V | W | X | Y | Z | AA | BB | CC | DD | EE |
| SE, PHSE, HSE | 12.5 | 14 | 28 | 37 | 37 | 35 | 35 | 45 | 45 | 43 | 43 | 4.5 |
| Nonionic surfactant | 11 | 9 | 24 | 28 | 21 | 28 | 28 | 30 | 17 | 30 | 17 | 4.5 |
| AES | | | | | | | | | | | | |
| AMMONYX ® LO | 1.5 | | | | | 2 | 2 | | | 2 | 2 | |
| $C_{12}EO_3$ | 2 | 4 | | 7 | | | 7 | | 13 | | 13 | |
| Coconut fatty acid | | | | | | | | | | | | |
| Sodium metasilicate | 3 | 3 | 6 | 6 | 6 | 6 | 6 | 7 | 7 | 7 | 7 | |
| Sodium carbonate | | | | | | | | | | | | 1.3 |
| Fluorescent whitening agent (FWA) | 0.2 | 0.2 | 0.25 | 0.25 | 0.25 | 0.25 | 0.25 | 0.25 | 0.25 | 0.25 | 0.25 | 0.1 |
| Anti-redeposition agent | | | | | | | | | | | | |
| Thickener | 0.35 | 0.35 | | | | | | | | | | |
| Thinner | | | | 2 | | 2 | | 5 | | 5 | | |
| pH | | | | | | 11.5 to 12.0 | | | | | | |

*A preferred nonionic surfactant is BIO-SOFT ® N25-7, Stepan Company. A preferred AES is STEOL ® CS-460, Stepan Company. A preferred FWA is TINOPAL CBS-X, Ciba. A preferred thickener is Cellosize QP 100MH, Dow. Preferred thinners include: $C_{12}EO_2$, $C_{12}EO_3$, ethanol, isopropanol, sodium xylene sulfonate, sodium cumene sulfonate, 2-methoxy ethanol, 2-butoxyethanol, methoxy ethoxy ethanol and combinations of these.

Comparative Examples 32A-B

HDL Concentrates-Sodium Versus Potassium Salt

SE sulfonic acid was obtained under conditions comparable to the sulfonation step of Example 3. Sodium and potassium salts of SHP were prepared as 51% solids aqueous solutions by neutralizing the SE sulfonic acid with aqueous NaOH and KOH, respectively, and hydrolyzing the sultones of the resulting solutions at 85° C. for 16 hours.

The general formula of the sodium and potassium salt compositions tested in Comparative Example A is as follows: 56% surfactant (kept at a constant ratio of 3:1, SHP:nonionic 25-7); 2.5% Triethanolamine; 2.5% Monoethanolamine; 2.5% sodium citrate dehydrate. The total amount of solids is 63.5%.

The viscosity values of the two compositions tested in Comparative Example A are shown below in Table 23:

TABLE 23

| SHP | Viscosity (cPs) |
|---|---|
| Potassium salt version | 538 |
| Sodium salt version | 870 |

The general formula of the sodium and potassium salt compositions tested in Comparative Example B is as follows: 67% surfactant (kept at a constant ratio of 3:1, SHP:nonionic 25-7); 3% Triethanolamine; 3% Monoethanolamine; 3% sodium citrate dehydrate. The total amount of solids is 76%.

The viscosity values of the two compositions tested in Comparative Example B are shown below in Table 24:

TABLE 24

| SHP | Viscosity (cPs) |
|---|---|
| Potassium salt version | 1180 |
| Sodium salt version | 2152 |

In each case, the HDL made from the potassium salt is significantly lower in viscosity.

Example 33

Comparative Cleaning Study Between the SHP of Example 14 and LAS/AES Formulas

TABLE 25

| | % Inclusion by Weight (100% active) | |
|---|---|---|
| Ingredient* | Comparative Formula 1 | A |
| SHP of Example 14 | | 18.0 |
| sodium linear alkylbenzene sulfonate | 7.0 | |
| AES | 11.0 | |
| $C_{12-15}EO_7$ | 16.0 | 16.0 |
| $C_{12}$dimethyl amine oxide | 1.0 | 1.0 |
| Coconut fatty acid | 1.0 | 1.0 |
| Borax pentahydrate | 2.25 | 2.25 |
| Propylene glycol | 2.0 | 2.0 |
| Citric acid | 2.0 | 2.0 |
| Monoethanolamine | 0.75 | 0.75 |
| Triethanolamine | 0.75 | 0.75 |
| Protease | 1.1 | 1.1 |
| Amylase | 0.55 | 0.55 |
| Neolone M-10 | 0.0075 | 0.0075 |
| Water | 54.6 | 54.6 |
| pH | 8.5-9.0 | |

*$C_{12-15}EO_7$ = BIO-SOFT ® N25-7; AES = STEOL ® CS-460; $C_{12}$dimethyl amine oxide = AMMONYX ® LO; all from Stepan Company, Northfield, IL. Neolone M-10 = preservative from Rohm and Haas. Protease = Purafect 4000L; Amylase = Purastar ST 15000L; both from Genencor.

Cleaning results are as follows:

TABLE 26

| Stain Cloth | SRI Comparative Formula 1 | A |
|---|---|---|
| EMPA 106 | 67.7 | 68.0 |
| WFK-10C | 86.1 | 86.6 |

The results in Table 26 demonstrate that the SHP formula, as shown in Table 25, gives better cleaning results than the analogous LAS/AES formula on both EMPA 106 and WFK-10C.

Example 34

Comparative Cleaning Study Between Capric Fatty Acid Chain-Terminated SE and LAS/AES Formulas A composition comprising specific sulfo-estolides of Formula 1, wherein R is $CH_3(CH_2)_8$, n is 0, and a is 0 (C10/C18 SE Dimer), as shown in Table 27, was prepared as follows: A solution of 99% methyl oleate in pentane was batch sulfonated with about 1 mole equivalent gaseous $SO_3$, diluted with $N_2$, maintaining the reaction temperature below about 20° C. The obtained acid was stripped of pentane solvent under reduced pressure and then added to decanoic (capric) acid at an approximate molar ratio of 1 mole sulfonated methyl oleate to 2 moles of fatty acid. The resulting mixture was stirred at 65° C. for 1 hour, was allowed to cool, and was then dissolved in petroleum ether and extracted with a 1:1 mixture of ethanol and water. The obtained aqueous alcohol solution of sulfonic acid was extracted with three additional portions of fresh petroleum ether in order to remove residual unreacted decanoic acid. The sulfonic acid solution was then neutralized to a pH of 7 by the addition of aqueous KOH. The solution of potassium sulfonate salts was then subjected to methyl ester hydrolysis with a slight excess of potassium carbonate by heating to 70° C. for 11 hours. The resulting solution was adjusted to about pH 8.7 with aqueous $H_2SO_4$ and then concentrated to afford a sulfo-estolide enriched in C10/C18 SE dimer as a 30 percent solid solution. $^1H$ NMR spectroscopy of the product indicated that relative to total moles of C18 fatty acid chains that were incorporated in the product, about 40 mole percent was in the form of C10/C18 SE Dimer, 21 mole percent was in the form of alkene-sulfonate functionalized C18 fatty acid, and 30 mole percent was in the form of hydroxyl sulfonate functionalized C18 fatty acid.

TABLE 27

| Ingredient | % Inclusion (100% active) Comparative Formula 2 | B |
|---|---|---|
| C10 SE Dimer | | 15.0 |
| sodium linear alkylbenzene sulfonate | 15.0 | |
| $C_{12-15}EO_7$* | 5.0 | 5.0 |
| Monoethanolamine | 1.0 | 1.0 |
| Triethanolamine | 1.0 | 1.0 |
| Sodium Citrate | 1.0 | 1.0 |
| Water | 77.0 | 77.0 |
| pH | 10.0 | |

Cleaning results are as follows:

TABLE 28

| Stain Cloth | SRI Comparative Formula 2 | B |
|---|---|---|
| Dust/sebum on cotton | 81.4 | 83.2 |
| Grass on cotton | 80.6 | 80.6 |
| Spaghetti sauce on cotton | 92.9 | 93.7 |

The results in Table 28 demonstrate that the enriched C10/C18 SE dimer formula gives as good or better cleaning results than the analogous LAS/AES formula on these soils/stains.

Examples 35A-F

Example 35A

The following formulations in Table 29 were made and tested for cleaning:

TABLE 29

| Ingredient* | % Inclusion by Weight (100% active) Comparative Formula 1 | A |
|---|---|---|
| SHP of Example 14 | | 15.0 |
| sodium linear alkylbenzene sulfonate | 7.0 | |
| AES | 8.0 | |
| $C_{12-15}EO_7$ | 13.0 | 13.0 |
| $C_{12}$dimethyl amine oxide | 1.0 | 1.0 |
| Coconut fatty acid | 1.0 | 1.0 |
| Citric acid | 1.65 | 1.65 |
| Monoethanolamine | 0.53 | 0.53 |
| Triethanolamine | 0.53 | 0.53 |
| Neolone M-10 | 0.0075 | 0.0075 |
| Water | 67.28 | 67.28 |
| pH | 8.5-9.0 | |

*$C_{12-15}EO_7$ = BIG-SOFT ® N25-7; AES = STEOL ® CS-460; $C_{12}$dimethyl amine oxide = AMMONYX ® LO; all from Stepan Company, Northfield, IL. Neolone M-10 = preservative from Rohm and Haas.

Cleaning results are as follows:

TABLE 30

| Stain Cloth | SRI Comparative Formula 1 | A |
|---|---|---|
| Spaghetti Sauce | 84.9 | 87.6 |
| EMPA 106 | 69.0 | 70.5 |

The results in Table 30 demonstrate that this non-enzyme-containing, pH less than 10, SHP formula gives better cleaning results than the analogous LAS/AES formula on both spaghetti sauce and EMPA 106.

Example 35B

The following formulations in Table 31 were made and tested for cleaning:

TABLE 31

| Ingredient* | % Inclusion by Weight (100% active) | |
| --- | --- | --- |
| | Comparative Formula 2 | B |
| SHP of Example 14 | | 7.5 |
| sodium linear alkylbenzene sulfonate | 4.5 | |
| AES | 3.0 | |
| $C_{12-15}EO_7$ | 6.0 | 6.0 |
| $C_{12}$dimethyl amine oxide | 0.5 | 0.5 |
| Sodium xylene•sulfonate | 0.7 | 0.7 |
| Sodium metasilicate | 2.75 | 2.75 |
| Water | 82.55 | 82.55 |
| pH | 11.5-12.0 | |

*$C_{12-15}EO_7$ = BIO-SOFT ® N25-7; AES = STEOL ® CS-460; $C_{12}$dimethyl amine oxide = AMMONYX ® LO; all from Stepan Company, Northfield, IL.

Cleaning results are as follows:

TABLE 32

| | SRI | |
| --- | --- | --- |
| Stain Cloth | Comparative Formula 1 | A |
| Spaghetti Sauce | 84.2 | 85.9 |
| EMPA 106 | 69.1 | 70.8 |

The results in Table 32 demonstrate that this high pH, metasilicate-based SHP formula gives better cleaning results than the analogous LAS/AES formula on both spaghetti sauce and EMPA 106.

Example 35C

The cleaning experiments in Example 35B were repeated using 65° F. wash water. The SRI value on spaghetti sauce for Comparative Formula 1 from Example 35 was 81.0 while that for the SHP formula was 81.3. This example demonstrates that SHP delivers excellent cold water cleaning.

Example 35D

The following formulas in Table 33 were made and tested for cleaning in 65° F. water:

TABLE 33

| Ingredient* | % Inclusion by Weight (100% active) | |
| --- | --- | --- |
| | Comparative Formula 3 | C |
| SHP of Example 14 | | 7.5 |
| sodium linear alkylbenzene sulfonate | 4.5 | |
| AES | 3.0 | |
| $C_{12-15}EO_7$ | 6.0 | 6.0 |
| $C_{12}$dimethyl amine oxide | 0.5 | 0.5 |
| Sodium xylene sulfonate | 0.7 | 0.7 |
| Sodium carbonate | 2.75 | 2.75 |
| Water | 82.55 | 82.55 |
| pH | 11.5-12.0 | |

*$C_{12-15}EO_7$ = BIO-SOFT ® N25-7; AES = STEOL ® CS-460; $C_{12}$dimethyl amine oxide = AMMONYX ® LO; all from Stepan Company, Northfield, IL.

The cleaning experiments in Example 35B were repeated using 65° F. wash water. The SRI value on EMPA 106 for Comparative Formula 3 was 69.7 while that for the analogous SHP formula was 70.3. This example further demonstrates that SHP delivers excellent cold water cleaning.

Example 35E

Clean, white cotton cloths were included in the washes of Example 35C to determine each formula's ability to suspend soils once they are removed from the soiled swatches. The SRI value for the non-SHP formula was 99.6 while that for the SHP formula was 99.7. This example demonstrates that SHP is very good at keeping soils suspended in the wash liquor once they are removed from the soiled swatches.

Example 35F

It was noted above that the wash cycle, when SHP-containing HDL was used in the Whirlpool Duet Sport machines, lasted 7 minutes less than when the analogous LAS/AES formula was used. These machines stop when a certain set amount of water has been removed from the fabric in the machine. Without being bound by theory, residual surfactant will bind water on and inside the fabric and since SHP rinses away more easily than LAS/AES, less water is bound with SHP and the water is spun out of the fabric more easily. This example demonstrates that use of SHP-based HDLs can lead to energy savings by reducing the amount of time the machine needs to remove a predetermined amount of water. In this case, the cycle normally lasts for 54 minutes and therefore the cycle time was 12.7% less when the SHP-based HDL was used.

Examples 36A-D

Example 36A

In 100 ml of 65° F. tap water with a 1" magnetic stirrer on a Corning magnetic stir plate set at 3.5, 2 ml of Comparative Formula 1 from Example 33 was quickly added to the mixing water from a pipette. It took 14 seconds before all the swirls from dissolving HDL were gone and the solution was clear while for the SHP HDL (Formula A from Example 33), it took three seconds. This example demonstrates that the HDL formulated with SHP dissolves into solution much faster than the analogous HDL formulated with AES/LAS as the anionic surfactant.

Example 36B

For Comparative Formula 1 in Example 33, heat was added during the batching to facilitate solubilization of certain ingredients and thereby reduce batch cycle time. With Formula A in Example 33, no added heat was needed to speed up batching. This simplified processing route demonstrates that SHP-based HDLs can be made in comparable time to LAS/AES-based HDLs while using less energy

Example 36C

A leading liquid laundry detergent was purchased and the water driven off in an oven yielding a solids level of 24.4%. Based on this, an analogous SHP-containing HDL was produced in the lab (SHP from Example 2 was used) wherein the anionic active of the commercial HDL, analyzed to be 12% by titration and gas chromatography, was matched in a SHP HDL. Other ingredients in the commercial formula were also added in analyzed proportions to bring the SHP HDL to 24.4% solids. Each HDL was then used to wash 6 pounds of 65%/35% cotton/polyester pillowcases and four of each of the following soiled swatches—dust/sebum on cotton, red wine, clay, EMPA 116—in a Whirlpool Duet Sport washing machine with 100 F wash water, 60 g of detergent. The washed clothes were each then sent through 3 rinse cycles. Rinse water from the second and third rinse cycles were collected and visually inspected. For the commercial HDL, the rinses water for both the second and third rinses was visually hazy while that for the analogous SHP HDL was perfectly clear to the eye. This example demonstrates that SHP-based HDLs rinse away off of laundered clothes, and are therefore less likely to leave residues, more easily than HDLs based on LAS/AES.

Example 36D

This example, Table 34, lists prophetic softergent formulas:

TABLE 34

| Ingredient | % Inclusion by Weight (Based on 100% Active) | | | | | | |
|---|---|---|---|---|---|---|---|
| | A | B | C | D | E | F | H |
| SE, PHSE, HSE | 23.0 | 46.0 | 15.0 | 11.0 | 45.0 | 11.0 | 45.0 |
| Nonionic surfactant | 14.0 | 24.0 | | 9.0 | 30.0 | 9.0 | |
| C16MES | | | 7.0 | | | | |
| Cocoamide DEA | | | 14.0 | | | | |
| Borax pentahydrate | 2.7 | 1.2 | 1.7 | | | | |
| Propylene glycol | 2.6 | 1.8 | | | | | |
| Glycerol | | | 4.6 | | | | |
| Sodium citrate | 3.9 | 5.0 | | | | | |
| Triethanolamine | | | | | | | |
| Sodium carbonate | | | | 3 | 6 | | |
| Sodium metasilicate | | | | | | 3 | 6 |
| Monoethanolamine | 3.5 | 4.5 | | | | | |
| Fluorescent whitening agent (FWA) | 0.15 | 0.2 | 0.15 | 0.15 | 0.2 | 0.15 | 0.2 |
| Thickener | 0.25 | | 0-0.2 | 0.3 | | | |
| Thinner | | 3-7 | | | 2-8 | | 2-8 |
| Protease | 0-1.5 | 0-1.5 | 0-1.5 | | | | |
| Amylase | 0-0.8 | 0-0.8 | 0-0.8 | | | | |
| Lipase | 0-0.5 | 0-0.5 | 0-0.5 | | | | |
| Mannanase | 0-0.3 | 0-0.3 | 0-0.3 | | | | |
| Cellulase | 0-0.2 | 0-0.2 | 0-0.2 | | | | |
| Softener | | | | 0.3-10 | | | |
| pH | | 7-10 | | | | 10-12.5 | |

After ingredients are added, water is added to bring the percent up to 100%. Preferred softening agents include: Accosoft 365 (tallow polyethoxy ammonium methylsulfate), Ammonyx Cetac (cetyl trimethyammonium chloride) from Stepan Company; Polyquaterium 10/soap mixtures and monoalkyl quat/soap mixtures.

The formulations shown in the above table are just some examples of the types of softergents that can be created within the scope of the presently described technology. Similar such softergents can also be created by adding appropriate softening molecules and amounts to the formulations detailed in Examples 32 and 33.

CONCLUSION

The embodiments and examples described here are illustrative, and do not limit the presently described technology in any way. The scope of the present technology described in this specification is the full scope defined or implied by the claims. Additionally, any references noted in the detailed description section of the instant application are hereby incorporated by reference in their entireties, unless otherwise noted.

What is claimed is:

1. A composition comprising one or more compounds having the following Formula 1:

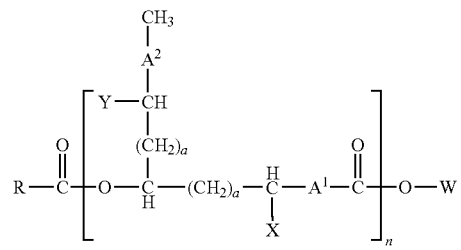

Formula 1 wherein n is an integer from 1-30;
one of X and Y is $SO_3$—Z, the other of X and Y is H, and X and Y are independently assigned in each repeating unit;
$A^1$ and $A^2$ are linear or branched, saturated or unsaturated, substituted or un-substituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or un-substituted hydrocarbon wherein the total number of carbon atoms is from 1 to about 24;
W is a monovalent or divalent metal cation, ammonium cation, substituted ammonium cation, H, or an alkyl or substituted alkyl group; and
Z is H, or a monovalent or divalent metal cation, ammonium or substituted ammonium cation.

2. The composition of claim 1, wherein a is 0.

3. The composition of claim 1, wherein n is 1, 2, or 3.

4. The composition of claim 1, wherein R is about 8 to about 16 carbon atoms.

5. The composition of claim 1, wherein R is derived from a saturated fatty carboxylic acid.

6. The composition of claim 1, further comprising:
0% to about 95% by weight of at least one internal hydroxy sulfonates of fatty acid or salt;
0% to about 95% by weight of at least one internal unsaturated sulfonates of fatty acid or salt; and
0% to about 95% by weight of at least one non-sulfonated estolide acid or salt.

7. A method for laundering one or more fabric articles using one or more compositions of claim 1, comprising the steps of:

placing the one or more fabric articles to be laundered into a high efficiency or regular washing machine;

placing a sufficient amount of the composition or mixture into the high efficiency or regular washing machine to provide a concentration of the composition in water of about 0.001% by weight to about 5% by weight when the high efficiency or regular washing machine is operated during a wash cycle; and actuating the wash cycle of the high efficiency or regular washing machine to launder the one or more fabric articles.

8. A method for hand laundering fabrics using one or more compositions of claim 1, or mixtures thereof, comprising the steps of: placing one or more fabric articles to be hand laundered into a receptacle;

placing a sufficient amount of the composition or mixture into the receptacle to provide a concentration of the composition or mixture in water of about 0.001% by weight to about 5% by weight; and hand washing the fabric article in the receptacle to launder the fabric article.

9. A method for laundering one or more fabric articles using at least one composition of claim 1, comprising the steps of:

placing one or more fabric articles to be laundered in a high efficiency or regular washing machine that uses a washing medium to launder clothes;

providing the composition or mixture comprising about 1% to about 99% by weight of a sulfo-estolide;

placing into the high efficiency or regular washing machine a sufficient amount of the composition or mixture to provide a concentration of the composition in the washing medium of about 0.001% by weight to about 5% by weight when the machine is operated during a wash cycle; and actuating the wash cycle of the high efficiency or regular washing machine to launder the one or more fabric articles.

10. A method of reducing the viscosity of at least one composition comprising at least one surfactant in water, the method comprising the step of including in the composition a sufficient amount of one or more compounds of claim 1, effective to reduce the viscosity of the composition.

11. At least one surfactant composition comprising at least one surfactant, water, and a sufficient amount of one or more compositions of claim 1, effective to reduce the viscosity of the surfactant composition.

12. A method of reducing the foam production of at least one composition comprising at least one surfactant in water, the method comprising the step of including or incorporating in the composition a sufficient amount of one or more compositions of claim 1, effective to reduce the foam production of the composition.

13. At least one surfactant composition comprising one or more surfactants, water, and a sufficient amount of one or more compositions of claim 1, effective to reduce the foam production of the surfactant composition.

14. The composition of claim 1, wherein W is a substituted C3 alkyl group where the structure of Formula 1 is incorporated one or more times as an ester in a monoglyceride, a diglyceride, or a triglyceride.

15. The composition of claim 14, wherein the incorporated Formula 1 is an ester of a triglyceride.

16. A method of cleaning at least one substrate, comprising the steps of:

providing at least one composition comprising a first surfactant comprising one or more compounds of claim 1, or mixtures thereof, and a second surfactant comprising at least one anionic, cationic, nonionic, ampholytic, zwitterionic surfactant, or combinations thereof;

contacting at least one soiled substrate with the composition; and removing the composition and soil from the substrate.

17. The method of claim 16, wherein the composition and soil are removed from the substrate by rinsing the substrate with water, and the first surfactant is present in an amount effective to improve the efficiency of rinsing, by reducing the amount of water needed to remove the composition to a specific residual concentration.

18. The method of claim 16, wherein the composition and soil are removed from the substrate by dewatering the substrate during a washing machine spin cycle, and the first surfactant is present in an amount effective to improve the efficiency of dewatering, by increasing the amount of water removed from the substrate during the washing machine spin cycle.

19. The method of claim 16, wherein the substrate is one or more laundry articles and the first surfactant is present in an amount effective to improve the cleanliness of the one or more laundry articles treated according to the method.

20. The method of claim 16, wherein the soiled substrate is contacted with the composition at a temperature at or lower than about 70° F.

21. The method of claim 16, wherein the first surfactant is present in an amount effective to improve the ability of suspending soils once they are removed from the substrate.

22. A liquid laundry detergent composition, comprising:
about 1% to about 99% by weight of at least one compound having the following Formula 1:

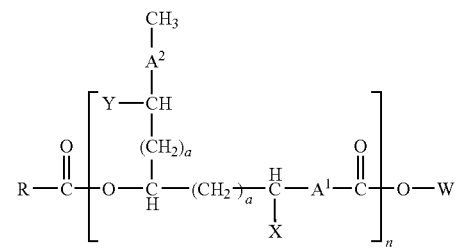

Formula 1 wherein n is an integer from 1-30;

one of X and Y is $SO_3$—Z, the other of X and Y is H, and X and Y are independently assigned in each repeating unit;

$A^1$ and $A^2$ are linear or branched, saturated or unsaturated, substituted or un-substituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or un-substituted, wherein the total number of carbon atoms is from about 1 to about 24;

W is a monovalent or divalent metal cation, ammonium cation or substituted ammonium cation, H, or an alkyl or substituted alkyl group;

Z is H, or a monovalent or divalent metal cation, ammonium or substituted ammonium cation; and 0% to about 40% by weight of at least one additional surfactant; and about 1% to about 99% by weight of water.

23. The composition of claim 22, wherein W is potassium and the total surfactant concentration is greater than about 40%.

24. The composition of claim 22, wherein W is potassium and the total surfactant concentration is greater than about 20%.

25. The composition of claim 22, wherein the formulation further comprises 0% to about 40% by weight of at least one additive.

26. The composition of claim 25, wherein the at least one additive is a member selected from the group consisting of at least one builder, at least one alkaline agent, at least one enzyme, at least one chelating agent, at least one polymeric dispersing agent, at least one suds suppressor, at least one alkyl polyglucoside, at least one polymeric suds enhancer, at least one antimicrobial agent, at least one softener, at least one odor control agent, at least one thickener, derivatives thereof, and combinations thereof.

27. The composition of claim 22, having improved anti-redeposition properties as compared to an analogous heavy duty detergent based on at least one linear alkylbenzene sulfonate, at least one alcohol ether sulfate, or a mixture thereof that does not contain at least one compound of Formula 1.

28. The composition of claim 22, wherein the at least one additional surfactant is a member selected from the group consisting of at least one anionic surfactant, at least one nonionic surfactant, at least one cationic surfactant, at least one ampholytic surfactant, at least one zwitterionic surfactant, derivatives thereof, and combinations thereof.

29. The composition of claim 28, wherein the anionic surfactant is alkyl ether sulfate.

30. The composition of claim 22, wherein the at least one additional surfactant or at least one additional additive improves laundering of a material soiled with grass, or spaghetti sauce, or dust/sebum containing soil.

31. The composition of claim 30, wherein the material is at least one cotton fabric, at least one polyester cotton blend, at least one polyester fabric, at least one silk material, at least one nylon material, at least one wool material, or a combination thereof.

32. The composition of claim 22, wherein the formulation is biodegradable.

33. The composition of claim 22, wherein the formulation can be a liquid, a powder, a gel, a single-dose pouch, a solid, or a semi-solid at ambient conditions.

34. The composition of claim 33, wherein the liquid is a pourable liquid.

35. The composition of claim 22, wherein the formulation has a viscosity of about 10 to about 1000 cps, measured at a temperature of 25° C., with a Brookfield model LV viscometer, using a #2 spindle rotated at 5 rpm.

36. The composition of claim 22, wherein Formula 1 is effective to reduce the pour point of the formulation.

37. The composition of claim 22, wherein the formulation exhibits a pH of about 5 to about 13.5.

38. The composition of claim 22, having an improved rinsability as compared to an analogous heavy duty detergent based on at least one linear alkylbenzene sulfonate, at least one alcohol ether sulfate, or a mixture thereof that does not contain at least one compound of Formula 1, or mixtures thereof.

39. The composition of claim 22, wherein the at least one compound of Formula 1 is present in an amount sufficient to enable the composition to dissolve into a solution faster than an analogous heavy duty detergent based on at least one linear alkylbenzene sulfonate, at least one alcohol ether sulfate, or a mixture thereof that does not contain at least one compound of Formula 1, or mixtures thereof.

40. The composition of claim 22, wherein at least one of the compounds of Formula 1 is a potassium salt.

41. A laundry concentrate composition, comprising:
about 1% to about 99% by weight of at least one compound having the following Formula 1:

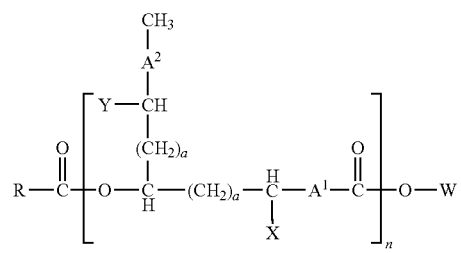

Formula 1 wherein n is an integer from 1-30;
one of X and Y is $SO_3$—Z, the other of X and Y is H, and X and Y are independently assigned in each repeating unit;
$A^1$ and $A^2$ are linear or branched, saturated or unsaturated, substituted or un-substituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or un-substituted hydrocarbon wherein the total number of carbon atoms is from 1 to about 24;
W is a monovalent or divalent metal cation, ammonium cation, substituted ammonium cation, H, or an alkyl or substituted alkyl group;
Z is H, or a monovalent or divalent metal cation, ammonium or substituted ammonium cation; and
0% to about 40% by weight of at least one additional surfactant;
about 1% to about 99% by weight of water; and
0% to about 40% by weight of at least one additive.

42. The composition of claim 41, wherein the laundry concentrate comprises surfactants in a total amount of about 20% by weight or higher.

43. The composition of claim 41, wherein the laundry concentrate comprises surfactants in a total amount of about 40% by weight or higher.

44. The composition of claim 41, wherein the laundry concentrate comprises surfactants in a total amount of about 60% by weight or higher.

45. The composition of claim 41, wherein the laundry concentrate is capable of being used in a high efficiency or regular washing machine.

46. The composition of claim 41, wherein Formula 1 is formed from all renewable carbon sources.

47. The composition of claim 46, wherein Formula 1 is made by the process comprising the steps of:
sulfonating one or more fatty acids obtained from at least one animal fat, vegetable fat, or oil source, or combinations thereof, to form a secondary sulfonate reaction; and
condensing the secondary sulfonate reaction product to form one or more estolide components.

48. The composition of claim 41, comprising about 1% to about 90% by weight of at least one nonionic surfactant.

49. The composition of claim 41, having a pH value maintained in a range that enables a clear, homogeneous liquid product, free of substantial precipitation or other physical form instability.

50. The composition of claim 49, having a pH value greater than about 8 or less than about 6.

51. The composition of claim 49, wherein the homogenous liquid product contains one or more of at least one inorganic salt, at least one non-sulfonated-estolide, or at least one fatty acid, and is maintained at a temperature in the range of about 40° F. to about 200° F.

52. A process of making at least one sulfo-estolide mixture comprising the steps of:
  providing at least one unsaturated fatty carboxylic acid having about 8 to about 24 carbon atoms;
  providing at least one chain termination agent having about 4 to about 24 carbon atoms;
  sulfonating the unsaturated fatty carboxylic acid to form at least one sulfonated intermediate; and
  reacting the chain termination agent with the sulfonated intermediate to form at least one sulfo-estolide mixture.

53. The process of claim 52, further comprising the step of treating the sulfo-estolide mixture under conditions effective to at least reduce the concentrations of sultone moieties, in which the degree of esterification of the carboxylic acid moieties is at least about 5% after the treating step.

54. The process of claim 52, further comprising the step of neutralizing the sulfo-estolide mixture to form a neutralized material comprising at least one sulfonate salt, at least one sulfonate/carboxylate salt, derivatives thereof, or combinations thereof.

55. The process of claim 54, further comprising the step of reducing the color of at least one reaction component, at least one reaction intermediate, or at least one reaction end product, before, during, or after the neutralization step.

56. The process of claim 54, wherein the neutralization is carried out using potash.

57. The process of claim 54, further comprising the step of bleaching the neutralized material with hydrogen peroxide at a pH level in the range of about 4.5 to about 7.5.

58. The process of claim 52, further comprising the step of bleaching the sulfo-estolide mixture with hydrogen peroxide.

59. The process of claim 57, wherein the pH level is in the range of about 5 to about 7.

60. The process of claim 52, wherein the unsaturated fatty carboxylic acid comprises a monounsaturated fatty acid and a saturated fatty acid.

61. The process of claim 52, wherein the chain termination agent is a saturated or unsaturated, substituted or unsubstituted, aliphatic or aromatic carboxylic acid, and derivative thereof, or a combination thereof.

62. The process of claim 52, further comprising the step of treating the sulfo-estolide mixture under conditions that reduce the carboxylic acid ester content.

63. The process of claim 52, wherein the unsaturated fatty carboxylic acid and the chain termination agent together comprise less than about 65% monounsaturated fatty carboxylic acid.

64. The process of claim 52, wherein the unsaturated fatty carboxylic acid and the chain termination agent together comprise more than about 20% saturated fatty acid.

65. The process claim 52, wherein the unsaturated fatty carboxylic acid comprises at least about 5% by weight polyunsaturated fatty acid and at least about 15% by weight monounsaturated fatty acid.

66. A process of making at least one sulfo-estolide mixture comprising the steps of:
  providing at least one unsaturated fatty acyl containing triglyceride having about 27 to about 75 carbon atoms;
  providing at least one chain termination agent having about 4 to about 24 carbon atoms;
  sulfonating the unsaturated fatty acyl to form a sulfonated intermediate;
  and
  reacting the chain termination agent with the sulfonated intermediate to form at least one sulfo-estolide mixture.

67. A laundry detergent composition, comprising:
about 5% to about 90% by weight of at least one compound having the following Formula 1:

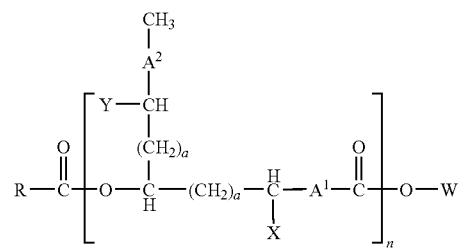

Formula 1 wherein n is an integer from 1-30;

one of X and Y is $SO_3$—Z, the other of X and Y is H, and X and Y are independently assigned in each repeating unit;

$A^1$ and $A^2$ are linear or branched, saturated or unsaturated, substituted or un-substituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or un-substituted hydrocarbon wherein the total number of carbon atoms is from 1 to about 24;

W is a monovalent or divalent metal cation, ammonium cation, substituted ammonium cation, H, or an alkyl or substituted alkyl group;

Z is H, or a monovalent or divalent metal cation, ammonium or substituted ammonium cation;

0% to about 50% by weight of at least one non ionic surfactant;

0% to about 25% by weight of at least one alcohol ether sulfate;

a sufficient amount of at least three enzymes selected from the group consisting of
  cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, beta-glucanases, arabinosidases; and derivatives thereof, and wherein the composition has a pH value in the range of about 7 to about 10.

68. A laundry detergent composition, comprising:
about 5% to about 90% by weight of at least one compound having the following Formula 1:

Formula 1

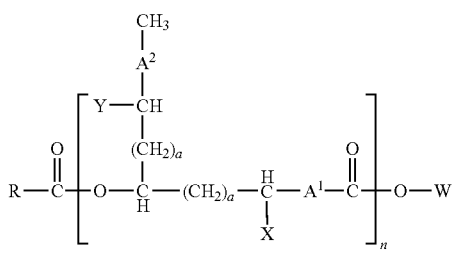

wherein n is an integer from 1-30;
one of X and Y is $SO_3$—Z, the other of X and Y is H, and X and Y are independently assigned in each repeating unit;
$A^1$ and $A^2$ are linear or branched, saturated or unsaturated, substituted or un-substituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or un-substituted hydrocarbon wherein the total number of carbon atoms is from 1 to about 24;
W is a monovalent or divalent metal cation, ammonium cation, substituted ammonium cation, H, or an alkyl or substituted alkyl group;
Z is H, or a monovalent or divalent metal cation, ammonium or substituted ammonium cation;
0% to about 50% by weight of at least one nonionic surfactant;
0% to about 25% by weight of at least one alcohol ether sulfate; and
a sufficient amount of one or two enzymes selected from the group consisting of cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, beta-glucanases, arabinosidases, and derivatives thereof; and
wherein the composition has a pH value in the range of about 7 to about 10.

69. A laundry detergent composition, comprising:
about 5% to about 90% by weight of at least one compound having the following Formula 1:

Formula 1

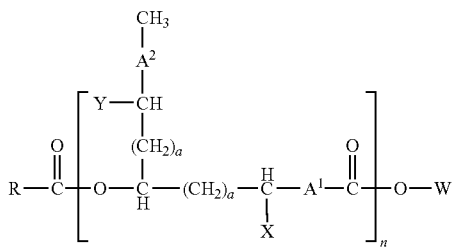

wherein n is an integer from 1-30;
one of X and Y is $SO_3$—Z, the other of X and Y is H, and X and Y are independently assigned in each repeating unit;
$A^1$ and $A^2$ are linear or branched, saturated or unsaturated, substituted or un-substituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or un-substituted hydrocarbon wherein the total number of carbon atoms is from about 1 to about 24;
W is a monovalent or divalent metal cation, ammonium cation, substituted ammonium cation, H, or an alkyl or substituted alkyl group;
Z is H, or a monovalent or divalent metal cation, ammonium or substituted ammonium cation;
0% to about 50% by weight of at least one nonionic surfactant;
0% to about 25% by weight of at least one alcohol ether sulfate, and
wherein the composition has a pH value in the range of about 7 to about 10 and is substantially free of enzymes.

70. A laundry detergent composition, comprising:
about 5% to about 90% by weight of at least one compound having the following Formula 1:

Formula 1

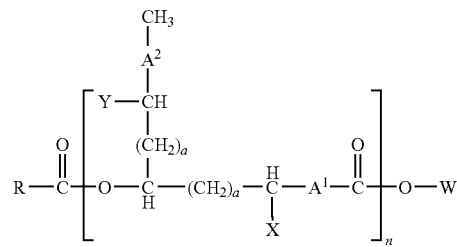

wherein n is an integer from 1-30;
one of X and Y is $SO_3$—Z, the other of X and Y is H, and X and Y are independently assigned in each repeating unit;
$A^1$ and $A^2$ are linear or branched, saturated or unsaturated, substituted or un-substituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or un-substituted hydrocarbon wherein the total number of carbon atoms is from 1 to about 24;
W is a monovalent or divalent metal cation, ammonium cation, substituted ammonium cation, H, or an alkyl or substituted alkyl group;
Z is H, or a monovalent or divalent metal cation, ammonium or substituted ammonium cation;
0% to about 50% by weight of at least one nonionic surfactant;
0% to about 25% by weight of at least one alcohol ether sulfate;
about 0.1% to about 5% by weight of metasilicate, and wherein the composition has a pH value greater than about 10.

71. A laundry detergent composition, comprising:
about 5% to about 90% by weight of at least one compound having the following Formula 1:

Formula 1

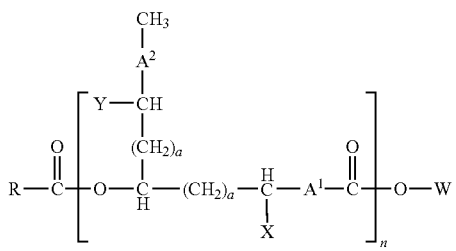

wherein n is an integer from 1-30;
one of X and Y is SO$_3$—Z, the other of X and Y is H, and X and Y are independently assigned in each repeating unit;
A$^1$ and A$^2$ are linear or branched, saturated or unsaturated, substituted or un-substituted, alkyl diradicals wherein the total number of carbons for each repeating unit is independent and in the range of C$_8$ to C$_{22}$;
a is 0, 1, or 2, and is independently assigned in each repeating unit;
R is linear or branched, saturated or unsaturated, substituted or un-substituted hydrocarbon wherein the total number of carbon atoms is from about 1 to about 24;
W is a monovalent or divalent metal cation, ammonium cation, substituted ammonium cation, H, or an alkyl or substituted alkyl group;
Z is H, or a monovalent or divalent metal cation, ammonium or substituted ammonium cation;
0% to about 50% by weight of at least one nonionic surfactant;
0% to about 25% by weight of at least one alcohol ether sulfate;
about 0.1% to about 20% by weight of sodium carbonate; and
wherein the composition has a pH value greater than about 10.

72. A laundry detergent composition, comprising:
about 2% to about 90% by weight of one or more compounds having the following Formula 1:

Formula 1

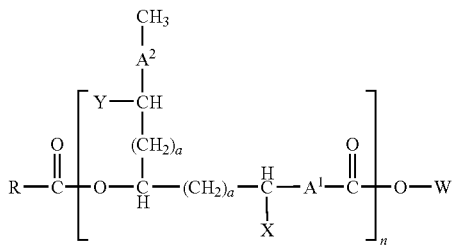

wherein n is an integer from 1-30;
one of X and Y is SO$_3$—Z, the other of X and Y is H, and X and Y are independently assigned in each repeating unit;
A$^1$ and A$^2$ are linear or branched, saturated or unsaturated, substituted or unsubstituted alkyl diradicals wherein the total number of carbons for each repeating unit is independent and in the range of C$_8$ to C$_{22}$;
a is 0, 1, or 2, and is independently assigned in each repeating unit;
R is a linear or branched, saturated or unsaturated, substituted or unsubstituted alkyl radical with from 1 to 24 carbon atoms;
W is a monovalent or divalent metal cation, ammonium or substituted ammonium cation, H, or an alkyl or substituted alkyl group;
Z is H, or a monovalent or divalent metal cation, ammonium or substituted ammonium cation;
about 2% to about 40% by weight of at least one non ionic surfactant;
0% to about 32% by weight of at least one alcohol ether sulfate;
0% to about 25% by weight of at least one 016 alpha methyl ester sulfonate;
0% to about 6% by weight of lauryl dimethlyamine oxide;
0% to about 6% by weight of C$_{12}$EO$_3$;
0% to about 10% by weight of coconut fatty acid;
0% to about 3% by weight of borax pentahydrate;
0% to about 6% by weight of propylene glycol;
0% to about 10% by weight of sodium citrate;
0% to about 6% by weight of triethanolamine;
0% to about 6% by weight of monoethanolamine;
0% to about 1% by weight of at least one fluorescent whitening agent;
0% to about 1.5% by weight of at least one anti-redeposition agent;
0% to about 2% by weight of at least one thickener;
0% to about 2% by weight of at least one thinner;
0% to about 2% by weight of at least one protease;
0% to about 2% by weight of at least one amylase; and
0% to about 2% by weight of at least one cellulase.

73. The composition according to claim 72, wherein the thickener is a hydroxyethyl cellulose polymer of MW>1 MM Daltons.

74. A laundry detergent composition, comprising:
about 2% to about 90% by weight of one or more compounds having the following Formula 1:

Formula 1

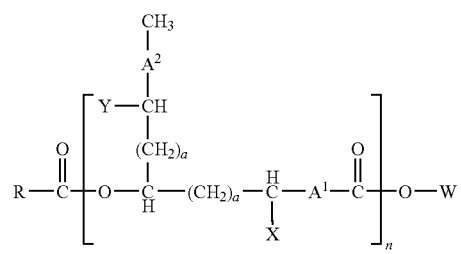

wherein n is an integer from 1-30;
one of X and Y is SO$_3$—Z, the other of X and Y is H, and X and Y are independently assigned in each repeating unit;
A$^1$ and A$^2$ are linear or branched, saturated or unsaturated, substituted or unsubstituted alkyl diradicals wherein the total number of carbons for each repeating unit is independent and in the range of C$_8$ to C$_{22}$;
a is 0, 1, or 2, and is independently assigned in each repeating unit;
R is a linear or branched, saturated or unsaturated, substituted or unsubstituted alkyl radical with from 1 to 24 carbon atoms;
W is a monovalent or divalent metal cation, ammonium or substituted ammonium cation, H, or an alkyl or substituted alkyl group;

Z is H, or a monovalent or divalent metal cation, ammonium or substituted ammonium cation;
about 2% to about 40% by weight of at least one non ionic surfactant;
0% to about 32% by weight of at least one or more alcohol ether sulfate;
0% to about 6% by weight of lauryl dimethlyamine oxide;
0% to about 6% by weight of $C_{12}EO_3$;
0% to about 10% by weight of coconut fatty acid;
0% to about 10% by weight of sodium metasilicate;
0% to about 10% by weight of sodium carbonate;
0% to about 1% by weight of at least one fluorescent whitening agent;
0% to about 1.5% by weight of at least one anti-redeposition agent;
0% to about 2% by weight of at least one thickener; and
0% to about 2% by weight of at least one thinner.

75. A green laundry detergent composition, comprising:
about 2% to about 90% by weight of one or more compounds having the following Formula 1:

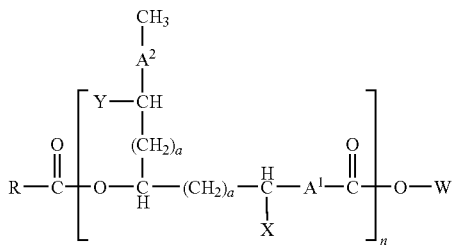

Formula 1 wherein n is an integer from 1-30;
one of X and Y is $SO_3$—Z, the other of X and Y is H, and X and Y are independently assigned in each repeating unit;

$A^1$ and $A^2$ are linear or branched, saturated or unsaturated, substituted or unsubstituted alkyl diradicals wherein the total number of carbons for each repeating unit is independent and in the range of $C_8$ to $C_{22}$;
a is 0, 1, or 2, and is independently assigned in each repeating unit;
R is a linear or branched, saturated or unsaturated, substituted or unsubstituted alkyl radical with from 1 to 24 carbon atoms;
W is a monovalent or divalent metal cation, ammonium or substituted ammonium cation, H, or an alkyl or substituted alkyl group;
Z is H, or a monovalent or divalent metal cation, ammonium or substituted ammonium cation;
0% to about 30% by weight of at least one O16 methyl ester sulfonate;
0% to about 30% by weight of at least one O12 methyl ester sulfonate;
0% to about 30% by weight of sodium lauryl sulfate;
0% to about 30% by weight of sodium stearoyl lactylate;
0% to about 30% by weight of sodium lauroyl lactate;
0% to about 60% by weight of alkyl polyglucoside;
0% to about 60% by weight of polyglycerol monoalkylate;
0% to about 30% by weight of lauryl lactyl lactate;
0% to about 30% by weight of saponin;
0% to about 30% by weight of rhamnolipid;
0% to about 30% by weight of sphingolipid;
0% to about 30% by weight of glycolipid;
0% to about 30% by weight of at least one abietic acid derivative; and
0% to about 30% by weight of at least one polypeptide.

76. The composition of any one of claims 67, 68, 69, 70, 71, 72, 74, or 75, wherein at least one of the compounds of Formula 1 is a potassium salt.

* * * * *